US012325754B2

(12) United States Patent
Glennie et al.

(10) Patent No.: US 12,325,754 B2
(45) Date of Patent: Jun. 10, 2025

(54) CANCER AND B-CELL RELATED DISEASE THERAPY

(71) Applicant: University of Southampton, Southampton (GB)

(72) Inventors: Martin John Glennie, Southampton (GB); Aymen Al-Shamkhani, Southampton (GB); Mark Steven Cragg, Southampton (GB); Sean Hua Lim, Southampton (GB)

(73) Assignee: University of Southampton, Southampton (GB)

( * ) Notice: Subject to any disclaimer, the term of this patent is extended or adjusted under 35 U.S.C. 154(b) by 0 days.

(21) Appl. No.: 16/321,367

(22) PCT Filed: Jul. 28, 2017

(86) PCT No.: PCT/GB2017/052222
§ 371 (c)(1),
(2) Date: Jan. 28, 2019

(87) PCT Pub. No.: WO2018/020273
PCT Pub. Date: Feb. 1, 2018

(65) Prior Publication Data
US 2019/0169306 A1 Jun. 6, 2019

(30) Foreign Application Priority Data
Jul. 29, 2016 (GB) ..................................... 1613167

(51) Int. Cl.
*C07K 16/28* (2006.01)
*A61K 39/00* (2006.01)
*A61P 35/00* (2006.01)

(52) U.S. Cl.
CPC .......... *C07K 16/2887* (2013.01); *A61P 35/00* (2018.01); *C07K 16/2878* (2013.01); *A61K 2039/507* (2013.01); *A61K 2039/545* (2013.01); *C07K 2317/21* (2013.01); *C07K 2317/24* (2013.01); *C07K 2317/73* (2013.01); *C07K 2317/732* (2013.01); *C07K 2317/75* (2013.01)

(58) Field of Classification Search
None
See application file for complete search history.

(56) References Cited

U.S. PATENT DOCUMENTS

| | | | |
|---|---|---|---|
| 8,481,029 B2 | 7/2013 | Glennie et al. | |
| 9,248,183 B2 | 2/2016 | Glennie et al. | |
| 9,926,374 B2 | 3/2018 | Glennie et al. | |
| 2012/0321646 A1* | 12/2012 | Kohrt | C07K 16/32 424/174.1 |
| 2016/0215056 A1* | 7/2016 | Glennie | A61P 35/02 |

FOREIGN PATENT DOCUMENTS

WO WO-2008063771 A2 * 5/2008 ........... A61K 39/395
WO 2011071871 A1 6/2011

OTHER PUBLICATIONS

Kohrt et al. Blood, vol. 117, No. 8 ,Feb. 24, 2011 (Year: 2011).*
Kohrt et al., Blood, vol. 117, No. 8, pp. 2423-2432, Feb. 24, 2011 (Year: 2011).*
Van de Ven et al. Immunotherapy (2015) 7(6), 655-667. (Year: 2015).*
Roghanian University of Southhampton UK.*
Vitale et al., Cancer Clinical Resaerch, vol. 18, No. 14, pp. 3812-3821, Jul. 15, 2012. (Year: 2012).*
French et al., "Eradication of lymphoma by CD8 T cells following anti-CD40 monoclonal antibody therapy is critically dependent on CD27 costimulation", Blood, Jun. 1, 2007, pp. 4810-4815, 109(11).
Kohrt et al., "CD137 stimulation enhances the antilymphoma activity of anti-CD20 antibodies", Blood, Feb. 24, 2011, pp. 2423-2432, 117(8).
Melero et al., "Agonist antibodies to TNFR molecules that costimulate T and NK cells", Clinical Cancer Research: an Official Journal of the American Association for Cancer Research, Mar. 1, 2013, pp. 1044-1053, 19(5).
Srivastava et al., "Effects of interleukin-18 on natural killer cells: costimulation of activation through Fc receptors for Immunoglobulin", Cancer Immunology, Immunotherapy, Jun. 2013, pp. 1073-1082, 62(6).
Robertson et al., "A dose-escalation study of recombinant human interleukin-18 in combination with rituximab in patients with non-Hodgkin lymphoma", Journal of Immunotherapy, Jul. 2013, pp. 331-341, 36(6).
Laprevotte et al., "Recombinant Human IL-15 Trans-Presentation by B Leukemic Cells from Chronic Lymphocytic Leukemia Induces Autologous NK Cell Proliferation Leading to Improved Anti-CD20 Immunotherapy", The Journal of Immunology, Oct. 1, 2013, pp. 3634-3640, 191(7).

(Continued)

*Primary Examiner* — Jana A Hines
*Assistant Examiner* — Khatol S Shahnan Shah
(74) *Attorney, Agent, or Firm* — Armstrong Teasdale LLP

(57) ABSTRACT

The disclosure relates to a method of treatment or prevention of B-cell related disease in a subject comprising the administration of a binding molecule capable of binding to a B-cell and promoting killing of the B-cell; and an immunostimulatory agent arranged to stimulate effector lymphocytes, such as NK and/or T cells. Additionally, an anti-CD27 binding agent for use in a combination therapy with an anti-CD20 binding agent for the treatment or prevention of B-cell related disease in a subject. The disclosure also relates to a method of treatment or prevention of cancer in a subject comprising the administration of a cancer-cell-depleting binding agent capable of binding to the cancer cell and promoting killing of the cancer cell; and an immunostimulatory agent arranged to stimulate NK and/or T-cell activation. Additionally, an anti-CD27 binding agent for use in a combination therapy with a cancer-cell-depleting binding agent for the treatment or prevention of cancer in a subject.

16 Claims, 53 Drawing Sheets

Figure 1A:
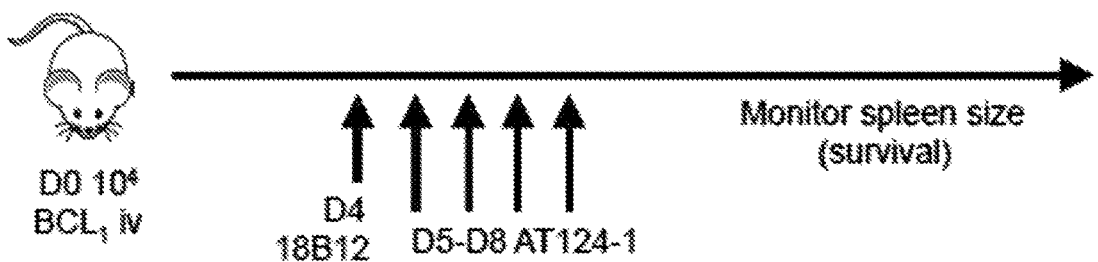

Specification includes a Sequence Listing.

(56) References Cited

OTHER PUBLICATIONS

Kohrt et al., "Anti-KIR antibody enhancement of anti-lymphoma activity of natural killer cells as monotherapy and in combination with anti-CD20 antibodies", Blood, Jan. 30, 2014, pp. 678-686, 123(5).

Kellner et al., "Enhancing natural killer cell-mediated lysis of lymphoma cells by combining therapeutic antibodies with CD20-specific immunoligands engaging NKG2D or NKp30", Oncoimmunology, Jun. 5, 2015, 5(1).

Koen Van De Ven et al., "Targeting the T-cell co-stimulatory CD27/CD70 pathway in cancer immunotherapy: rationale and potential", Immunotherapy, Jun. 22, 2015, pp. 655-667, 7(6).

Sanmamed et al., "Agonists of Co-stimulation in Cancer Immunotherapy Directed Against CD137, OX40, GITR, CD27, CD28, and ICOS", Seminars in Oncology, Aug. 2015, pp. 640-655, 42(4).

Turaj et al., "Anti-CD27 Enhances Lymphoma Immunotherapy through Profound Myeloid Cell Recruitment", Blood, Dec. 2, 2016, 128(22).

Patents Act 1977: Search Report under Section 17(5) for GB1613167.4 issued on Apr. 3, 2017, 5 pages.

International Search Report and Written Opinion for PCT/GB2017/052222 issued on Nov. 30, 2017, 21 pages. 2017.

Kohrt et al., "Targeting CD137 enhances the efficacy of cetuximab", J Clin Invest, 2014, 124(6), pp. 2668-2682.

Kohrt et al., "Retraction: Targeting CD137 enhances the efficacy of cetuximab", J Clin Invest, 2019, 129(6), pp. 2595.

Kohrt et al., "Stimulation of natural killer cells with a CD137-specific antibody enhances trastuzumab efficacy in xenotransplant models of breast cancer", J Clin Invest, 2012, 122(3), pp. 1066-1075.

Kohrt et al., "Retraction: Stimulation of natural killer cells with a CD137-specific antibody enhances trastuzumab efficacy in xenotransplant models of breast cancer", J Clin Invest, 2019, 129(6), pp. 2595.

Kohrt et al., "CD137 stimulation enhances the antilymphoma activity of anti-CD20 antibodies", Blood, 2011, 117(8), pp. 2423-2432.

Kohrt et al., "Retraction: CD137 stimulation enhances the antilymphoma activity of anti-CD20 antibodies", Blood, 2019, 134(7), pp. 658.

He et al., "Agonist anti-human CD27 monoclonal antibody induces T cell activation and tumor immunity in human CD27-transgenic mice", J Immunol, 2013, 191(8), pp. 4174-4183.

* cited by examiner

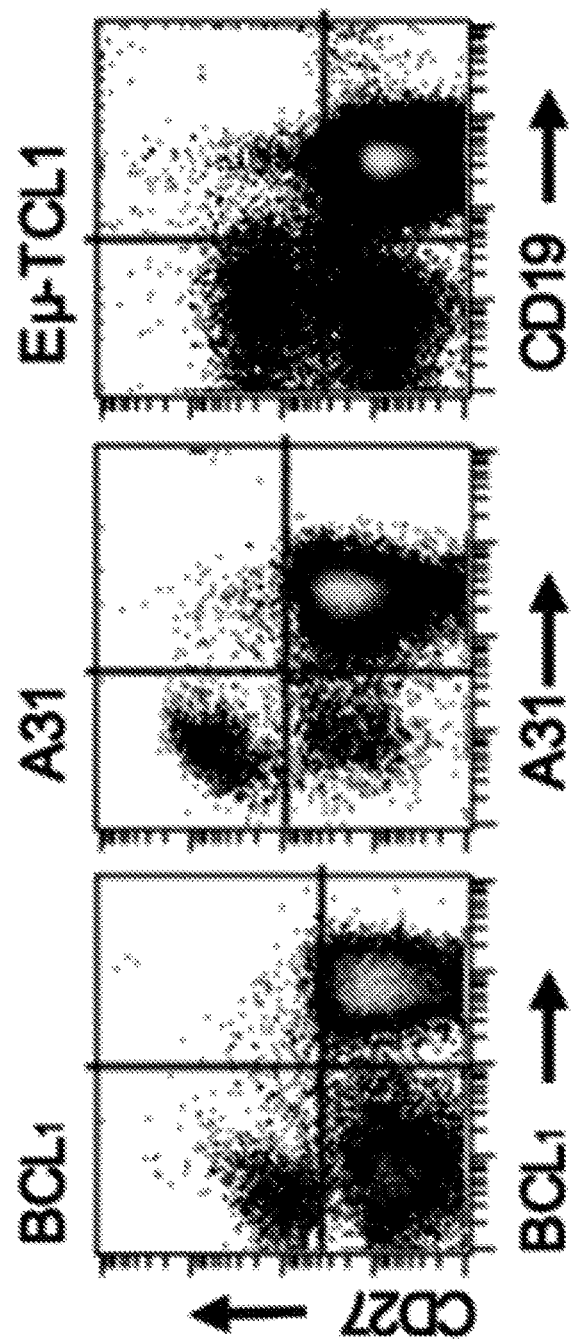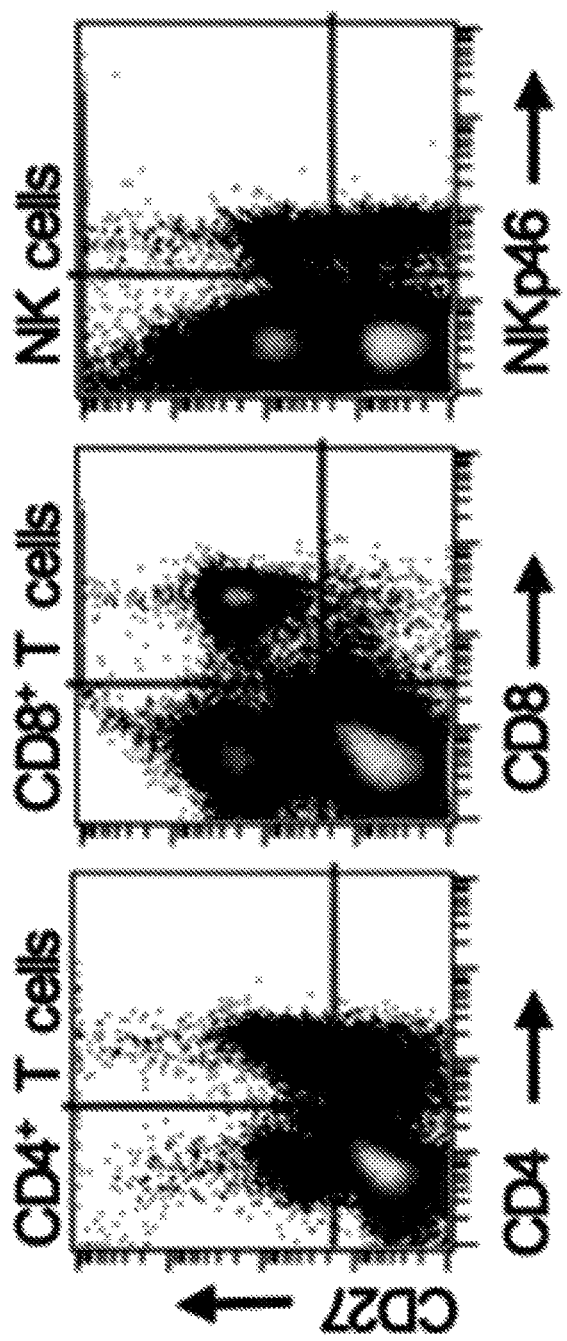

CANCER AND B-CELL RELATED DISEASE THERAPY

RELATED APPLICATIONS

This application is a 371 National Phase Application of International Application No. PCT/GB2017/052222 filed Jul. 28, 2017, which claims the benefit of and priority to United Kingdom Application No. GB 1613167.4 filed Jul. 29, 2016; the entire contents of each of the foregoing applications are hereby incorporated by reference herein.

The present invention relates to a combination therapy to treat or prevent cancer and/or treat or prevent B-cell related disease, such as B-cell lymphoma, including methods of treatment or prevention, uses, compositions and kits for treating cancer or other B-cell related disease in a subject.

BACKGROUND OF THE INVENTION

Cancer is a condition where cells in a specific part of the body grow and reproduce uncontrollably, such as B-cell malignancies or other solid malignant tumours. There are over 12,000 new cases of B-cell malignancies diagnosed in the United Kingdom each year. B-cell cancers can be divided broadly into high grade (e.g. diffuse large B-cell lymphoma [DLBCL]) or indolent (e.g. follicular lymphoma [FL] and chronic lymphocytic leukaemia [CLL]) based on their rate of progression. DLBCL, CLL and FL are the three most common subtypes, accounting for 80% of B-cell malignancies. High grade lymphomas are potentially curable whereas indolent lymphomas have a relapsing remitting course. Standard frontline therapy of most B-cell malignancies consists of immune-chemotherapy with rituximab, an anti-CD20 monoclonal antibody (mAb). Despite being considered a treatable and potentially curable cancer, approximately 30% of DLBCL cases will relapse after frontline therapy. There is no established standard for second line therapy but if a patient is fit enough, consolidation with an autologous stem cell transplant is undertaken. Even with transplantation, only 50% of cases will achieve durable remissions. Thus the great majority of patients with relapsed DLBCL will eventually succumb to the disease. Whilst the indolent diseases lead a less aggressive course, successive remissions become increasingly shorter in duration, necessitating different therapies with each relapse. Thus there is a clear clinical need for more novel therapeutic agents in B-cell lymphoma to increase the depth of remissions on initial therapy, and to lengthen remissions on relapse.

Rituximab (Rituxan™) is a so-called direct-targeting mAb, which binds to the CD20 molecule on the surface of normal and malignant B cells. The mAb then engages immune effectors cells, such as macrophages, through Fc:Fc gamma receptor interaction, leading to tumour cell killing by antibody directed cellular cytotoxicity and/or phagocytosis (ADCC/ADCP). There is now good evidence in pre-clinical models that monocytes and macrophages are the key effector cells in mediating ADCC/ADCP with anti-CD20 mAb. Depletion of macrophages but not NK cells in murine models decreases mAb efficacy. It is controversial whether rituximab might induce cell death through direct signalling effects and complement. Further, it has also been postulated that rituximab might induce an adaptive immune response. This is suggested by the development of delayed clinical responses as many as 112 days after rituximab administration, which is in keeping with the time taken to induce T-cell immunity. However, incontrovertible objective evidence in patients and fully syngeneic mouse models of this is still lacking. As detailed above, rituximab has now been incorporated into frontline therapy of B-cell malignancies, often in combination with chemotherapy, where it has been shown in randomised controlled trials to increase responses by up to 20% in FL and DLBCL. It is also employed as a single agent in some indolent lymphomas. As rituximab destroys B cells, it is used to treat diseases that are characterised by overactive, dysfunctional, or excessive numbers of B cells. This includes many lymphomas, leukaemias, transplant rejection, and autoimmune disorders.

In addition to B-cell lymphomas, there is ongoing need to find new therapies for other solid tumours, such as neuroblastoma and melanoma. As an example, GD2 is a disialoganglioside expressed on tumors of neuroectodermal origin, including human neuroblastoma and melanoma, with restricted expression on normal tissues. The relatively tumor specific expression of GD2 makes it a suitable target for immunotherapy with monoclonal antibodies, such as anti-GD2 antibodies. Dinutuximab is the first anti-GD2 monoclonal antibody approved in combination with GM-CSF, IL-2, and retinoic acid for maintenance treatment of pediatric patients with high-risk neuroblastoma. Ongoing research with dinutuximab is being conducted for non-responders to initial therapies, in combination with chemotherapy, or in other cancers.

There are currently several clinical trials investigating new combinations of agents, and there is an ongoing need to find alternative and improved therapies.

An aim of the present invention is to provide an alternative or improved therapy for B-cell lymphoma, and other B-cell disease and cancer, patients.

SUMMARY OF THE INVENTION

According to a first aspect of the invention there is provided a method of treatment or prevention of B-cell related disease in a subject comprising the administration of a binding molecule capable of binding to a B-cell and promoting killing of the B-cell; and an immunostimulatory agent arranged to stimulate effector lymphocytes, such as NK cells and/or T cells.

According to another aspect of the invention, there is provided a method of treatment or prevention of B-cell related disease in a subject comprising the administration of an anti-CD20 binding molecule and an anti-CD27 binding molecule to the subject.

According to another aspect of the invention, there is provided a method of treatment or prevention of B-cell related disease in a subject comprising the administration of rituximab and varlilumab to the subject.

According to another aspect of the invention, there is provided an anti-CD27 binding agent for use in a combination therapy with an anti-CD20 binding agent for the treatment or prevention of B-cell lymphoma in a subject.

According to another aspect of the invention, there is provided a composition comprising an anti-CD20 binding agent and an anti-CD27 binding agent.

According to another aspect of the invention, there is provided a kit for treatment or prevention of B-cell related disease in a subject, the kit comprising an anti-CD20 binding agent and an anti-CD27 binding agent.

According to another aspect of the invention, there is provided a composition according to the invention for use as a medicament.

According to another aspect of the invention, there is provided a composition according to the invention, or kit according to the invention, for use in the treatment or prevention of B-cell related disease in a subject.

The invention advantageously demonstrates that NK- and optionally T-cell-stimulating agents, such as anti-CD27 mAb, can increase the potency of rituximab and other anti-CD20 mAb to a level that will cure lymphoma bearing mice. Specifically, it is demonstrated that NK and T-cell-stimulating therapy leads to an increase in myeloid cell infiltration at the tumour site. This is the first time that an immune stimulating mAb (anti-CD27) has been shown to promote the activity of myeloid cells to augment an anti-B-cell mAb. Therefore, B-cell related disease characterised by overactive, dysfunctional, or excessive numbers of B cells may be treated or prevented. This includes many lymphomas, leukaemias, transplant rejection, and autoimmune disorders.

According to another aspect of the invention there is provided a method of treatment or prevention of cancer in a subject comprising the administration of a cancer-cell-depleting binding agent capable of binding to the cancer cell and promoting killing of the cancer cell; and an immunostimulatory agent arranged to stimulate an NK cell and/or a T cell.

Advantageously, the invention recognises that the mechanism of action of a binding agent, such as an antibody, that can kill a cancer cell as a result of recruiting Fc receptor expressing cellular (myeloid) effectors can be enhanced by increased myeloid cell infiltration into the cancer site via immunostimulatory agent arranged to stimulate NK cell and/or T cell activation.

According to another aspect of the invention, there is provided an anti-CD27 binding agent for use in a combination therapy with a cancer-cell-depleting binding agent for the treatment or prevention of cancer in a subject.

According to another aspect of the invention, there is provided a kit for treatment or prevention of cancer in a subject, the kit comprising a cancer-cell-depleting binding agent and an anti-CD27 binding agent.

According to another aspect of the invention, there is provided a composition according to the invention, or kit according to the invention, for use in the treatment or prevention of cancer.

DETAILED DESCRIPTION

According to a first aspect of the invention there is provided a method of treatment or prevention of B-cell related disease in a subject comprising the administration of a binding molecule capable of binding to a B-cell and promoting killing of the B-cell; and an immunostimulatory agent arranged to stimulate NK and optionally T cell activation.

The subject may be mammalian, such as human. In one embodiment, the subject is a human patient afflicted with, or at risk of, B-cell related disease. In one embodiment, the targeted B-cell is human. Additionally or alternatively, the targeted NK/T cells may be human. The targeted CD20 and/or targeted CD27 may be human.

In one embodiment, the B-cell related disease is cancer, such as B-cell lymphoma. The B-cell related disease may be any disease characterised by overactive, dysfunctional, or excessive numbers of B-cells. The B-cell related disease may be any of lymphomas, leukaemias, transplant rejection, or autoimmune disorders characterised by overactive, dysfunctional, or excessive numbers of B-cells, such as rheumatoid arthritis, lupus, multiple sclerosis, autoimmune thrombocytopenia or other cytopenias.

The binding molecule capable of binding to a B-cell and promoting killing of the B-cell may herein be known as 'the B-cell binding molecule'. The B-cell binding molecule' may be a B-cell depleting antibody.

In one embodiment, the binding molecule capable of binding to a B-cell is an anti-CD20 binding molecule. In another embodiment, the binding molecule capable of binding to a B-cell may be an anti-CD5 binding molecule. In another embodiment, the binding molecule capable of binding to a B-cell may be an anti-CD19 binding molecule. In another embodiment, the binding molecule capable of binding to a B-cell may be an anti-CD37 binding molecule. In another embodiment, the binding molecule capable of binding to a B-cell may be an anti-CD38 binding molecule. In another embodiment, the binding molecule capable of binding to a B-cell may be an anti-CD52 binding molecule. In another embodiment, the binding molecule capable of binding to a B-cell may be an anti-MHC II binding molecule. In another embodiment, the binding molecule capable of binding to a B-cell may be an anti-HLA DR binding molecule.

The binding molecule capable of binding to a B-cell may be any one of an anti-CD20 binding molecule; anti-CD5 binding molecule; anti-CD19 binding molecule; anti-CD37 binding molecule; anti-CD38 binding molecule; anti-CD52 binding molecule; anti-MHC II binding molecule; or an anti-HLA DR binding molecule.

The B-cell binding molecule may be capable of binding to a B-cell surface receptor/marker, such as CD20, with at least nanomolar affinity. For example at least 100 nM affinity, at least 10 nM affinity, or at least 1 nM affinity. In another embodiment, the B-cell binding molecule may be capable of binding to a B-cell surface receptor/marker, such as CD20, with at least picomolar affinity. For example at least 100 pM affinity, or less such as at least 50 pM affinity. The skilled person will understand that reference to "at least" in relation to a binding affinity is understood to mean the stated affinity, or more affinity/stronger binding).

The B-cell binding molecule may be an antagonist of the B-cell or B-cell activity.

The B-cell binding molecule may comprise an antibody, antibody fragment or antibody mimetic. In one embodiment, the B-cell binding molecule is an antibody.

The B-cell binding molecule may comprise rituximab. The B-cell binding molecule may comprise at least a variable domain of rituximab. The B-cell binding molecule may comprise at least the CDRs of rituximab. In another embodiment, the B-cell binding molecule may compete for binding with rituximab. In another embodiment, the B-cell binding molecule may bind the same epitope as rituximab.

The rituximab may comprise the anti-CD20 antibody as described in EP2000149, U.S. Pat. No. 5,736,137, or Maloney Blood 1997; 90(6); 2188-2915, which are incorporated herein by reference.

In one embodiment, the B-cell binding molecule may comprise CDRs of the following sequences:

```
VH CDR1:
                                    (SEQ ID NO: 1)
SYNMH;

VH CDR2:
                                    (SEQ ID NO: 2)
AIYPGNGDTSYNQKFKG;

VH CDR3:
                                    (SEQ ID NO: 3)
STYYGGDWYFNV;
```

-continued

VL CDR1:
(SEQ ID NO: 4)
RASSSVSYIH;

VL CDR1:
(SEQ ID NO: 5)
ATSNLAS;
and

VL CDR1:
(SEQ ID NO: 6)
QQWTSNPPT (i.e. rituximab CDRs).

The B-cell binding molecule may comprise the variable heavy chain domain sequence of:

(SEQ ID NO: 7)
QVQLQQPGAELVKPGASVKMSCKASGYTFTSYNMHWVKQTPGRGLEWIGA
IYPGNGDTSYNQKFKGKATLTADKSSSTAYMQLSSLTSEDSAVYYCARST
YYGGDWYFNVWGAGTTVTVS, or a variant thereof. Additionally, or alternatively, the B-cell binding molecule may comprise the variable light chain domain sequence of:

(SEQ ID NO: 8)
QIVLSQSPAILSASPGEKVTMTCRASSSVSYIHWFQQKPGSSPKPWIYAT
SNLASGVPVRFSGSGSGTSYSLTISRVEAEDAATYYCQQWTSNPPTFGGG
TKLEIK, or a variant thereof.

The B-cell binding molecule may comprise the heavy chain sequence of:

(SEQ ID NO: 9)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSAASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKAEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K (rituximab heavy chain), or a variant thereof.

Additionally, or alternatively, the B-cell binding molecule may comprise the light chain sequence of:

(SEQ ID NO: 10)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPT**FGGG

TKLEIK**RTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC (rituximab light chain), or a variant thereof.

The B-cell binding molecule may comprise a sequence having at least 90%, 95%, 98%, or 99% identity to rituximab. Reference to the 90%, 95%, or 99% identity may be to the framework regions of the VH and/or VL domains. In particular, the CDR regions may be identical, but the framework regions may vary by up to 1%, 5%, or 10%. Such a binding molecule may differ from the sequences of rituximab by a small number of functionally inconsequential amino acid substitutions (e.g., conservative substitutions), deletions, or insertions.

In another embodiment, the B-cell binding molecule may comprise a biosimilar of rituximab, such as Reditux™.

In another embodiment, the B-cell binding molecule may comprise obinutuzumab or a biosimilar of obinutuzumab (Mossner et al. Blood 2010, 115:4393-4402 which is herein incorporated by reference). Obinutuzumab (Gazyva™) is a humanized monoclonal antibody, originated by GlycArt Biotechnology AG and developed by Roche as a cancer treatment. Obinutuzumab binds to CD20 on B cells (with an overlapping epitope with rituximab) and causes these cells to be destroyed by engaging the adaptive immune system, directly activating intracellular apoptosis pathways, and activating the complement system. The B-cell binding molecule may comprise at least a variable domain of obinutuzumab. The B-cell binding molecule may comprise at least the CDRs of obinutuzumab. In another embodiment, the B-cell binding molecule may compete for binding with obinutuzumab. In another embodiment, the B-cell binding molecule may bind the same epitope as obinutuzumab.

In another embodiment, the B-cell binding molecule may comprise ocrelizumab or a biosimilar of ocrelizumab (Morschhauser F et al. Annals of Oncology 2010:21:1870-1876, which is herein incorporated by reference). The B-cell binding molecule may comprise at least a variable domain of ocrelizumab. The B-cell binding molecule may comprise at least the CDRs of ocrelizumab. In another embodiment, the B-cell binding molecule may compete for binding with ocrelizumab. In another embodiment, the B-cell binding molecule may bind the same epitope as ocrelizumab.

In another embodiment, the B-cell binding molecule may comprise ofatumumab or a biosimilar of ofatumumab (Coiffier et al. Blood 111:1094-1100, which is herein incorporated by reference). The B-cell binding molecule may comprise at least a variable domain of ofatumumab. The B-cell binding molecule may comprise at least the CDRs of ofatumumab. In another embodiment, the B-cell binding molecule may compete for binding with ocrelizumab. In another embodiment, the B-cell binding molecule may bind the same epitope as ofatumumab.

In another embodiment, the B-cell binding molecule may comprise veltuzumab or a biosimilar of veltuzumab (Immunomedics, Inc, as described in Polito et al. EMJ Oncol. 2014; 2:63-69, which is herein incorporated by reference). The B-cell binding molecule may comprise at least a variable domain of veltuzumab. The B-cell binding molecule may comprise at least the CDRs of veltuzumab. In another embodiment, the B-cell binding molecule may compete for binding with veltuzumab. In another embodiment, the B-cell binding molecule may bind the same epitope as veltuzumab.

In another embodiment, the B-cell binding molecule may comprise TRU-015 or a biosimilar of TRU-015 (TRU-015 is an anti-CD20 IgG fusion protein of Trubion Pharmaceuticals Inc and Pfizer Inc as described in Polito et al. EMJ Oncol. 2014; 2:63-69, which is herein incorporated by reference). The B-cell binding molecule may comprise at least a variable domain of TRU-015. The B-cell binding molecule may comprise at least the CDRs of TRU-015. In another embodiment, the B-cell binding molecule may compete for binding with TRU-015. In another embodiment, the B-cell binding molecule may bind the same epitope as TRU-015.

In another embodiment, the B-cell binding molecule may comprise EMAB-6 or a biosimilar of EMAB-6 (EMAB-6 a chimeric anti-CD20 monoclonal antibody as described in de Romeuf 2008 March; 140(6):635-43. doi: 10.1111/j.1365-2141.2007.06974.x. and Polito et al. EMJ Oncol. 2014; 2:63-69, which are herein incorporated by reference). The B-cell binding molecule may comprise at least a variable domain of EMAB-6. The B-cell binding molecule may comprise at least the CDRs of EMAB-6. In another embodiment, the B-cell binding molecule may compete for binding with EMAB-6. In another embodiment, the B-cell binding molecule may bind the same epitope as EMAB-6.

In another embodiment, the B-cell binding molecule may comprise RhumAb v114 or a biosimilar of RhumAb v114 (as described in Polito et al. EMJ Oncol. 2014; 2:63-69, which is herein incorporated by reference). The B-cell binding molecule may comprise at least a variable domain of RhumAb v114. The B-cell binding molecule may comprise at least the CDRs of RhumAb v114. In another embodiment, the B-cell binding molecule may compete for binding with RhumAb v114. In another embodiment, the B-cell binding molecule may bind the same epitope as RhumAb v114.

The skilled person will understand that other anti-B-cell, such as anti-CD20, antibodies, or antibody-like peptides may be available for use in depletion of B-cells according to the invention.

The B-cell binding molecule may be capable of ADCC (Antibody-Dependent Cell-mediated Cytotoxicity) and/or ADCP (Antibody-Dependent Cell-mediated Phagocytosis) killing of the B-cell. For example, the B-cell binding molecule may comprise an Fc portion, preferably a human Fc portion. Fc-mediated effector mechanisms such as ADCC and ADCP are well known in the art, including modifications to enhance ADCC and ADCP, which are known to the skilled person and may be provided in the B-cell binding molecule discussed herein.

In another embodiment the B-cell binding molecule is a fully human monoclonal antibody of the IgG1, IgG2, IgG3 or IgG4 isotype. In another embodiment of the invention, the targeted binding agent is a fully human monoclonal antibody of the IgG1 isotype. The IgG1 isotype has increased potential to elicit ADCC in comparison with other isotypes, which may lead to improved efficacy. The IgG1 isotype has improved stability in comparison with other isotypes, e.g. IgG4, which may lead to improved bioavailability, or improved ease of manufacture or a longer half-life.

The immunostimulatory agent arranged to stimulate NK cell activation may be specific to lymphocyte activation. In one embodiment, the immunostimulatory agent arranged to stimulate NK cell activation may be specific to NK cell activation. Alternatively, the immunostimulatory agent arranged to stimulate NK cell activation may be specific to NK cell activation and T-cell activation. The immunostimulatory agent arranged to stimulate NK cell activation may comprise or consist of a binding molecule arranged to bind to the NK cell (herein termed "the NK cell binding molecule"). The binding may be specific. In another embodiment, the NK cell binding molecule may also bind T-cells.

The skilled person will understand that the NK cell binding molecule may also bind other lymphocytes, such as T-cells, via a common marker/receptor. For example CD27, CD137, and OX40 are found on both NK cells and on T cells. Therefore the immunostimulatory agent arranged to stimulate NK and optionally T cell activation may be the same agent that can bind and stimulate both cell types.

Alternatively, cell markers/receptors such as NKp46, NKG2D, NKp30 and CD16 may only be found on NK cells, and not T-cells. Therefore in one embodiment, the NK cell stimulation may be specifically targeted/effected by targeting the immunostimulatory agent to any of NKp46, NKG2D, NKp30 or CD16.

The NK cell binding molecule may comprise an anti-CD27 binding molecule. The NK cell binding molecule may comprise any one of anti-CD27 binding molecule; anti-CD137 binding molecule (Kohrt et al Blood 2011; 117(8): 2423-32, which is herein incorporated by reference), anti-NKp46 binding molecule, anti-NKp30 binding molecule, anti-NKG2D binding molecule (Ehrlich et al Journal of Immunology 2005 174(4); 1922-1931, also patent U.S. Pat. No. 7,879,985 B2, which are herein incorporated by reference), anti-CD16 binding molecule, or anti-OX40 binding molecule (Curti et al. Cancer Research 2013; 73(24):1-10; Voo et al Journal of Immunology 2013; 191(7); 3641-50, which are herein incorporated by reference). Such targets are based on established mouse data reviewed in Smyth et al Molecular Immunology 2005; 42(4):501-10, which is herein incorporated by reference.

The NK cell binding molecule may be capable of binding to a NK cell surface receptor/marker, such as CD27, with at least nanomolar affinity. For example at least 100 nM affinity, at least 10 nM affinity, or at least 1 nM affinity. In another embodiment, the NK cell binding molecule may be capable of binding to a NK cell surface receptor/marker, such as CD27, with at least picomolar affinity. For example at least 100 pM affinity, or less such as at least 50 pM affinity.

The NK cell binding molecule may be an agonist of the NK cell or NK cell activity. Additionally, the NK cell binding molecule may be an agonist of the T-cell or T-cell activity.

The NK cell binding molecule may comprise an antibody, antibody fragment or antibody mimetic. In one embodiment, the NK cell binding molecule is an antibody. In one embodiment, the NK cell binding molecule comprises an immunomodulatory antibody, such as an immunomodulatory monoclonal antibody. For example, the NK cell binding molecule may comprise an immunomodulatory antibody that is specific for CD27, for example a CD27 presented on a NK cell.

The NK cell binding molecule may comprise varlilumab (Celldex Therapeutics Inc.).

Varlilumab (1F5, CDX-1127) is a recombinant and fully human IgG1kappa mAb that binds with high affinity to human CD27, a critical molecule in the activation pathway of lymphocytes. It is the only anti-CD27 mAb known to be in clinical development. Once bound, varlilumab blocks CD70 binding to CD27. The agonist activity of varlilumab is demonstrated through a variety of in vitro and in vivo studies, and confirmed in preliminary results of a Phase I trial. In detail, in vitro, varlilumab is able to enhance human T cell activation and proliferation when there is simultaneous TCR stimulation, and when the mAb is crosslinked. Using a human CD27 (huCD27) Tg mouse model, varlilumab also induced T cell proliferation and IFNγ release when combined with TCR stimulation in an in vitro setting. Functionally, varlilumab also enhanced CD8 T cell mediated IFNγ release to OVA. Given that varlilumab is an agonistic mAb and several B-cell tumours express CD27, it is possible that it might have tumorigenic effects. However, when primary human B-cell lymphoma cells that express high levels of CD27 were co-cultured with varlilumab either alone, or crosslinked, tumour cell proliferation was not observed (Vitale et al. 2012. *Clinical Cancer Research* 18, pp 3812-3821). The anti-tumour activity of varlilumab has been demonstrated in several different mouse models. In xenograft models, varlilumab inhibited the growth of human Burkitt lymphoma-derived Raji and Daudi cells in immunodeficient SCID mice. Further in vitro studies showed that the activity of varlilumab in these xenograft models is mediated through ADCC. There was no evidence to support complement-mediated cytotoxicity or direct cell death induction. These results indicate that varlilumab might also deplete CD27 expressing T cells. However no significant changes in lymphocyte subpopulations were observed when varlilumab was administered to cynomolgus macaques (Vitale et al. 2012. *Clinical Cancer Research* 18, pp 3812-3821). Varlilumab has also been tested in more relevant immune-competent, syngeneic models using huCD27 Tg mice. Improvement in survival was observed in BCL1 lymphoma, CT26 colon carcinoma and EL4 lymphoma and EG7 lymphoma models. In CT26, EL4 and EG7 models some of the varlilumab-treated mice remained protected upon tumour rechallenge, indicative of generation of a potent memory response. In the CT26 and EG7 models, CD4 and CD8 T cells were both required for varlilumab to mediate its antitumour activity. Varlilumab has also been tested in combination with other agents. In the EG7 thymoma model, combining varlilumab with cyclophosphamide improved survival suggesting that chemotherapeutic agents can assist with tumour control without impairing varlilumab-driven immune responses. Varlilumab combined with checkpoint blockers such as anti-PD-L1, hypothesised to offer synergism in immune stimulation, also improved tumour control. This is the first time that an immune stimulating mAb, such as varlilumab (anti-CD27), has been shown to promote the activity of myeloid cells to augment an anti-lymphoma mAb, such as rituximab, leading to significant and surprising improvements in in vivo mouse model survival times.

The NK cell binding molecule may comprise at least a variable domain of varlilumab. The NK cell binding molecule may comprise the heavy and/or light chain variable domain(s) of varlilumab. The NK cell binding molecule may comprise at least the CDRs of varlilumab. In another embodiment, the NK cell binding molecule may compete for binding with varlilumab. In another embodiment, the NK cell binding molecule may bind the same epitope as varlilumab.

The varlilumab (1F5, CDX-1127) may be as described in WO2011130434 (Celldex Therapeutics Inc.); and Vitale et al (Clinical Cancer Research 18: pp 3812-3821), both of which are incorporated herein by reference.

The NK cell binding molecule may comprise the variable heavy chain domain sequence of:

```
                                            (SEQ ID NO: 11)
QVQLVESGGGVVQPGRSLRLSCAASGFTFSSYDMHWVRQAPGKGLEWVAV
IWYDGSNKYYADSVKGRFTISRDNSKNTLYLQMNSLRAEDTAVYYCARGS
GNWGFFDYWGQGTLVTVSS (varlilumab 1F5 VH sequence),
``` or a variant thereof. Additionally, or alternatively, the NK cell binding molecule may comprise the variable light chain domain sequence of:

```
                                            (SEQ ID NO: 12)
DIQMTQSPSSLSASVGDRVTITCRASQGISRWLAWYQQKPEKAPKSLIYA
ASSLQSGVPSRFSGSGSGTDFTLTISSLQPEDFATYYCQQYNTYPRTFGQ
GTKVEIK (varlilumab 1F5 VL sequence),
``` or a variant thereof.

In one embodiment, the NK cell binding molecule may comprise CDRs of the following sequences:

```
VH CDR1:
                                            (SEQ ID NO: 13)
    GFTFSSYD;

VH CDR2:
                                            (SEQ ID NO: 14)
    IWYDGSNK;

VH CDR3:
                                            (SEQ ID NO: 15)
    ARGSGNWGFFDY;

VL CDR1:
                                            (SEQ ID NO: 16)
    QGISRW;

VL CDR2:
    AAS;
    and

VL CDR3:
                                            (SEQ ID NO: 17)
    QQYNTYPRT (i.e. varlilumab CDRs).
```

In another embodiment, the NK cell binding molecule may comprise any one of the anti-CD27 antibodies, or fragments thereof, described in WO2011130434, which is herein incorporated by reference. For example, the NK cell binding molecule may comprise at lease the CDRs, or at least the heavy and light chain variable regions of the anti-CD27 antibodies described in WO2011130434.

The NK cell binding molecule may comprise a sequence having at least 90%, 95%, 98%, or 99% identity to varlilumab. Reference to the 90%, 95%, or 99% identity may be to the framework regions of the VH and/or VL domains. In particular, the CDR regions may be identical, but the framework regions may vary by up to 1%, 5%, or 10%. Such binding molecule may differ from the sequences of varlilumab by a small number of functionally inconsequential amino acid substitutions (e.g., conservative substitutions), deletions, or insertions.

The NK and T-cell binding molecule may be capable of binding to a T-cell surface receptor/marker with at least nanomolar affinity. For example at least 100 nM affinity, at least 10 nM affinity, or at least 1 nM affinity. In another embodiment, the NK and T-cell binding molecule may be capable of binding to a T-cell surface receptor/marker with at least picomolar affinity. For example at least 100 pM affinity, or less such as at least 50 pM affinity.

In another embodiment of the invention, the NK cell and optionally T-cell binding molecule is fully human monoclonal antibody of the IgG2 or IgG4 isotype. These isotype have reduced killing potential but potentially increased agonistic activity in comparison with other isotypes, which may lead to increased efficacy.

The B-cell binding molecule and the NK cell (and optionally T-cell) binding molecule may be the same molecule in the form of a bispecific antibody, which provides both binding functions.

By "antibody" we include substantially intact antibody molecules, as well as chimeric antibodies, human antibodies, humanised antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same. In particular, the term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to as a "mAb".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, incorporated herein by reference. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023, incorporated herein by reference. A humanised antibody may be a modified antibody having the variable regions of a non-human, e.g., murine, antibody and the constant region of a human antibody. Methods for making humanised antibodies are described in, for example, U.S. Pat. No. 5,225,539, incorporated herein by reference.

The antibodies of the present disclosure may be intact or engineered For example, the antibody may be fully or partially glycosylated and/or selected for increased or diminished binding to human effector systems such as complement, FcR-bearing effectors, such as macrophages, or to extend or reduce half-life. These modifications can be made to improve effectiveness and potentially also reduce toxic side effects.

It has been shown that fragments of a whole antibody can perform the function of binding antigens. Examples of binding fragments of the invention are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site; (viii) bispecific single chain Fv dimers (PCT/US92/09965, incorporated herein by reference) and; (ix) "diabodies", multivalent or multispecific fragments constructed by gene fusion (WO94/13804, incorporated herein by reference).

Diabodies are multimers of polypeptides, each polypeptide comprising a first domain comprising a binding region of an immunoglobulin light chain and a second domain comprising a binding region of an immunoglobulin heavy chain, the two domains being linked (e.g., by a peptide linker) but unable to associated with each other to form an antigen binding site: antigen binding sites are formed by the association of the first domain of one polypeptide within the multimer with the second domain of another polypeptide within the multimer (WO94/13804, incorporated herein by reference).

The determination of percent identity between two sequences can be accomplished using a mathematical algorithm known to those of skill in the art. An example of a mathematical algorithm for comparing two sequences is the algorithm of Karlin and Altschul (Proc Natl Acad Sci USA. 1990 March; 87(6):2264-8), modified as in Karlin and Altschul (Proc Natl Acad Sci USA. 1993 Jun. 15; 90(12): 5873-7). The NBLAST and XBLAST programs of Altschul et al. have incorporated such an algorithm, and may be used under standard parameters.

The administration of the B-cell binding molecule and the immunostimulatory agent may be sequential. Alternatively, the administration of the B-cell binding molecule and the immunostimulatory agent may be concurrent.

The B-cell binding molecule and the immunostimulatory agent may be administered within one day of each other. The B-cell binding molecule and the immunostimulatory agent may be administered within 48 hours of each other. The B-cell binding molecule and the immunostimulatory agent may be administered within 35 hours of each other. The B-cell binding molecule and the immunostimulatory agent may be administered within 30 hours of each other. The B-cell binding molecule and the immunostimulatory agent may be administered within 24 hours of each other. The B-cell binding molecule and the immunostimulatory agent may be administered within 16 hours of each other. The B-cell binding molecule and the immunostimulatory agent may be administered within 12 hours of each other. The B-cell binding molecule and the immunostimulatory agent may be administered within 8 hours of each other. The B-cell binding molecule and the immunostimulatory agent may be administered within 6 hours of each other. The B-cell binding molecule and the immunostimulatory agent may be administered within 1 hour of each other.

Where separate administration occurs, the B-cell binding molecule and the immunostimulatory agent may be administered at least 1 hour apart. The B-cell binding molecule and the immunostimulatory agent may be administered at least 4 hours apart. The B-cell binding molecule and the immunostimulatory agent may be administered at least 8 hours apart. The B-cell binding molecule and the immunostimulatory agent may be administered at least 12 hours apart. The B-cell binding molecule and the immunostimulatory agent may be administered at least 18 hours apart. The B-cell binding molecule and the immunostimulatory agent may be administered at least 24 hours apart.

The B-cell binding molecule and the immunostimulatory agent may be administered between about 4 hours and about 48 hours apart. The B-cell binding molecule and the immunostimulatory agent may be administered between about 8 hours and about 48 hours apart. The B-cell binding molecule and the immunostimulatory agent may be administered between about 12 hours and about 48 hours apart. The B-cell binding molecule and the immunostimulatory agent may be administered between about 4 hours and about 30 hours apart. The B-cell binding molecule and the immunostimulatory agent may be administered between about 4 hours and about 24 hours apart. The B-cell binding molecule and the immunostimulatory agent may be administered between about 8 hours and about 30 hours apart. The B-cell binding molecule and the immunostimulatory agent may be administered between about 8 hours and about 24 hours apart. The B-cell binding molecule and the immunostimulatory agent may be administered between about 12 hours and about 30 hours apart. The B-cell binding molecule and the immunostimulatory agent may be administered between about 12 hours and about 24 hours apart. The B-cell binding molecule and the immunostimulatory agent may be administered between about 18 hours and about 30 hours apart. The B-cell binding molecule and the immunostimulatory agent may be administered about 24 hours apart.

Where separate administration occurs, the B-cell binding molecule may be administered before the immunostimulatory agent.

Delayed dosing can be advantageous in order to allow initial priming of the immune effector cells as well as further upregulation of CD27 expression on effector lymphocytes such as NK cells and T cells before addition of the B-cell binding molecule, such as an anti-CD20 mAb.

The B-cell binding molecule and/or the immunostimulatory agent may be provided in a composition. The B-cell binding molecule and/or the immunostimulatory agent may optionally be administered in combination with another therapeutically active agent. Other therapeutically active agents may comprise other immune adjuvants such as lymphokines and cytokines. Examples include interferons such as alpha, beta, and gamma interferon, interleukins such as IL-2, Il-4, IL-6, IL-13 et al., colony stimulating factors, TNFs, and the like. Other therapeutically active agents may comprise other antitumor agents such as chemotherapeutics and cytotoxins commonly used for treating cancer, agents that inhibit angiogenesis, and the like. These additional therapeutic agents may be administered separately or in combination. These additional therapeutic agents may be co-formulated with the B-cell binding molecule and/or the immunostimulatory agent.

The B-cell binding molecule and/or the immunostimulatory agent can be administered locally or systemically by any method known in the art including but not limited to intramuscular, intravenous, intradermal, subcutaneous, intraperitoneal, intranasal, oral or other mucosal routes. Additional routes include intracranial (for example intracisternal, or intraventricular), intraorbital, ophthalmic, intracapsular and intraspinal administration. It is envisaged that injections will be the primary route for therapeutic administration of the compositions although delivery through a catheter or other surgical tubing is also used. Some suitable routes of administration include intravenous, subcutaneous, intraperitoneal and intramuscular administration. Liquid formulations may be utilised after reconstitution from powder formulations.

The B-cell binding molecule and/or the immunostimulatory agent of the present invention will usually be administered in the form of a pharmaceutical composition, which may comprise at least one component in addition to the B-cell binding molecule and/or the immunostimulatory agent. The B-cell binding molecule and/or the immunostimulatory agent can be administered in a suitable, nontoxic pharmaceutical carrier, or can be formulated in microcapsules or a sustained release implant. The B-cell binding molecule and/or the immunostimulatory agent can be administered multiple times, if desired. The appropriate route, formulation, and immunization schedule can be determined by one skilled in the art.

In some instances, it may be beneficial to include a moiety on the the B-cell binding molecule and/or the immunostimulatory agent which facilitates affinity purification. Such moieties include relatively small molecules that do not interfere with the function. Alternatively, a tag may be provided, which is removable by cleavage. Examples of such tags include poly-histidine tags, hemagglutinin tags, maltase binding protein, lectins, glutathione-S transferase, avidin and the like. Other suitable affinity tags include FLAG, green fluorescent protein (GFP), myc, and the like.

The B-cell binding molecule and/or the immunostimulatory agent can be administered with a physiologically acceptable carrier such as physiological saline. The composition may also include another carrier or excipient such as buffers, such as citrate, phosphate, acetate, and bicarbonate, amino acids, urea, alcohols, ascorbic acid, phospholipids, proteins such as serum albumin, ethylenediamine tetraacetic acid, sodium chloride or other salts, liposomes, mannitol, sorbitol, glycerol and the like. The B-cell binding molecule and/or the immunostimulatory agent can be formulated in various ways, according to the corresponding route of administration.

The B-cell binding molecule and/or the immunostimulatory agent, or otherwise compositions of the invention, are preferably administered to an individual in a "therapeutically effective amount", this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of existing tumours, especially cancer, and in the prevention of the recurrence of such conditions after initial treatment or surgery. Examples of the techniques and protocols mentioned above can be found in Remington's Pharmaceutical Sciences, 16th edition, Oslo, A. (ed), 1980.

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m2 of antibody provides a serum concentration of approximately 20 nM for approximately eight days.

The dose of the B-cell binding molecule and/or the immunostimulatory agent will be dependent upon the properties of the B-cell binding molecule and/or the immunostimulatory agent, e.g., the binding activity and in vivo plasma half-life, the concentration in the formulation, the administration route, the site and rate of dosage, the clinical tolerance of the patient involved, the pathological condition afflicting the patient and the like, as is well within the skill of the physician. For example, doses of 300 μg of antibody per patient per administration are preferred, although dosages may range from about 10 μg to 6 mg per dose.

The B-cell binding molecule may be capable of killing 50% of a B-cell population in a phagocytosis assay/model when used alone (i.e. not in combination with the immunostimulatory agent). Ref Lim et al Blood 2011; 118(9); 2530-2540) In one embodiment, the promotion of killing of the B-cell comprises promoting ADCP (Antibody-Dependent Cell-mediated Phagocytosis) killing of the B-cell.

The stimulation of NK and/or T cells may result in the release of myeloid cell chemo-attractants and/or activators, such as cytokines. The released cytokines may promote myeloid infiltration of the tumour site. The released cytokines may be chemokines capable of promoting myeloid cell chemotaxis. Therefore, in one embodiment, the stimulation of effector lymphocytes cell activation may promote myeloid infiltration of the tumour site.

The stimulation/activation may comprise at least a 3-fold increase in IFN gamma release. Ref Takeda J Immunol 2000; 164:1741-1745. The immunostimulatory agent arranged to stimulate NK and/or T-cell activation may be capable of causing a 3-fold increase in cytokine release in an in vitro murine assay/model when used alone (i.e. not in combination with the B-cell binding molecule). The stimulation of NK and/or T-cell activation may increase myeloid chemotaxis/activation/infiltration in the BCL1 model.

The combination of the binding molecule capable of binding to a B-cell and promoting killing of the B-cell and the immunostimulatory agent arranged to stimulate NK and/or T-cell activation may facilitate the 100%/100 days survival of treated mice in BCL1 mouse model.

The skilled person will understand that "NK cell activation" "T cell activation" and "myeloid cell infiltration" may be readily determined by detection of known activation markers on such cells.

According to another aspect of the invention, there is provided a method of treatment or prevention of B-cell related disease in a subject comprising the administration of an anti-CD20 binding molecule and an anti-CD27 binding molecule to the subject.

The anti-CD20 binding molecule may comprise rituximab, or similar. The anti-CD27 binding molecule may comprise varlilumab, or similar.

According to another aspect of the invention, there is provided a method of treatment or prevention of B-cell related disease in a subject comprising the administration of rituximab and varlilumab to the subject.

The administration may be concurrent, such as co-formulated or in immediate, but separate administrations. Alternatively, the administration may be sequential, for example, one before the other. The sequential administration may be within hours or days. For example, one agent may be delivered about a day after the other agent. The anti-CD20 binding molecule, such as rituximab, may be administered before the anti-CD27 binding molecule, such as varlilumab.

The administration may be a therapeutically effective amount.

According to another aspect of the invention, there is provided an anti-CD27 binding agent for use in a combination therapy with an anti-CD20 binding agent for the treatment or prevention of B-cell related disease in a subject.

According to another aspect of the invention, there is provided a bispecific antibody or variant thereof comprising a CD20 binding domain and a CD27 binding domain.

According to another aspect of the invention, there is provided a composition comprising an anti-CD20 binding agent and an anti-CD27 binding agent.

According to another aspect of the invention, there is provided a kit for treatment or prevention of B-cell related disease in a subject, the kit comprising an anti-CD20 binding agent and an anti-CD27 binding agent.

The anti-CD20 binding agent and anti-CD27 binding agent of the kit may be co-formulated in the same composition or separately formulated in separate compositions. Alternatively, the anti-CD20 binding agent and anti-CD27 binding agent may be the same agent, where the anti-CD20 and anti-CD27 functions are provided in the form of a bispecific antibody.

According to another aspect of the invention, there is provided a composition according to the invention for use as a medicament.

According to another aspect of the invention, there is provided a composition according to the invention, or kit according to the invention, for use in the treatment or prevention of B-cell related disease in a subject.

The prevention of B-cell related disease in a subject may be for a subject who has previously had treatment for B-cell related disease but is in remission.

According to another aspect of the invention there is provided a method of treatment or prevention of cancer in a subject comprising the administration of a cancer-cell-depleting binding agent capable of binding to the cancer cell and promoting killing of the cancer cell; and an immunostimulatory agent arranged to stimulate NK and/or T-cell activation.

Advantageously, the invention recognises that the mechanism of action of a binding agent, such as an antibody, that can directly kill a cancer cell can be enhanced by increased myeloid cell infiltration into the cancer site via immunostimulatory agent arranged to stimulate NK and/or T-cell activation.

According to another aspect of the invention, there is provided an anti-CD27 binding agent for use in a combination therapy with a cancer-cell-depleting binding agent for the treatment or prevention of cancer in a subject.

In one embodiment, the cancer to be treated or prevented may comprise a solid tumour malignancy. The cancer cell may comprise or consist of a cancer cell of a solid tumour. The solid tumour may comprise a sarcoma, carcinoma, or lymphoma. The cancer may comprise neuroblastoma or melanoma. Solid tumors that can be treated using the compositions and methods described herein may be selected from any one of the group of solid tumors of the breast, lung, colon, stomach, liver, kidney, ovary, and prostate; or combinations thereof. Tumors that can be treated in accordance with the invention may be selected from breast carcinomas, lung carcinomas, prostate carcinomas, gastric carcinomas, esophageal carcinomas, colorectal carcinomas, liver carcinomas, ovarian carcinomas, vulval carcinomas, kidney carcinomas, cervical carcinomas, endometrial carcinoma, endometrial hyperplasia, endometriosis, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreatic carcinomas, retinoblastoma, astrocytoma, glioblastoma, Schwannoma, oligodendroglioma, medulloblastoma, neuroblastomas, sarcomas include fibrosarcomas, rhabdomyosarcoma, osteogenic sarcoma, leiomyosarcomas, urinary tract carcinomas, thyroid carcinomas, Wilm's tumor, brain tumors, renal cell carcinomas, abnormal vascular proliferation associated with phakomatoses, and edema (such as that associated with brain tumors); or combinations thereof. The cancer cell may comprise a cell of any one of the above solid tumours.

The cancer-cell-depleting binding agent may be any agent, such as an antibody, that is capable of binding to the cancer cell and effecting killing of that cell. For example, through augmented antibody direct cellular cytotoxicity/phagocytosis (ADCC/ADCP). The cancer-cell-depleting binding agent may be capable of causing apoptosis or lysis of the cancer cell. The cancer-cell-depleting binding agent may comprise any one of the B-cell binding molecules described herein. The cancer-cell-depleting binding agent may be any one of an anti-HER2 binding molecule; anti-MUC1 binding molecule; anti-EGFR binding molecule; anti-CD52 binding molecule; anti-CD38 binding molecule; or anti-GD2 binding molecule. The cancer-cell-depleting binding agent may comprise any one of trastuzumab (typically used in HER2/neu positive breast cancer); cetuximab (typically used in colorectal cancer, non-small cell lung cancer and head and neck cancer); dinutuximab (typically used in neuroblastoma); daratumumab (typically used in multiple myeloma; or alemtuzumab (typically used in T-cell malignancies).

In another embodiment, the cancer-cell-depleting binding agent may comprise a biosimilar of trastuzumab, cetuximab, dinutuximab, daratumumab, or alemtuzumab. The B-cell binding molecule may comprise at least a variable domain of trastuzumab, cetuximab, dinutuximab, daratumumab, or alemtuzumab. The B-cell binding molecule may comprise at least the CDRs of trastuzumab, cetuximab, dinutuximab, daratumumab, or alemtuzumab. In another embodiment, the B-cell binding molecule may compete for binding with trastuzumab, cetuximab, dinutuximab, daratumumab, or alemtuzumab. In another embodiment, the B-cell binding molecule may bind the same epitope as trastuzumab, cetuximab, dinutuximab, daratumumab, or alemtuzumab.

In another embodiment, the cancer-cell-depleting binding agent may comprise and anti-gp75 binding agent. The anti-gp75 binding agent may comprise an antibody, antibody fragment, or mimetic thereof. The anti-gp75 binding agent may comprise the monoclonal antibody TA99.

TA99 is an anti-gp75 (TYRP1/TRP1) binding antibody described in (available for purchase, for example from Bio X Cell, 10 Technology Dr., Suite 2B, West Lebanon, NH 03784-1671 USA (https://bxcell.com/product/trp-1-gp75/— Catalog #: BE0151-MAb anti-mouse/human TYRP1/TRP1 (gp75) (Clone: TA99). Also described in Lehmann, B., et al. (2017). Sci Immunol 2(7): 10.1126/sciimmunol.aah6413; Dennis, M. K., et al. (2015). J Cell Biol 209(4): 563-577; Duval, C., et al. (2014). PLoS One 9(12): e114182; Ly, L. V., et al. (2013). J Immunol 190(1): 489-496; and Boross et al. Immunology Letters. Volume 160, Issue 2, August 2014, Pages 151-157, which are herein incorporated by reference.

In another embodiment, the anti-gp75 binding agent may comprise an antibody comprising the heavy and light variable chain of the monoclonal antibody TA99. In another embodiment, the anti-gp75 binding agent may comprise an antibody comprising the HCDRs and LCDRs of the monoclonal antibody TA99.

For example, TA99 heavy chain variable sequence may comprise the sequence:

(SEQ ID NO: 18)
EVQLQQSGAELVRPGALVKLSCKTSGFNIKDYFLHWVRQRPDQGLEWIGW
INPDNGNTVYDPKFQGTASLTADTSSNTVYLQLSGLTSEDTAVYFCTRRD
YTYEKAALDYWGQGTTVTVST.

The TA99 light chain variable sequence may comprise the sequence:

(SEQ ID NO: 19)
IQMSQSPASLSASVGETVTITCRASGNIYNYLAWYQQKQGKSPHLLVYDA
KTLADGVPSRFSGSGSGTQYSLKISSLQTEDSGNYYCQHFWSLPFTFGSG
TKLEIKR.

In another embodiment, the anti-gp75 binding agent may comprise an antibody that competes for binding with monoclonal antibody TA99. In another embodiment, the anti-gp75 binding agent may comprise an antibody that binds the same epitope as monoclonal antibody TA99. The anti-gp75 binding agent may comprise a biosimilar or enhanced equivalent of TA99, such as the anti-tyrp1 antibodies described in WO2009114585A1, which is herein incorporated by reference.

The anti-gp75 binding agent in combination with the immunostimulatory agent, such as an anti-CD27 binding agent may be particularly used or useful for the treatment or prevention of melanoma.

According to another aspect of the invention, there is provided a composition for treatment or prevention of cancer in a subject, the composition comprising a cancer-cell-depleting binding agent and an immunostimulatory agent, such as an anti-CD27 binding agent.

According to another aspect of the invention, there is provided a kit for treatment or prevention of cancer, such as a solid tumour, in a subject, the kit comprising a cancer-cell-depleting binding agent and an anti-CD27 binding agent.

According to another aspect of the invention, there is provided a composition according to the invention, or kit according to the invention, for use in the treatment or prevention of cancer, such as a solid tumour.

The administration of the cancer-cell-depleting binding agent and the immunostimulatory agent may be sequential. Alternatively, the administration of the cancer-cell-depleting binding agent and the immunostimulatory agent may be concurrent.

The cancer-cell-depleting binding agent and the immunostimulatory agent may be administered within one day of each other. The cancer-cell-depleting binding agent and the immunostimulatory agent may be administered within 48 hours of each other. The B-cell binding molecule and the immunostimulatory agent may be administered within 35 hours of each other. The cancer-cell-depleting binding agent and the immunostimulatory agent may be administered within 30 hours of each other. The cancer-cell-depleting binding agent and the immunostimulatory agent may be administered within 24 hours of each other. The cancer-cell-depleting binding agent and the immunostimulatory agent may be administered within 16 hours of each other. The cancer-cell-depleting binding agent and the immunostimulatory agent may be administered within 12 hours of each other. The cancer-cell-depleting binding agent and the immunostimulatory agent may be administered within 8 hours of each other. The cancer-cell-depleting binding agent and the immunostimulatory agent may be administered within 6 hours of each other. The cancer-cell-depleting binding agent and the immunostimulatory agent may be administered within 1 hour of each other.

Where separate administration occurs, the cancer-cell-depleting binding agent and the immunostimulatory agent may be administered at least 1 hour apart. The cancer-cell-depleting binding agent and the immunostimulatory agent may be administered at least 4 hours apart. The cancer-celldepleting binding agent and the immunostimulatory agent may be administered at least 8 hours apart. The cancer-cell-depleting binding agent and the immunostimulatory agent may be administered at least 12 hours apart. The cancer-cell-depleting binding agent and the immunostimulatory agent may be administered at least 18 hours apart. The cancer-cell-depleting binding agent and the immunostimulatory agent may be administered at least 24 hours apart.

The cancer-cell-depleting binding agent and the immunostimulatory agent may be administered between about 4 hours and about 48 hours apart. The cancer-cell-depleting binding agent and the immunostimulatory agent may be administered between about 8 hours and about 48 hours apart. The cancer-cell-depleting binding agent and the immunostimulatory agent may be administered between about 12 hours and about 48 hours apart. The cancer-cell-depleting binding agent and the immunostimulatory agent may be administered between about 4 hours and about 30 hours apart. The cancer-cell-depleting binding agent and the immunostimulatory agent may be administered between about 4 hours and about 24 hours apart. The cancer-cell-depleting binding agent and the immunostimulatory agent may be administered between about 8 hours and about 30 hours apart. The cancer-cell-depleting binding agent and the immunostimulatory agent may be administered between about 8 hours and about 24 hours apart. The cancer-cell-depleting binding agent and the immunostimulatory agent may be administered between about 12 hours and about 30 hours apart. The cancer-cell-depleting binding agent and the immunostimulatory agent may be administered between about 12 hours and about 24 hours apart. The cancer-cell-depleting binding agent and the immunostimulatory agent may be administered between about 18 hours and about 30 hours apart. The cancer-cell-depleting binding agent and the immunostimulatory agent may be administered about 24 hours apart.

Where separate administration occurs, the cancer-cell-depleting binding agent may be administered before the immunostimulatory agent.

Delayed dosing can be advantageous in order to allow initial priming of the immune effector cells as well as further upregulation of CD27 expression on NK and/or T-cells before addition of the B-cell binding molecule, such as an anti-CD20 mAb.

The cancer-cell-depleting binding agent and/or the immunostimulatory agent may optionally be administered in combination with another therapeutically active agent. Other therapeutically active agents may comprise other immune adjuvants such as lymphokines and cytokines. Examples include interferons such as alpha, beta, and gamma interferon, interleukins such as IL-2, Il-4, IL-6, IL-13 et al., colony stimulating factors, TNFs, and the like. Other therapeutically active agents may comprise other antitumor agents such as chemotherapeutics and cytotoxins commonly used for treating cancer, agents that inhibit angiogenesis, and the like. These additional therapeutic agents may be administered separately or in combination. These additional therapeutic agents may be co-formulated with the cancer-cell-depleting binding agent and/or the immunostimulatory agent.

The cancer-cell-depleting binding agent and/or the immunostimulatory agent can be administered locally or systemically by any method known in the art including but not limited to intramuscular, intravenous, intradermal, subcutaneous, intraperitoneal, intranasal, oral or other mucosal routes. Additional routes include intracranial (for example intracisternal, or intraventricular), intraorbital, ophthalmic, intracapsular and intraspinal administration. It is envisaged that injections will be the primary route for therapeutic administration of the compositions although delivery through a catheter or other surgical tubing is also used. Some suitable routes of administration include intravenous, subcutaneous, intraperitoneal and intramuscular administration. Liquid formulations may be utilised after reconstitution from powder formulations.

The cancer-cell-depleting binding agent and/or the immunostimulatory agent of the present invention will usually be administered in the form of a pharmaceutical composition, which may comprise at least one component in addition to the cancer-cell-depleting binding agent and/or the immunostimulatory agent. The cancer-cell-depleting binding agent and/or the immunostimulatory agent can be administered in a suitable, nontoxic pharmaceutical carrier, or can be formulated in microcapsules or a sustained release implant. The cancer-cell-depleting binding agent and/or the immunostimulatory agent can be administered multiple times, if desired. The appropriate route, formulation, and immunization schedule can be determined by one skilled in the art.

In some instances, it may be beneficial to include a moiety on the the cancer-cell-depleting binding agent and/or the immunostimulatory agent which facilitates affinity purification. Such moieties include relatively small molecules that do not interfere with the function. Alternatively, a tag may be provided, which is removable by cleavage. Examples of such tags include poly-histidine tags, hemagglutinin tags, maltase binding protein, lectins, glutathione-S transferase, avidin and the like. Other suitable affinity tags include FLAG, green fluorescent protein (GFP), myc, and the like.

The cancer-cell-depleting binding agent and/or the immunostimulatory agent can be administered with a physiologically acceptable carrier such as physiological saline. The composition may also include another carrier or excipient such as buffers, such as citrate, phosphate, acetate, and bicarbonate, amino acids, urea, alcohols, ascorbic acid, phospholipids, proteins such as serum albumin, ethylenediamine tetraacetic acid, sodium chloride or other salts, liposomes, mannitol, sorbitol, glycerol and the like. The cancer-cell-depleting binding agent and/or the immunostimulatory agent can be formulated in various ways, according to the corresponding route of administration.

The cancer-cell-depleting binding agent and/or the immunostimulatory agent, or otherwise compositions of the invention, are preferably administered to an individual in a "therapeutically effective amount", this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of existing tumours, especially cancer, and in the prevention of the recurrence of such conditions after initial treatment or surgery. Examples of the techniques and protocols mentioned above can be found in Remington's Pharmaceutical Sciences, 16th edition, Oslo, A. (ed), 1980.

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m2 of antibody provides a serum concentration of approximately 20 nM for approximately eight days.

The dose of the cancer-cell-depleting binding agent and/or the immunostimulatory agent will be dependent upon the properties of the cancer-cell-depleting binding agent and/or the immunostimulatory agent, e.g., the binding activity and in vivo plasma half-life, the concentration in the formulation, the administration route, the site and rate of dosage, the clinical tolerance of the patient involved, the pathological condition afflicting the patient and the like, as is well within the skill of the physician. For example, doses of 300 µg of antibody per patient per administration are preferred, although dosages may range from about 10 µg to 6 mg per dose.

Reference to binding may be specific binding. "specific binding" or "specifically binding" is generally used to refer to the situation in which the binding molecule will not show any significant binding to molecules other than its specific binding partner(s)/epitope, and, e.g., has less than about 30%, preferably 20%, 10%, or 1% cross reactivity with any other molecule.

The term "subject" means all animals including humans. Examples of subjects include humans, cows, dogs, cats, goats, sheep, and pigs. The term "patient" means a subject having a disorder in need of treatment.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

The skilled man will appreciate that preferred features of any one embodiment and/or aspect of the invention may be applied to all other embodiments and/or aspects of the invention.

Examples embodying an aspect of the invention will now be described with reference to the following figures:

FIG. 1. Anti-CD27 enhances anti-CD20 therapy in primary murine B-cell lymphomas. A) The line diagram illustrates the experimental model employed. 10,000 $BCL_1$ tumour cells were injected into the tail vein of Balb/c mice on D0. 200 µg 18B12 mouse IgG2a or control was given on D4 and 50-100 µg AT124-1 rat IgG2a or control was given daily from D5 to D8. All mAbs were administered by i.p. injection. The survival of the mice was then monitored by spleen palpation. Mice were sacked when the spleen was 3 to 3.5 cm below the costal margin.

B) As described in A, $BCL_1$-bearing mice were treated with either PBS carrier control, 18B12, AT124-1 or combined 18B12 and AT124-1. Kaplan-Meier survival curves are shown (n=5, repeated at least thrice) * p<0.05, **p<0.005. C) CBA mice were injected i.v. with 10,000 A31 lymphoma cells into the tail on D0. Treatment was initiated on D4 as described in A) (n=5), representative of 3 experiments.

FIG. 2. Anti-CD27 promotes effector memory CD8 T cell expansion.

A, B) $BCL_1$ bearing mice were treated as described in FIG. 1A). Spleens were then harvested on the days indicated and processed as described.

A) Spleens were harvested on D9 and cells analysed by flow cytometry for total CD8 T cells (CD3+CD8+), Tregs (CD3+CD8+CD25+FOXP3+) and absolute counts are shown. Each point represents a different mouse.

B) Spleens were harvested on D6 and D9 and frozen, fixed, sectioned and stained for CD8 expression and counterstained with haematoxylin. Images were collected at ×4 magnification.

FIG. 3. Anti-CD27 promotes CD8 T cell activation.

A, B) $BCL_1$ bearing mice were treated as described in FIG. 1A). Spleens were harvested on D6, D9 and D13 and analysed by flow cytometry for CD8 T cell subsets. Representative FACS plots are shown in A).

B) The graph shows the absolute cell counts of the following CD8 T cell subsets in the spleen, naïve (CD44low, CD62L−), central memory—like (CD44hi, CD62L+), effector memory-like (CD44hi, CD62L−). Each point represents a different mouse.

FIG. 4. Anti-CD27 promotes CD8 T cell memory response.

A) $BCL_1$ bearing mice were treated as described in FIG. 1A). The survivors and controls (naïve mice (no tumour) and mice bearing tumour but had not received any treatment (NT)) were peripherally bled and analysed for CD8 T cell subset %: Naïve (CD44low, CD62L−), central memory (CD44hi, CD62L+), effector memory (CD44hi, CD62L−) subsets. Each point represents a different mouse.

B) $BCL_1$ bearing mice were treated as described in FIG. 1A). The survivors were rechallenged with 10,000 $BCL_1$ cells at D110 and survival monitored by spleen palpation.

C) $BCL_1$ bearing mice were treated as described in FIG. 1A) and surviving 18B12+AT124-1 treated mice were rechallenged with 10,000 BCL1 cells at D92 and 50 µg AT124-1 daily from D5-8 post tumour rechallenge by i.p. As controls, naïve mice injected with $BCL_1$ cells simultaneously and treated with either PBS or AT124-1. **p<0.005, Naïve/AT124-1 v Rechallenged/AT124-1.

FIG. 5. Anti-CD27 promotes recruitment of myeloid immune effector cells.

A, B) $BCL_1$ bearing mice were treated as described in FIG. 1A). Spleens were then harvested on the days indicated and processed as described below.

A) Spleens were harvested on D6, D9 and D13 and cells analysed by flow cytometry for $BCL_1$ cells (anti-idiotype+), normal B cells (anti-CD19+anti-idiotype−), NK cells (CD3-NKp46+), neutrophil (CD11b+Ly6g+Ly6c−), monocyte (CD11b+Ly6g−Ly6c high) and macrophage (F4/80hi CD11b intermediate) expression. Absolute counts are shown. Each point represents a different mouse.

B) Spleens were harvested on D9 and frozen, fixed, sectioned and stained for $BCL_1$ cells (anti-idiotype), normal B cells (anti-B220), neutrophils (anti-Ly6c/Ly6g), macrophage (anti-F4/80) and monocyte (anti-CD14) expression and counterstained with haematoxylin. Images were collected at ×4 magnification.

Figure 6A:
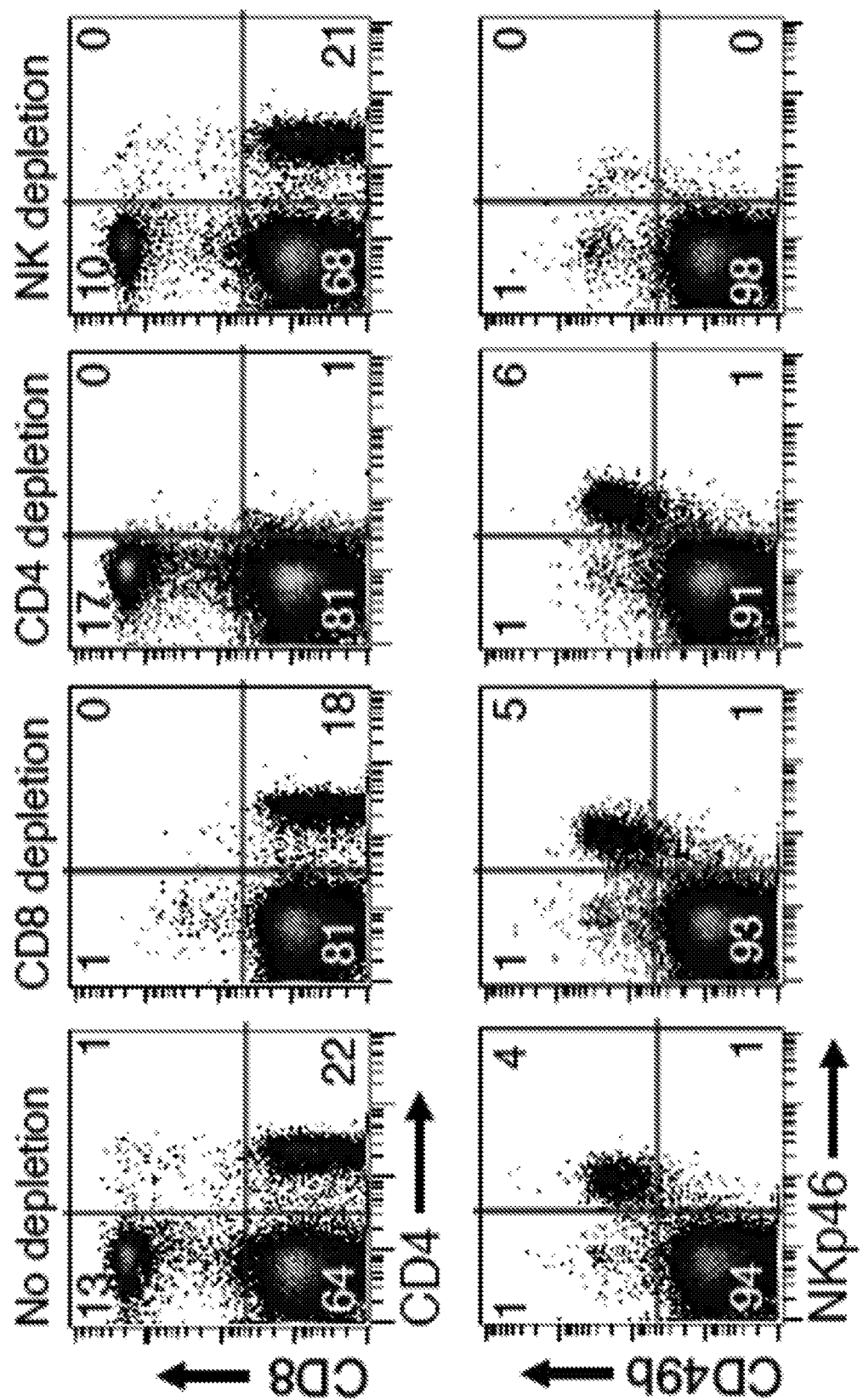

FIG. 6. Combined anti-CD20 and anti-CD27 therapy is dependent on NK cells.

A, B) Balb/c mice were treated with a PBS carrier control or depletingmAbs, anti-CD8 500 anti-CD4 1 mg, anti-asialo GM1 50 µl i.p. on D1, D3, D7, D11 and D16. 10,000 BCL1 cells were injected i.v. on D0 and treatment with PBS or 18B12 and AT124-1 commenced as before, described in FIG. 1 A).

A) One mouse from each no depletion, CD4, CD8 and NK depleted groups were sacked and blood and spleen stained for CD3, CD4, CD8, NKp46 and CD49b to check depletion efficiency. Non-cross blocking clones fluorescent and depleting anti-CD4 and anti-CD8 mAbs were used.

B) Kaplan-Meier survival curves are shown (n=5). In the combination treated arm, no depletion, CD8 and CD4 depletion survivals are superimposed and identical. *p<0.05 (Combination/no depletion v combination/NK depletion).

FIG. 7. Combined 18B12 and immunomodulatory Ab therapy in $BCL_1$ lymphoma model.

Balb/c mice received 10,000 $BCL_1$ lymphoma cells intravenously on D0 treatment was initiated with PBS control or 18B12 200 µg on D4 and A) anti-OX40 250 µg on D5 and D9, B) anti-TIGIT 200 µg on D5 every 3-4 days for 3 doses, C) anti-GITR 250 µg on D5 and D7, D) anti-PDL1 200 µg every 3-4 days for 4 doses, and E) anti-PD1 250 µg and/or anti-CTLA4 100 µg on D5 every 2 days for 3 doses.

Figure 8:
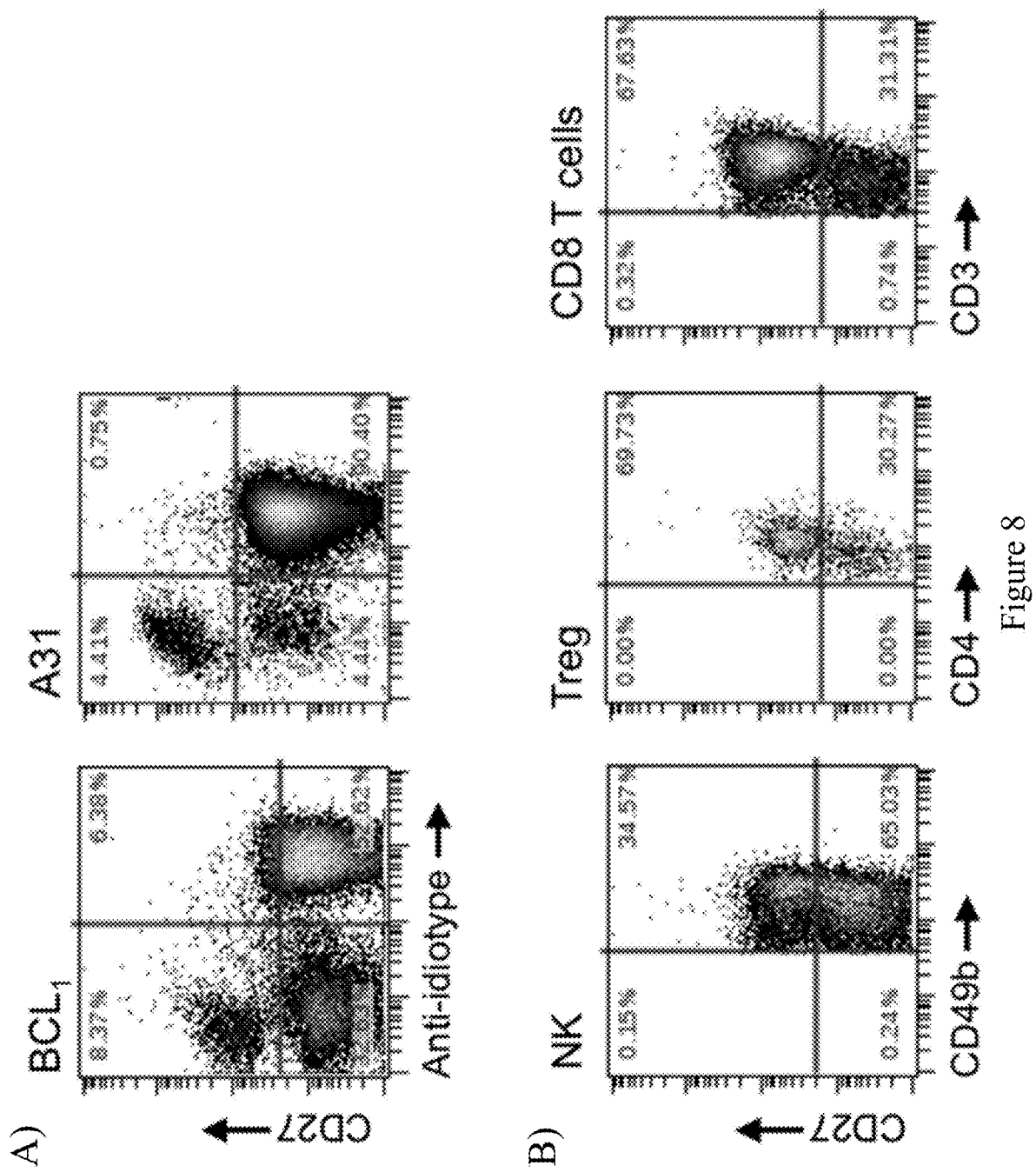

FIG. 8. Expression of CD27 on murine lymphoma immune effector cells

A) Expression of CD27 on $BCL_1$ and A31 murine lymphoma cells by flow cytometry.
B) Expression of CD27 NK cells (NKp46+CD49b+), Tregs (CD3+CD4+CD25+FOXP3+) and CD8 T cells (CD3+CD8+) cells isolated from Balb/c splenocytes.

Figure 9:
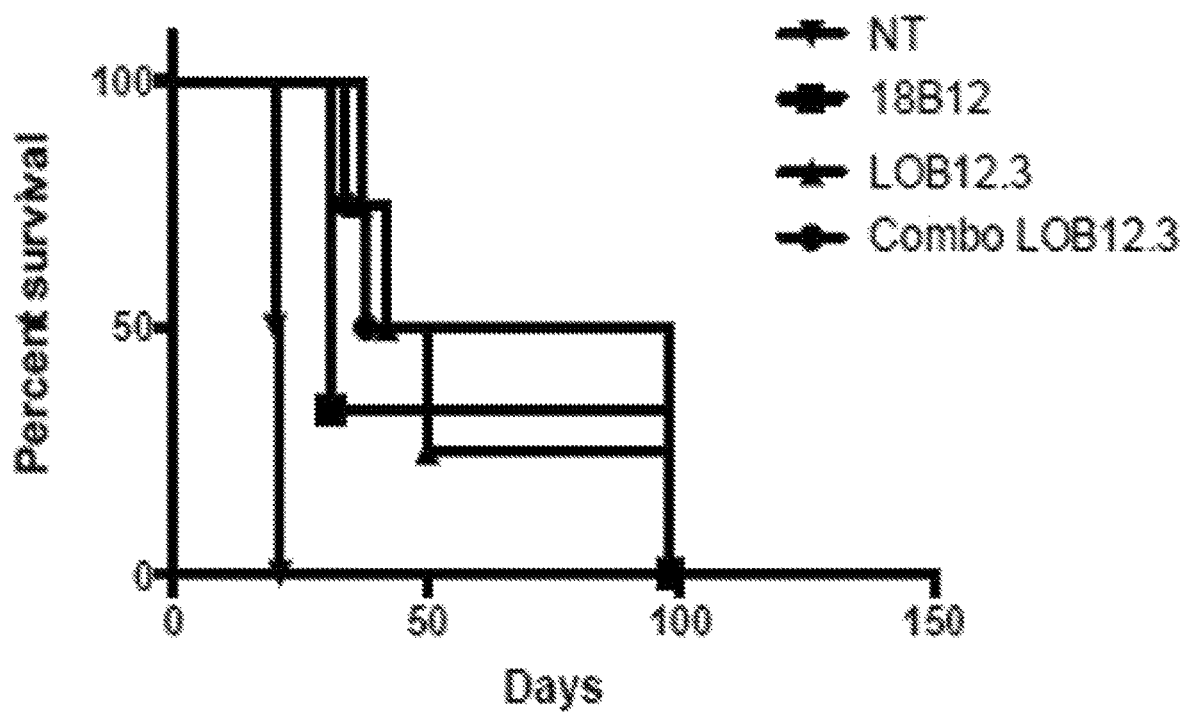

FIG. 9. Combined 18B12 and anti-CD137(4-1BB) therapy in $BCL_1$ lymphoma is ineffective.

Balb/c mice received 10,000 $BCL_1$ lymphoma cells intravenously on D0 treatment was initiated with PBS control or 18B12 200 µg on D4 and anti-CD137 (cloneLOB12.3 rIgG2a, 200 µg, IP) on D5 for 3 doses, 3-4 days apart. Survival of mice were monitored as previously described (5 mice/group).

Figure 10:
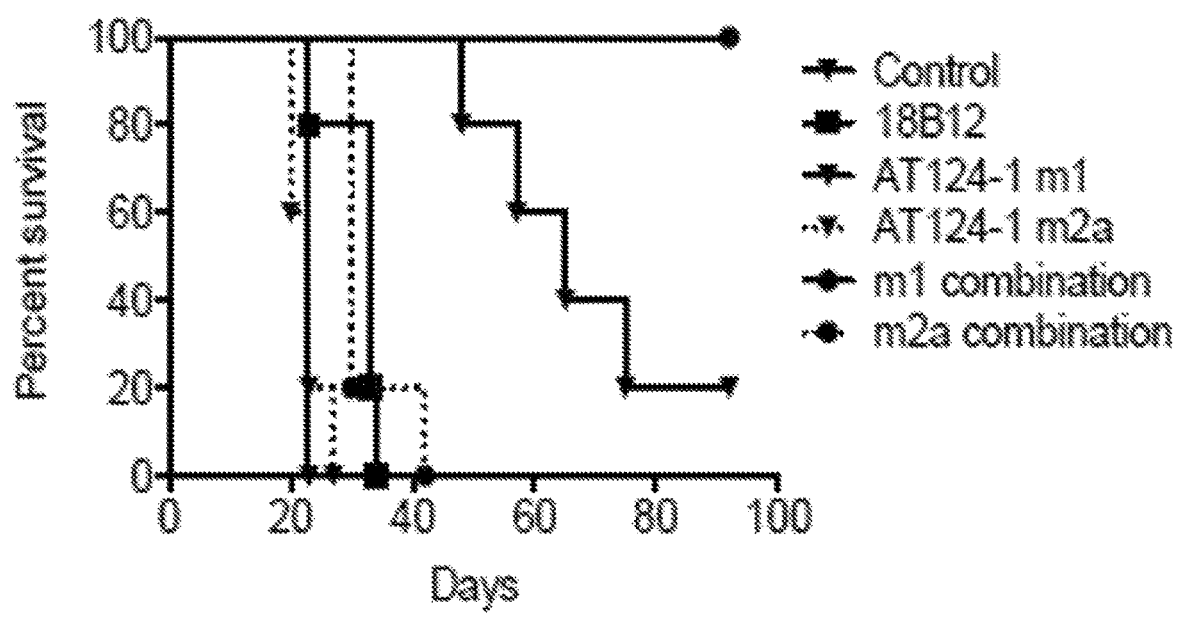

FIG. 10. Anti-CD27 therapy is affected by Ab isotype.

Balb/c mice received 10,000 $BCL_1$ lymphoma cells intravenously on D0 treatment was initiated with PBS control or 18B12 200 µg on D4 and/or 50 µg IP of AT124-1 mIg1 (AT124-1 ml) or AT124-1 mIgG2a (AT124-1 m2a) from D5-8 inclusive. Survival of mice were monitored as previously described.

FIG. 11. Combining anti-CD20 with immunomodulatory mAbs in B-cell lymphoma $BCL_1$-bearing mice were treated with isotype control, anti-CD20 on day 4 (200 µg) or combinations thereof; (A) anti-OX40 (250 µg) on days 5 and 9; (B) anti-TIGIT (200 µg) on days 5, 8 and 11; (C) anti-GITR (250 µg) on days 5 and 8; (D) anti-PD-L1 (200 µg) on days 5, 7, 9, 11 and 13; (E) anti-PD-1 (250 µg) on days 5, 7 and 9, or anti-CTLA-4 (100 µg) on days 5, 7 and 9; (F) anti-4-1BB (200 µg) on days 5, 8 and 11. Graphs show n=10 per group, compiled from two independent experiments, and *p<0.05,* *p<0.01, ns indicates not significant (Log-rank test).

FIG. 12. Anti-CD27 enhances direct tumor targeting mAb (A) $BCL_1$-bearing mice were treated with isotype control, anti-CD20 (200 µg) on day 4, anti-CD27 (100 µg) on days 5-8, or in combination. Graph shows n=15 per group, representative of three independent experiments, *p<0.001 (Log-rank test). (B) A31-bearing mice were treated with isotype control, anti-CD20 (200 µg) on days 4 and 14, anti-CD27 (100 µg) on days 5-8 and 15-18, or in combination. Graph shows n=10 per group, compiled from two independent experiments and p<0.0001(Log-rank test). (C-E) Eµ-TCL1-bearing mice were treated with anti-CD20 (250 µg) or anti-CD27 (100 µg) the next day, or the combination >3 weeks post-tumor inoculation when peripheral tumor was >10%. Graphs show n=6/group, representative of two independent experiments. Peripheral blood tumor burden and total PBMC count are shown in (D) and (E). p<0.01(Paired Student's t test). See also FIG. 18.

FIG. 13. Anti-CD27 stimulates CD8+ T cells $BCL_1$-bearing mice were treated as described in FIG. 2A and spleens harvested on day 13. Cell counts were obtained and cells stained for flow cytometry (A-C). (A) Representative flow cytometry plots demonstrate increased percentages of activated CD8+ T cells. (B) Graphs show increased $CD62L^{hi}$ CD44+ and $CD62L^{lo}$ CD44+ CD8+ T cells with anti-CD27 and anti-CD20/-CD27 therapy, n=5 per group, *p<0.05, **p<0.01, ns indicates not significant, paired Student's t test. (C) Graphs show absolute numbers of CD8+ T cells, Tregs and total CD8+/Treg ratio, n=7 per group, *p<0.05, p<0.01, *p<0.001, ns indicates not significant, paired Student's t test. (D) $BCL_1$-bearing mice were treated as in (A) and spleens harvested on day 9 and stained for CD8 by immunohistochemistry. Scale bar represents 500 (E) $BCL_1$-bearing mice were depleted of CD8+, CD4+ or both cell types, and treated as described in FIG. 2A. Graphs show n=5-10 per group, representative of two independent experiments, p<0.01, p<0.0001, ns indicates not significant (Log-rank test). (F) $BCL_1$-bearing mice were depleted of NK cells and treated as previously described with isotype control, anti-CD20, anti-CD27 or the combination. Graphs show n=5-10, from 2 independent experiments, ns indicates not significant (Log-rank test). (G) $BCL_1$-bearing mice were depleted of T and NK cells, and treated with isotype control, anti-CD20, anti-CD27, or the combination. Graphs show n=5, representative of 2 independent experiments p<0.01 (Log-rank test). See also FIG. 19.

FIG. 14. Anti-CD27 promotes intratumoral myeloid infiltration (A-F) $BCL_1$-bearing mice were treated as previously described and spleens harvested on days 9 and 13 and examined for tumor, normal B cells, NK cells, macrophages, monocytes and neutrophils. Graphs n=6-8 per group and p values were calculated using an unpaired Student's t test. *p<0.05, p<0.01, *p<0.001, ns indicates not significant. (G-I) Naïve mice were treated as in (A-F) and spleens harvested on day 13 and examined for myeloid cells (n=2-4, *p<0.05, p<0.01, *p<0.001, ns indicates not significant unpaired Student's t test). (J) $BCL_1$-bearing mice treated as in (A-F) and spleens harvested on day 9 and stained for tumor, normal B cells, macrophages, monocytes and neutrophils by immunohistochemistry. Scale bar represents 500 µm. See also FIG. 20.

FIG. 15. Anti-CD27 indirectly activates macrophages (A) Naïve mice were treated as described in FIG. 2A, spleens harvested on day 9 and RNA extracted for cytokine and chemokine profiling. The graph is a summary of the genes that are significantly upregulated over the control sample. p values were calculated using an unpaired Student's t test. *p<0.05, p<0.01, *p<0.001. See also FIG. 21. (B) Naïve mice were treated with isotype control or anti-CD27, with or without a CCL3-neutralizing mAb. Spleens were harvested and macrophages enumerated, n=4 per group from two experiments, unpaired Student's t test used, *p<0.05, ns indicates not significant. (C) CD86 and HLA-I A/E expression on macrophages, in naïve mice treated with isotype control or anti-CD27. Mean fluorescence intensity (MFI) values are shown and histograms are representative of triplicate experiments. (D) BCL$_1$-bearing mice were treated as previously described and macrophages harvested on day 13 and FcγR expression assessed. MFI values are shown and histograms are representative of triplicate experiments.

FIG. 16. Global gene expression profiling of anti-CD20 and/or anti-CD27 treated BCL$_1$-bearing mice Single cell RNA sequencing was performed on spleens harvested on day 13 from BCL$_1$-bearing mice treated as previously described. t-SNE plots are shown, with each point representing a cell. (A) t-SNE plot showing the individual immune effector subsets, assigned according to their top match with the co-expression atlas of the Immunological Genome Project. Each population is denoted by a different color and those marked with an * are proliferating. (B) Data from (A) is subdivided into the different treatment conditions to demonstrate changes in the various subsets. (C) Upregulation of CCL3 on effector CD8+ T cells and NK cells are indicated by the blue cells and red arrows (marked "A"), respectively. The yellow cells lack expression of CCL3. (D) Upregulation of Ifitm3 on granulocytes and macrophages is indicated by the black cells and green arrows (marked "B"), respectively. (E) Upregulation of Isg15 on granulocytes and macrophages is indicated by the black cells and green arrows (marked "B"), respectively. See also FIG. 22.

Figure 17:
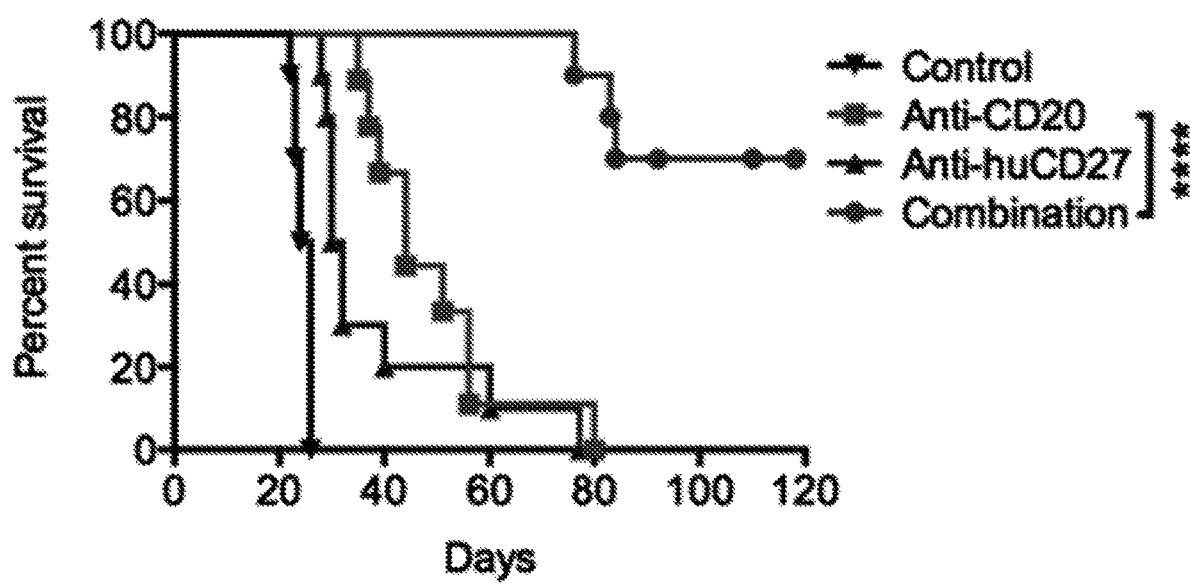

FIG. 17. In vivo and in vitro activity of anti-huCD27

Figure 2A:
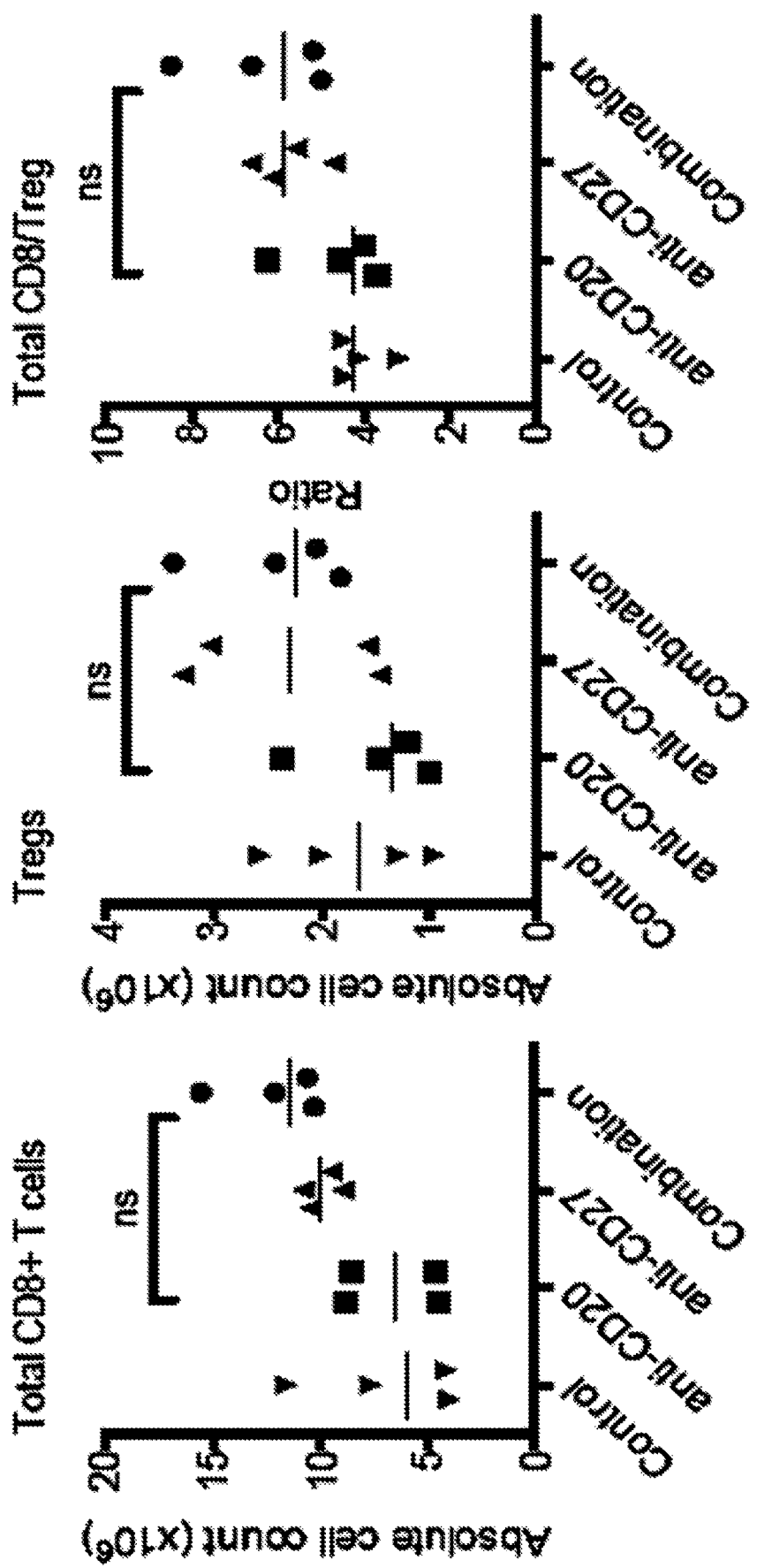
Figure 2B:
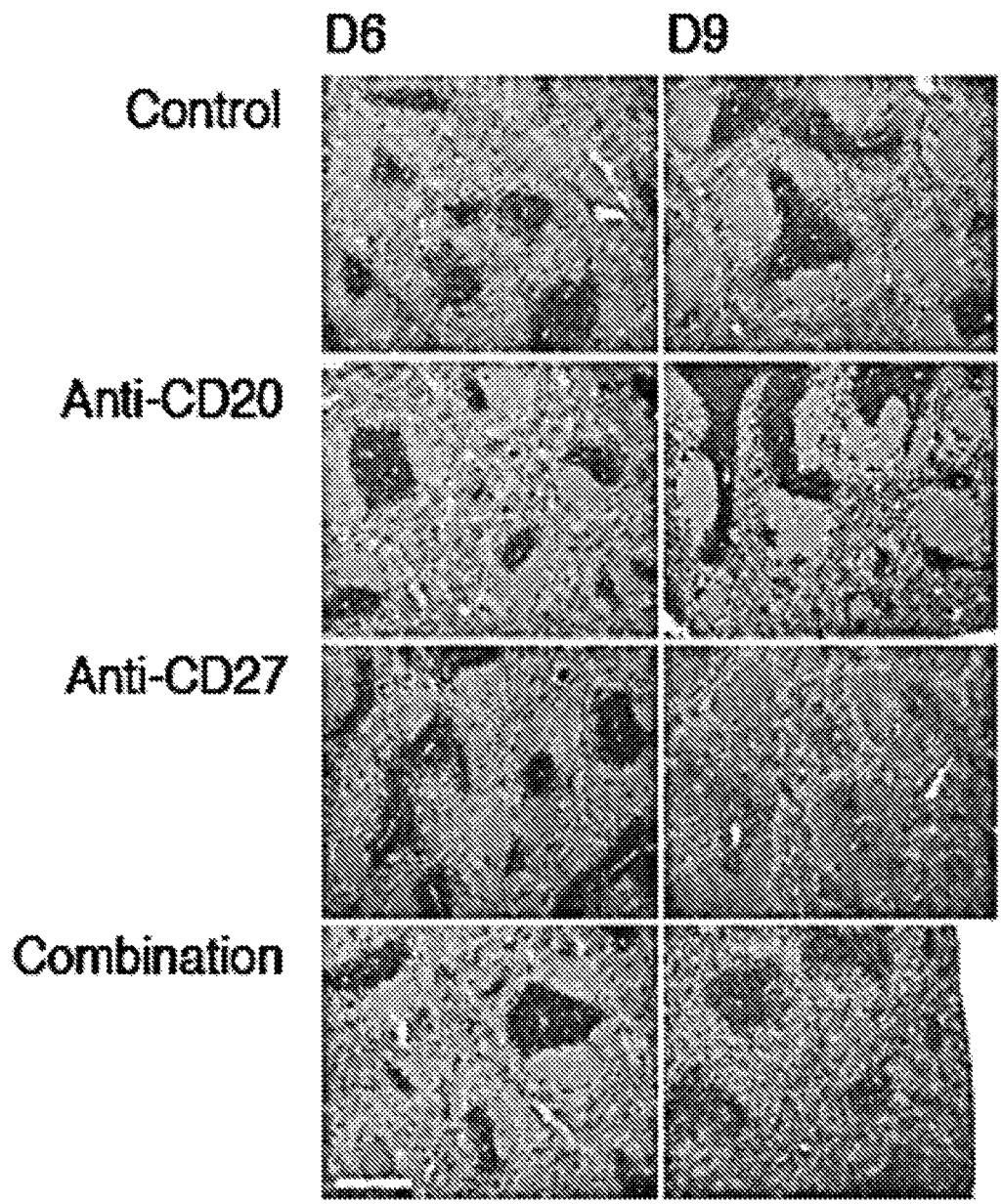

(A) BCL$_1$-bearing, huCD27 tg mice were treated as in FIG. 2A and a Kaplan-Meier survival curve generated (Log-rank test), n=10 per group, from two independent experiments, ****p<0.0001. (B) Human PBMCs were cultured with anti-huCD20, anti-huCD27, anti-hu4-1BB or an isotype control mAb for 48 h. Cells were harvested and analyzed by flow cytometry. Representative plots show gating of monocytes by FSC vs SSC. (C) Cumulative data of (B) are shown in the graph. p values were analyzed by paired student's t test, *p<0.05, p<0.001, medians are shown, n=5-8 per group. (D) CD14 expression on monocytes from (B) are shown in representative plots. (E) Cumulative data of (D) are shown in the graph. p values were analyzed by pared student's t test, p<0.01, ***p<0.001, medians are shown, n=5-8 per group.

(F-G) C57BL/6 mice were inoculated with 50,000 B16F10 tumor cells i.p. on day 0, and treated with anti-gp75 (50 µg) on day 0 and anti-CD27 (100 µg) on day 1 (all i.p.). The mice were harvested on day 13 and peritoneal metastases measured. Representative photographs of the mice are shown in (F), with metastases highlighted by the red arrows (marked "A"). The graph in (G) shows data accumulated from 2 experiments, n=11-12 mice per group. Unpaired Student's t test was used, *p<0.05, **p<0.01, ns indicates not significant.

FIG. 18A discloses flow cytometry plots for BCL$_1$ cells, A31 cells, and Eµ-TCL1 cells.

FIG. 18B discloses flow cytometry plots for CD4+T cells, CD8+T cells, and NK cells.

Figure 19A:
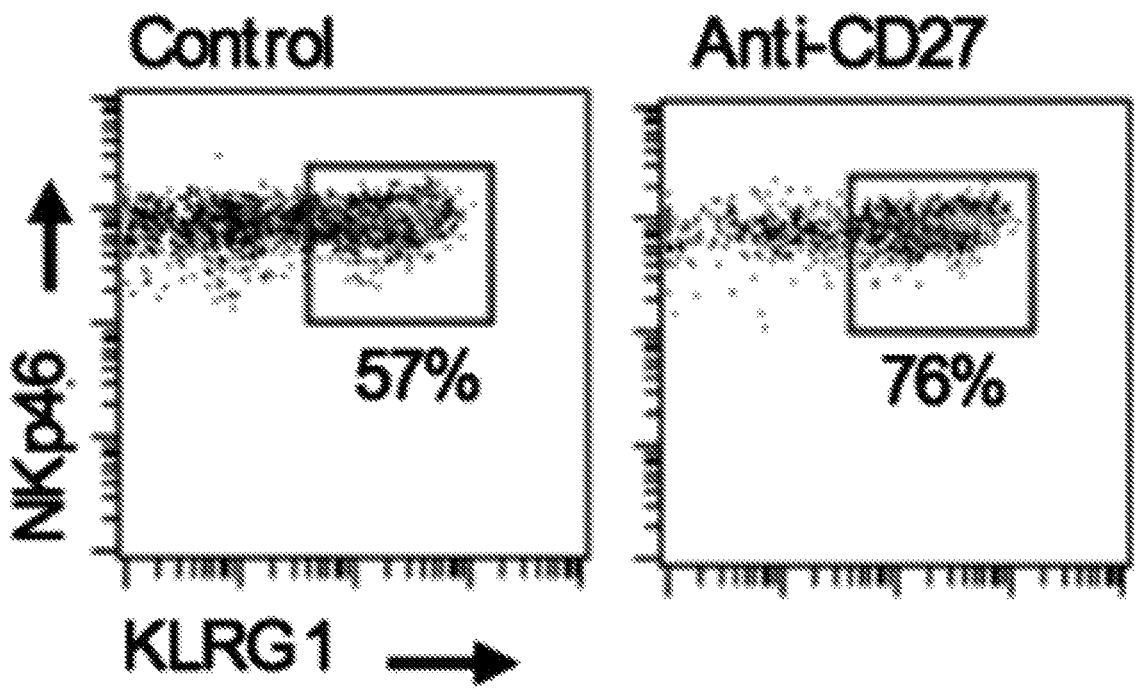

FIG. 19A discloses flow cytometry plots for peripheral blood NK cells.

Figure 19B:
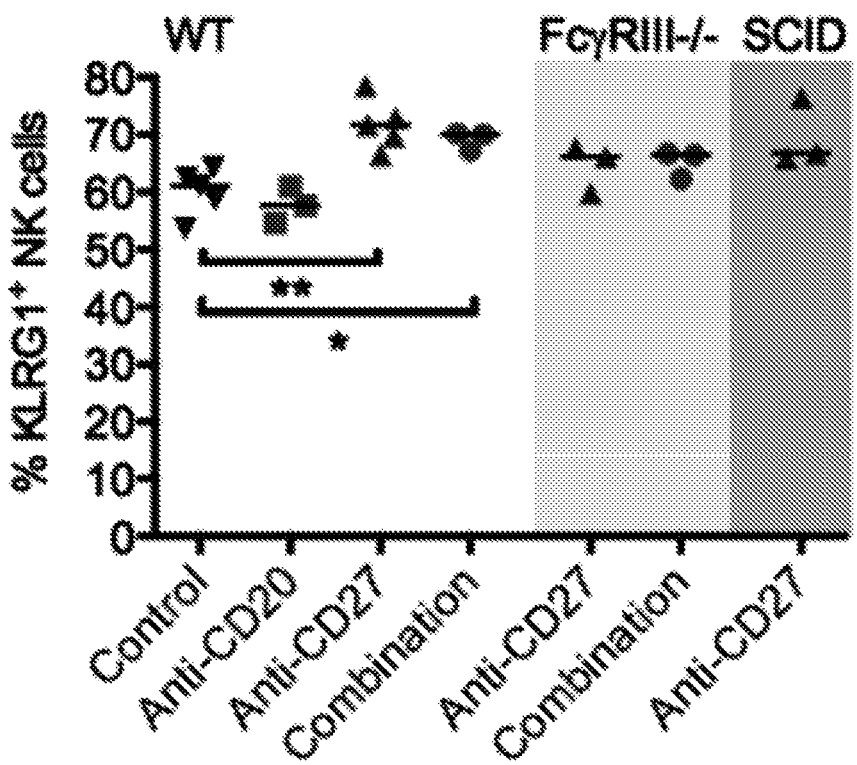

FIG. 19B discloses a chart showing data for peripheral blood NK cells.

Figure 20A:
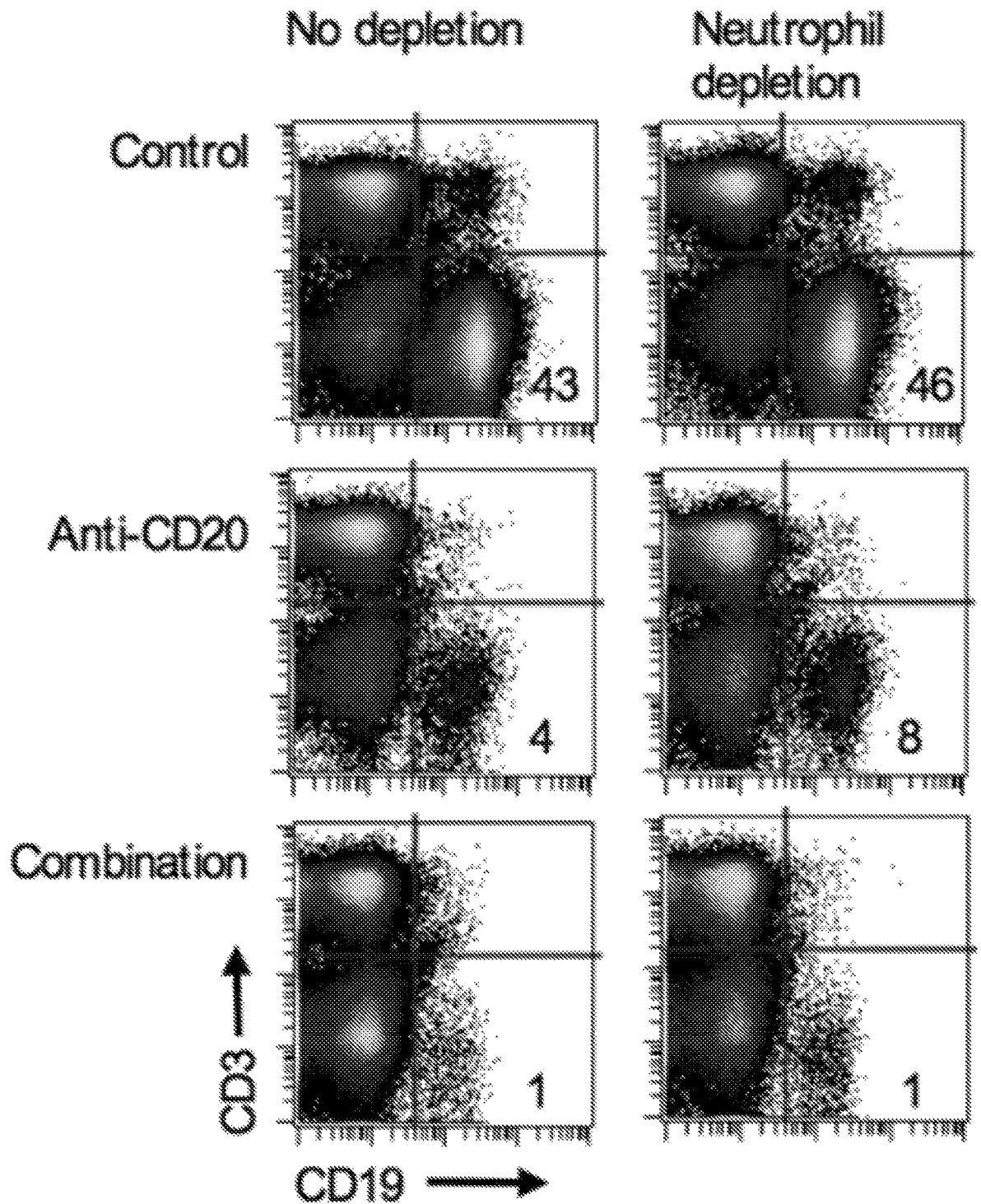

FIG. 20A discloses flow cytometry plots for splenic cells.

Figure 20B:
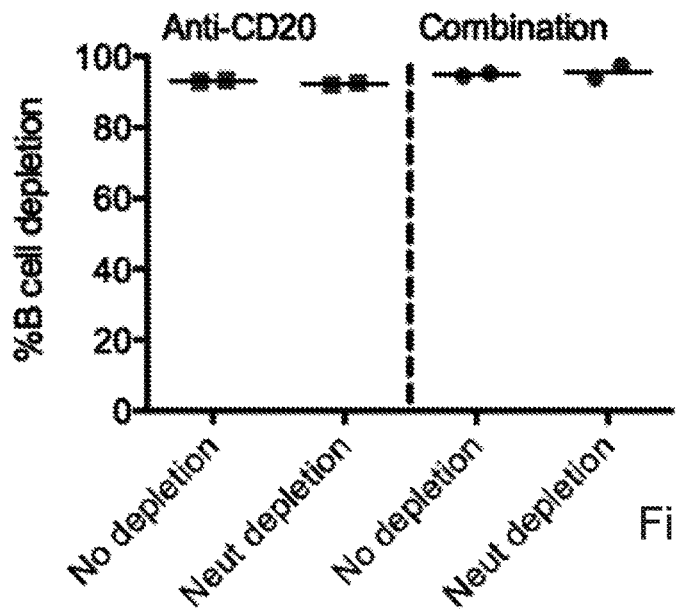

FIG. 20B discloses a chart showing data for splenic cells.

Figure 20C:
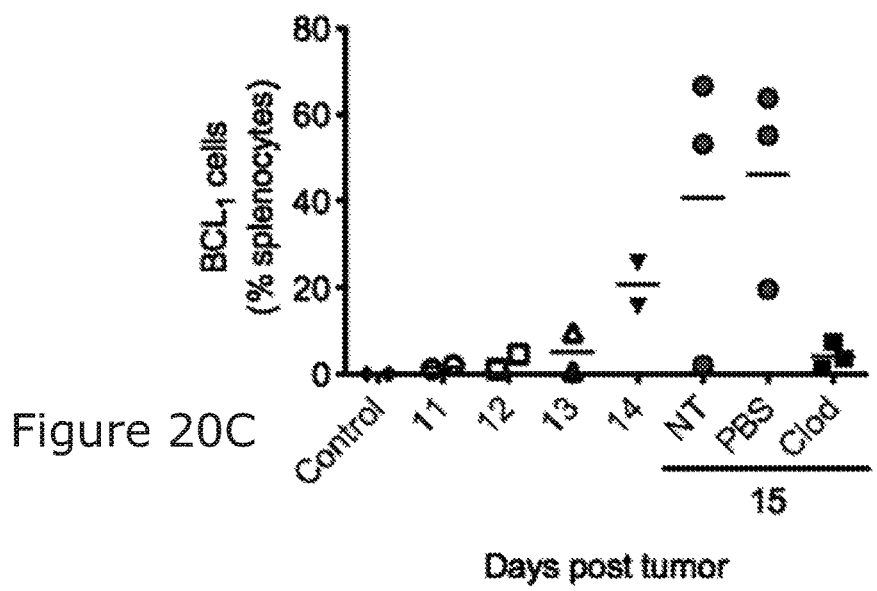

FIG. 20C discloses a chart showing data for splenic BCL$_1$ cells.

Figure 20D:
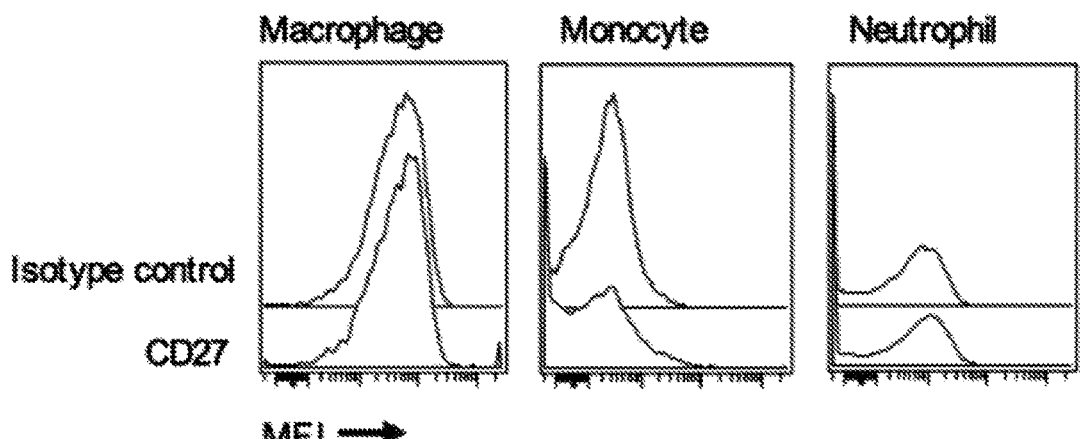

FIG. 20D discloses flow cytometry plots for CD27 expression.

Figure 21:
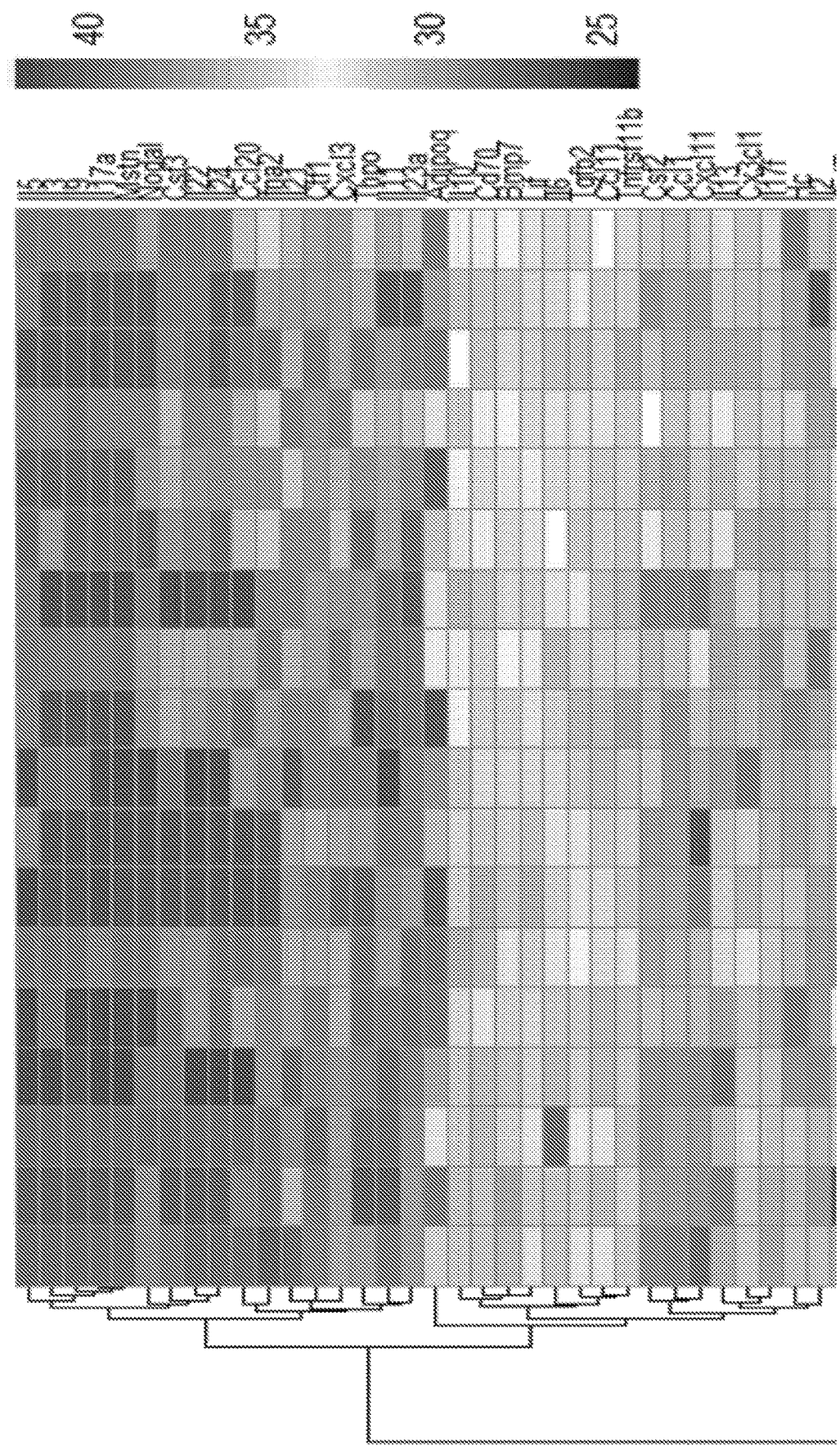
Figure 21:
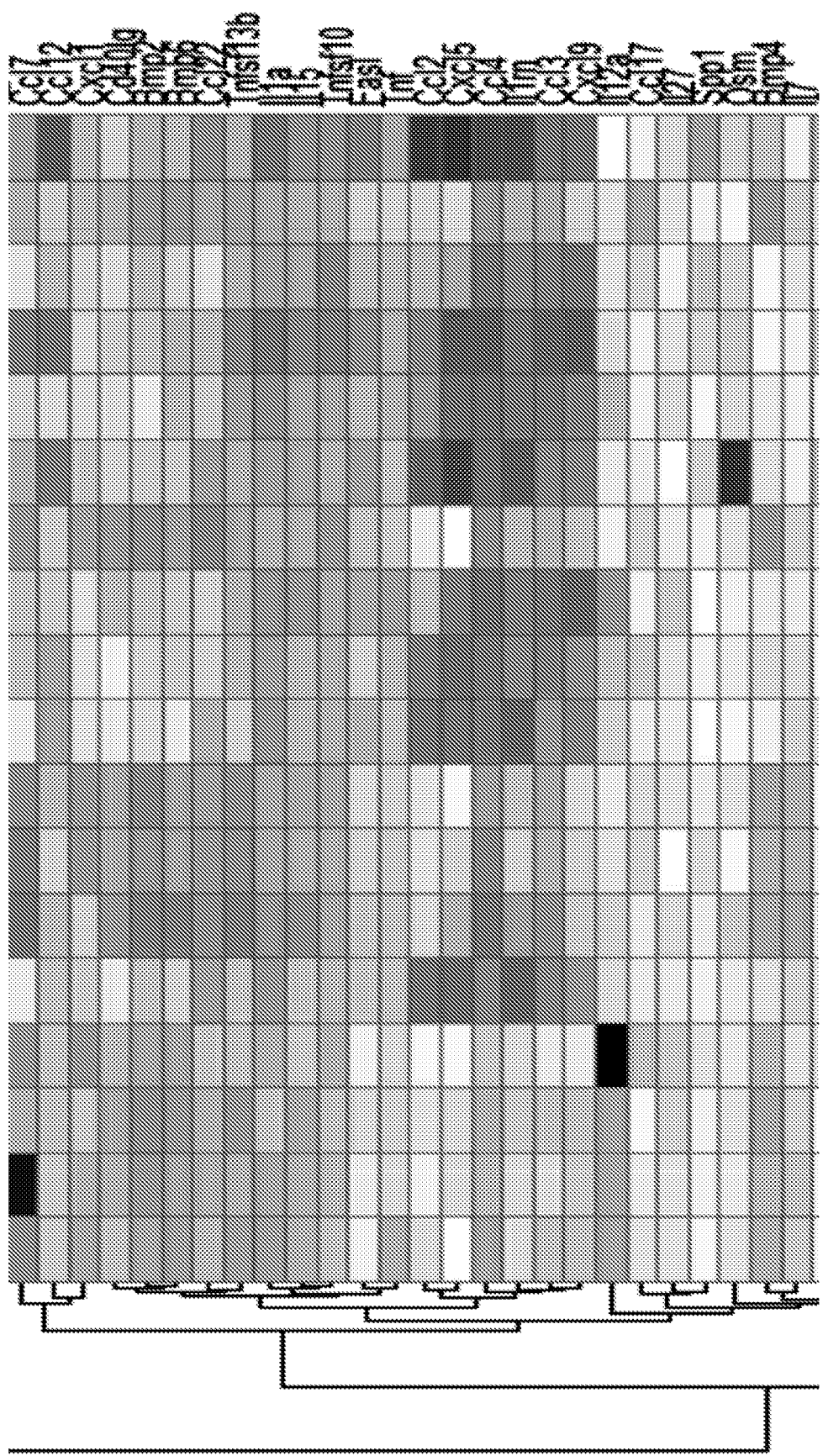
Figure 21:
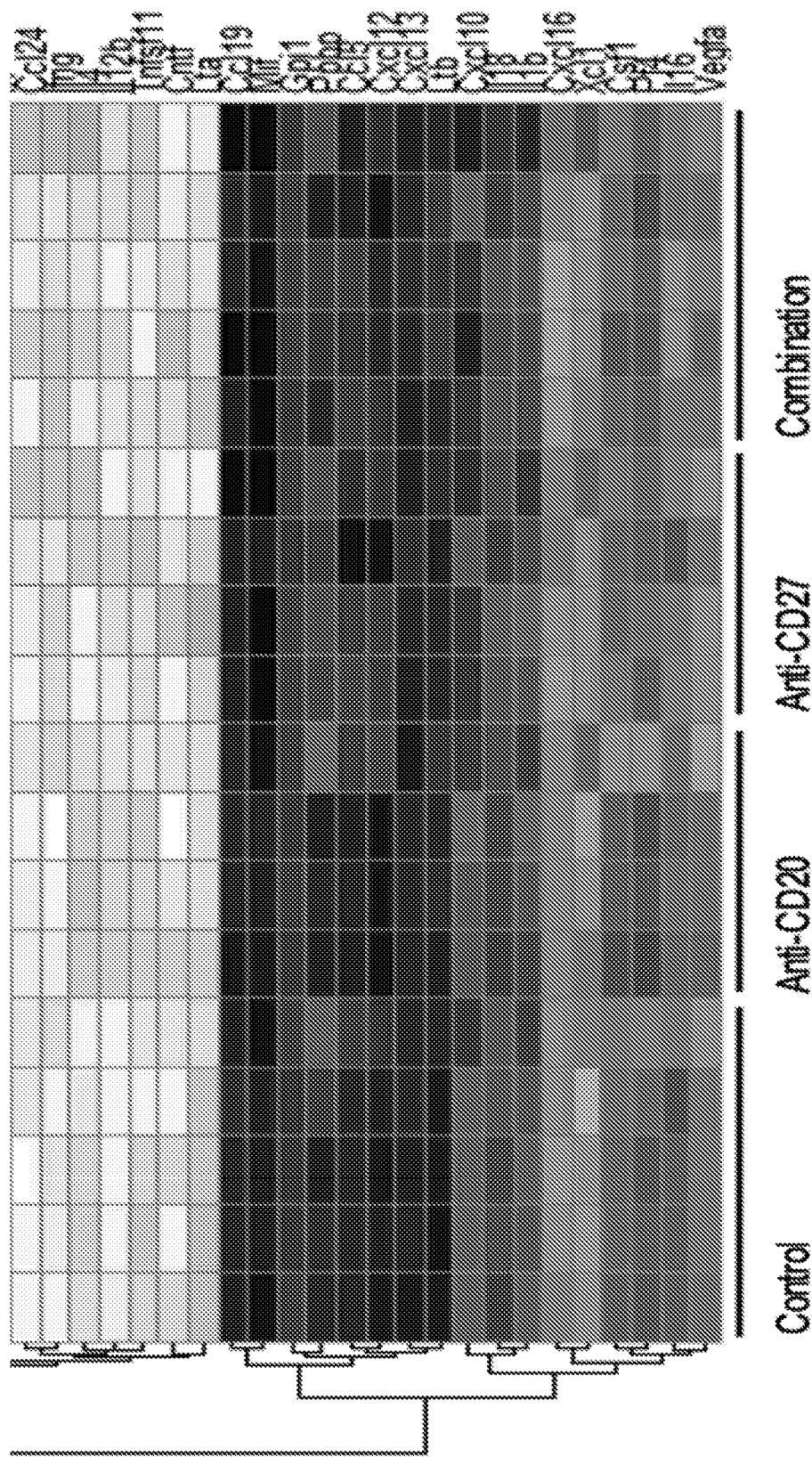

FIG. 21 discloses a heatmap of gene expression data.

Figure 22A:
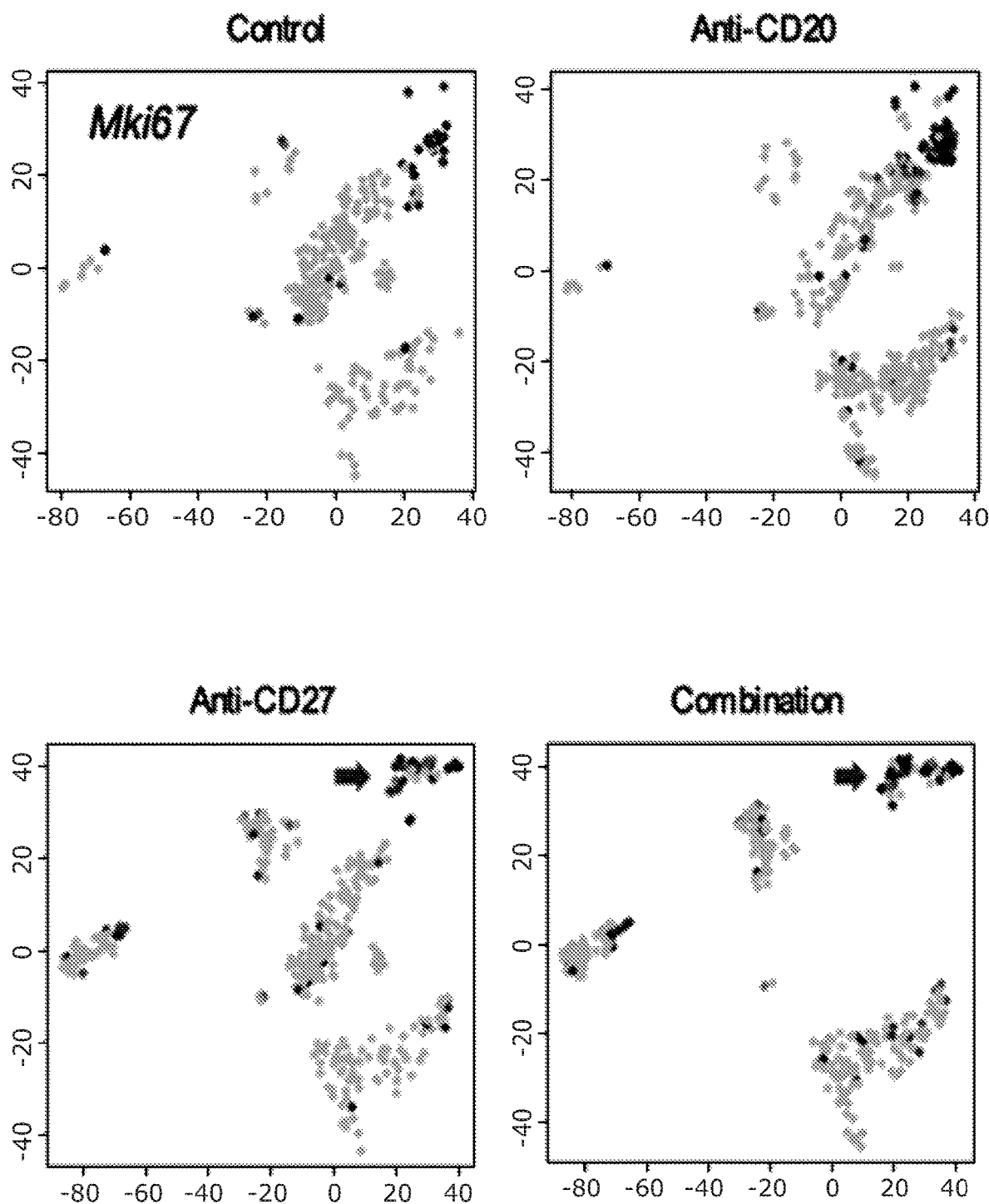

FIG. 22A discloses single cell RNA sequencing data for *Mki67*.

Figure 22B:
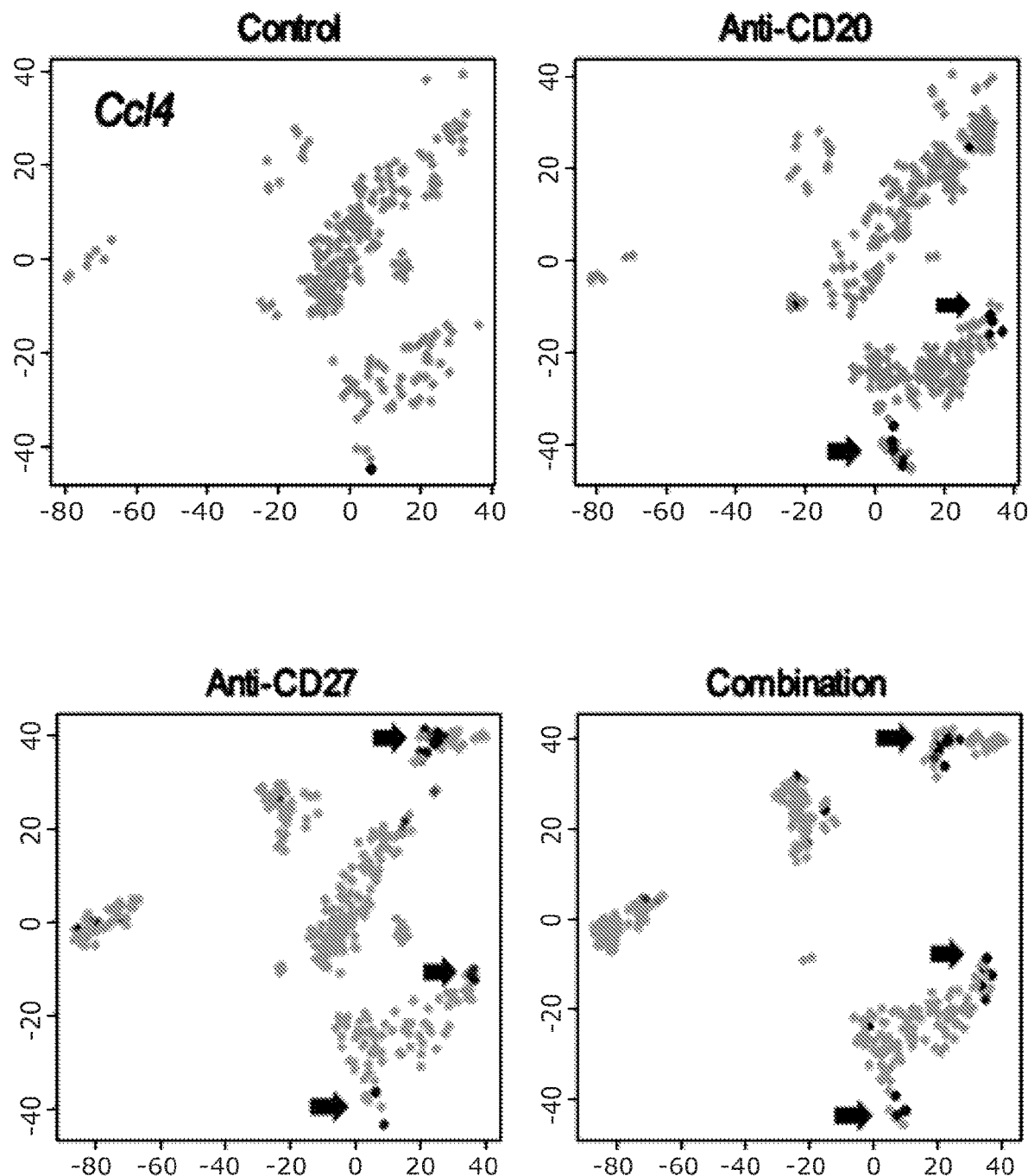

FIG. 22B discloses single cell RNA sequencing data for *Ccl4*.

Figure 22C:
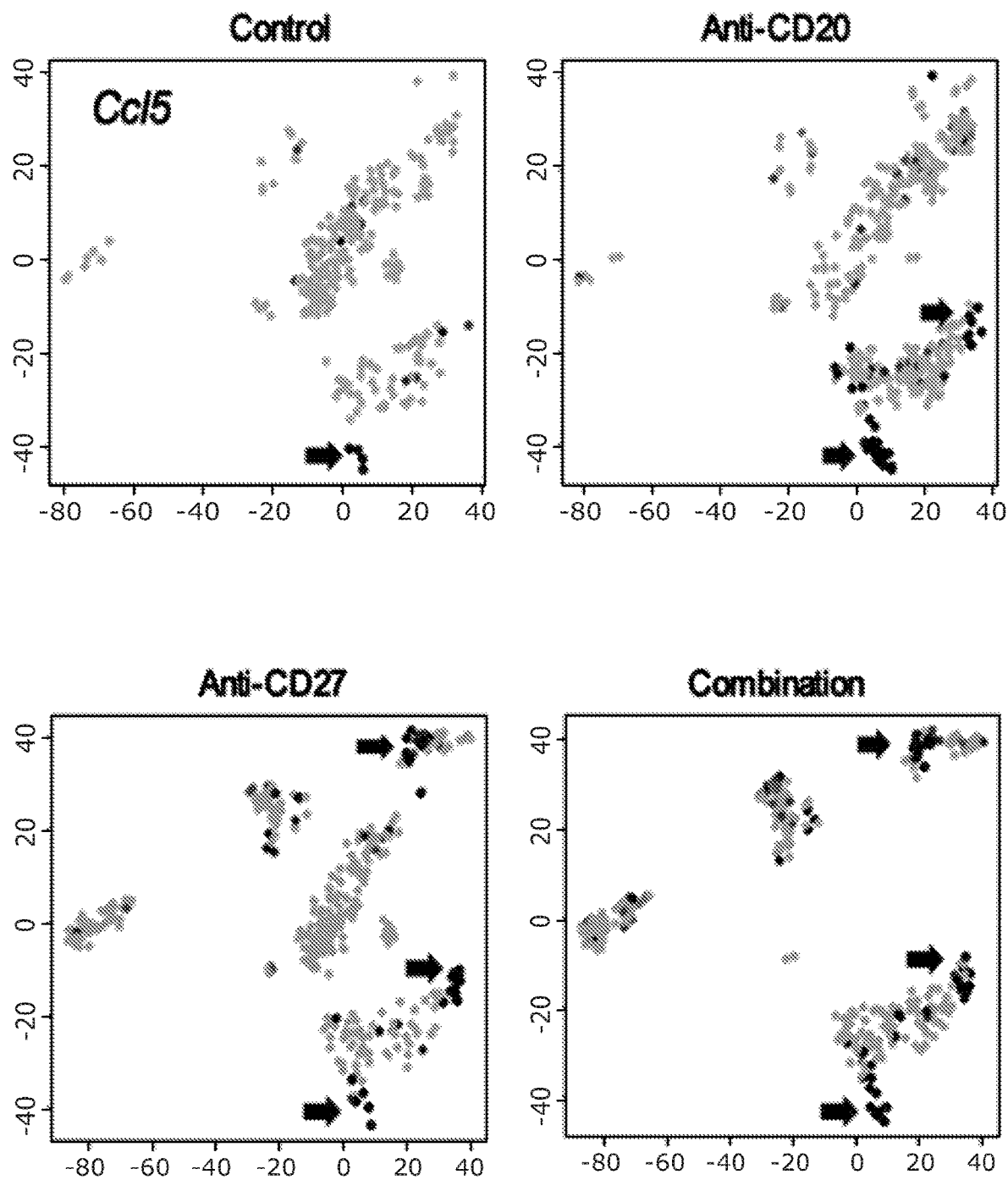

FIG. 22C discloses single cell RNA sequencing data for *Ccl5*.

Figure 22D:
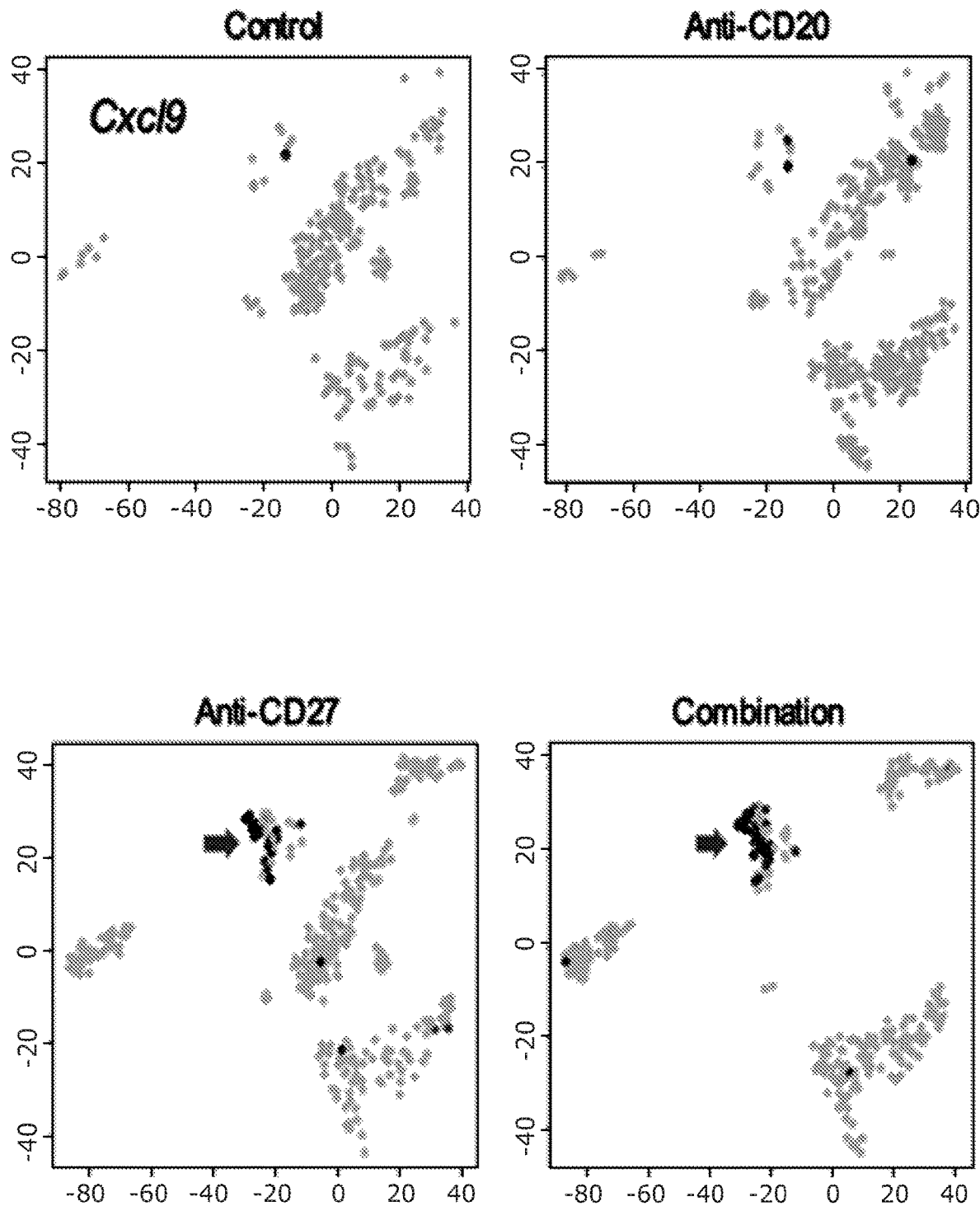

FIG. 22D discloses single cell RNA sequencing data for *Cxcl9*.

Figure 22E:
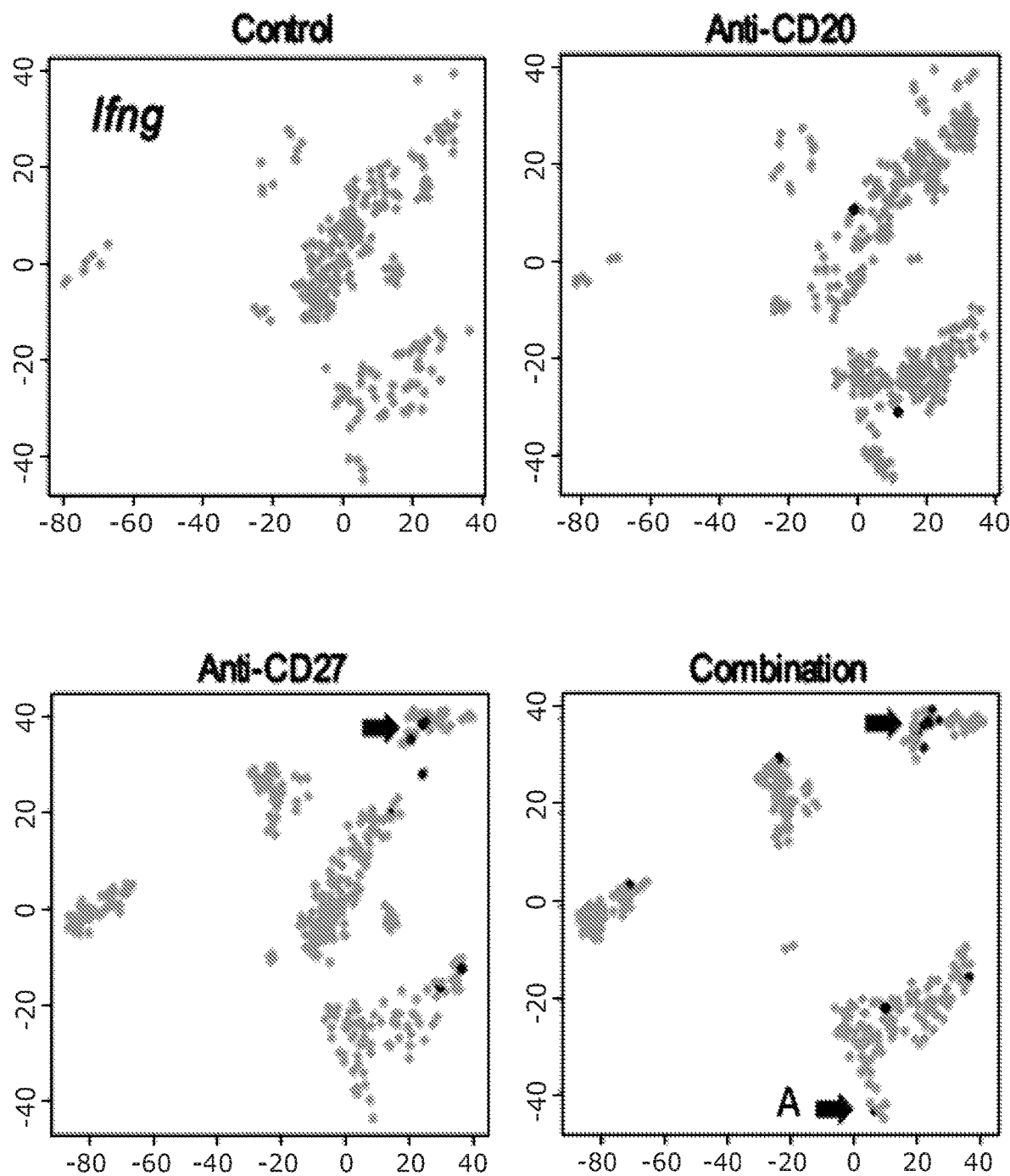

FIG. 22E discloses single cell RNA sequencing data for *Ifng*.

Figure 22F:
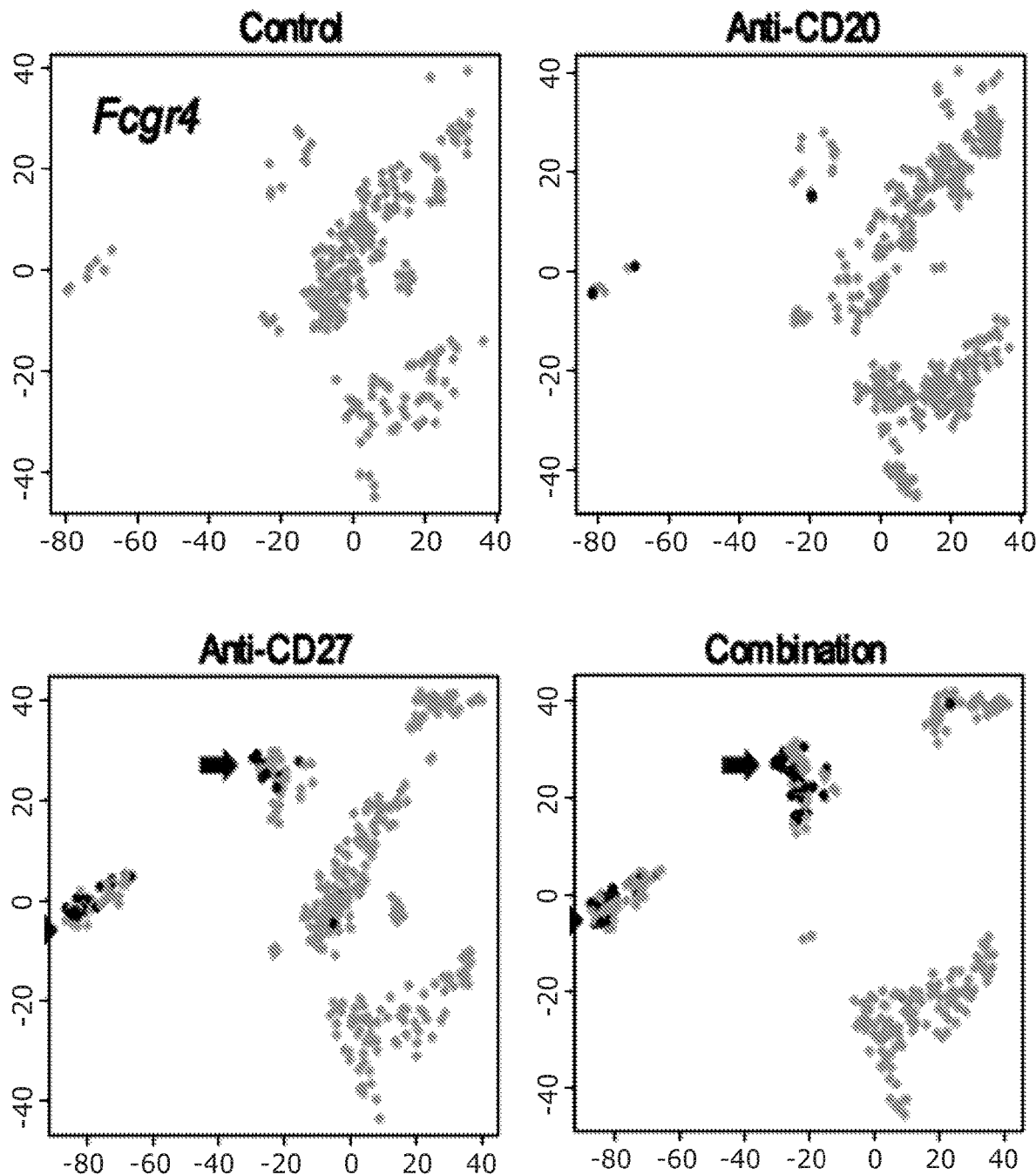

FIG. 22F discloses single cell RNA sequencing data for *Fcgr4*.

EXAMPLE 1

Anti-CD20 mAb therapy on its own has limited activity in B-cell lymphoma, hence it is normally used in combination with chemotherapy. We set out to investigate whether anti-CD20 in combination with anti-CD27 mAb (or other immunomodulatory mAbs) would deliver improved efficacy in immunocompetent Balb/c mice bearing aggressive syngeneic BCL$_1$ tumours. Our initial hypothesis was that if anti-CD20 mAbs elicit tumour death and induce a T-cell response, then further T-cell stimulation with the immunomodulators might enhance this anti-CD20 mediated vaccinal effect.

Anti-CD20 and Anti-CD27 mAb Therapy is Synergistic in B-Cell Lymphoma

Figure 1B:
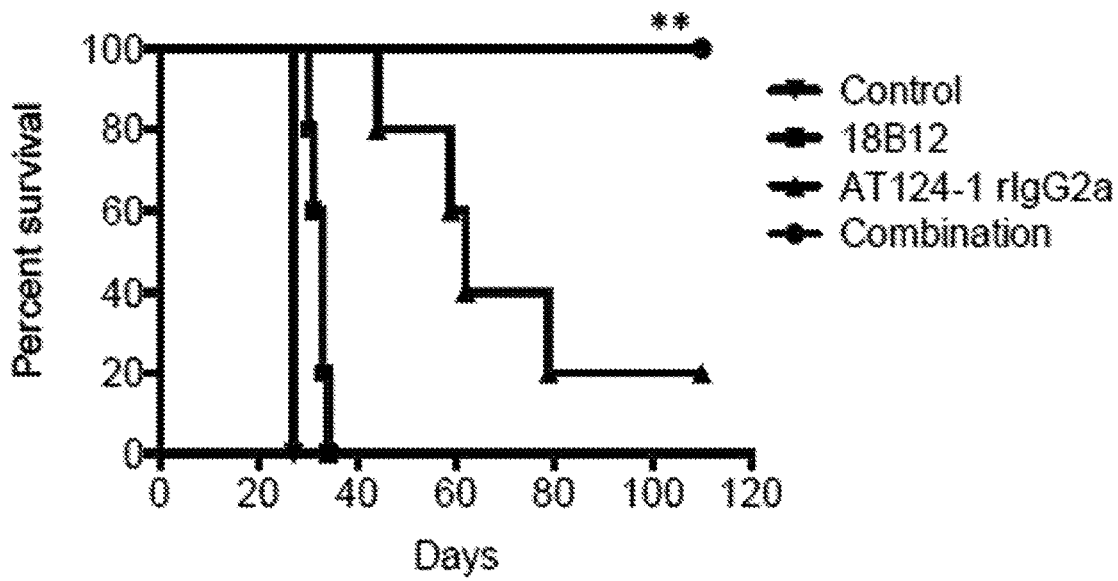
Figure 1C:
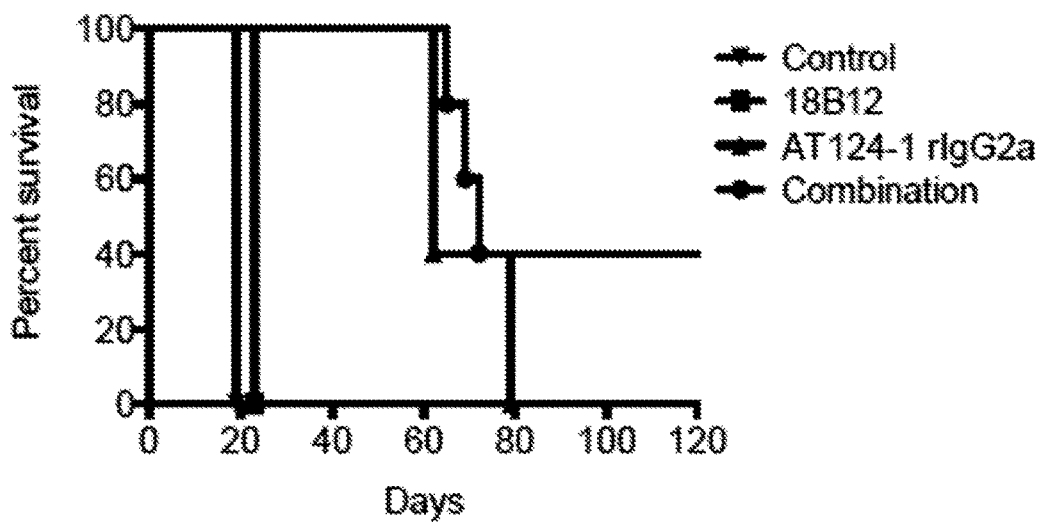

We tested combining 18B12, an anti-murine CD20 mAb with mAbs against CTLA4, PD1, PDL1, GITR, CD134, TIGIT and CD27 (FIG. 1 and FIG. 7). None of the combinations tested, even a triple combination of antiCD20 with anti-PD1 and anti-CTLA4 produced a survival benefit in the mice. The only combination that proved effective was anti-CD20 and anti-CD27 mAb (FIG. 1b). All of the mice treated with the combination of anti-murine CD20 (18B12) and the anti-murine CD27, AT124-1, survived beyond 100 days compared to 20% of mice that received AT124-1 alone whilst none of the PBS or 18B12 mAb treated mice achieved long term survival (FIG. 1b). When the combination was repeated in another aggressive B-cell tumour model, A31, the 18B12 and AT124-1 combination treatment also had better survival compared to the monotherapy groups (FIG. 1c).

Anti-CD27 mAb Promotes Effector Memory CD8 T Cell Expansion

To explore the mechanism of action behind this effective combination we first assessed if BCL1 and A31 tumours expressed CD27 themselves. This was shown not to be the case, ruling out any direct cytotoxicity from AT124-1 (FIG. 8a). It was noted however that CD27 was expressed constitutively on CD4 and CD8 T cells, and NK cells (FIG. 8b). To further investigate the anti-CD20 and anti-CD27 mAb combination, we harvested spleens from mAb-treated $BCL_1$ mice on day 9 (D9) post tumour inoculation. At this time there was a modest increase in the total number of CD8 T cells in mice that had received anti-CD27 mAb (FIG. 2a). Mice treated with anti-CD27 had 10-11% total CD8+ T cells compared to 6% in PBS control and 7% in the anti-CD20 arms. Minimal changes were observed in the numbers of regulatory T cells (Tregs) between the different treatment arms but the ratio of total CD8: Tregs was increased in mice that have received AT124-1 (6 vs. 4).

The distribution of CD8+ T cells in the spleen was also examined by immunohistochemistry (FIG. 2b) on Day 6 (D6) and D9 post tumour inoculation. Mice that had received anti-CD27 demonstrated infiltration of CD8 T cells into the centre of the follicles whereas in non-anti-CD27 treated mice, the CD8 T cells were located in the periphery. This suggests that anti-CD27 mAb therapy might enhance CD8 T cell recruitment into the tumour and increase direct cell-to-cell contact with tumour cells.

Figure 3A:
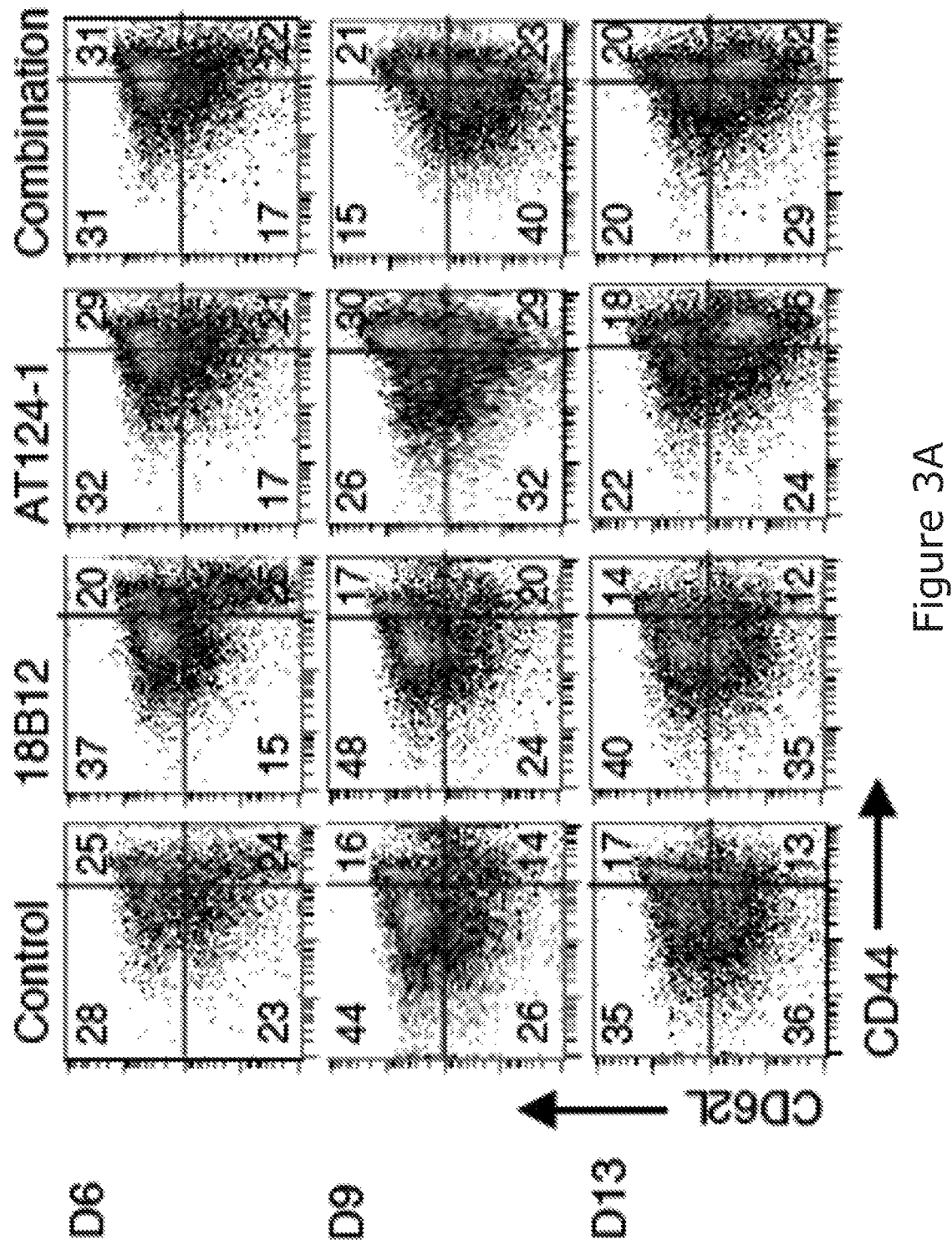
Figure 3B:
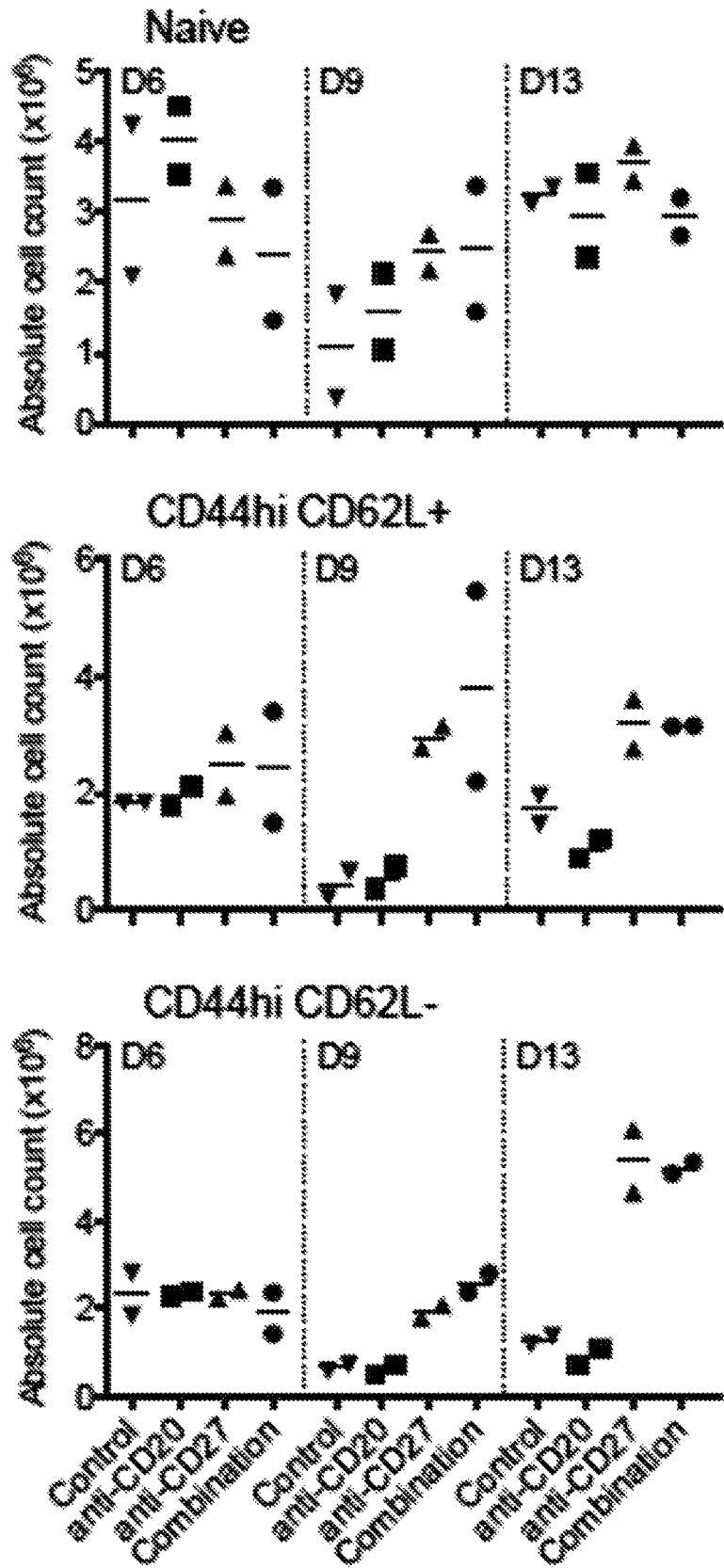
Figure 4A:
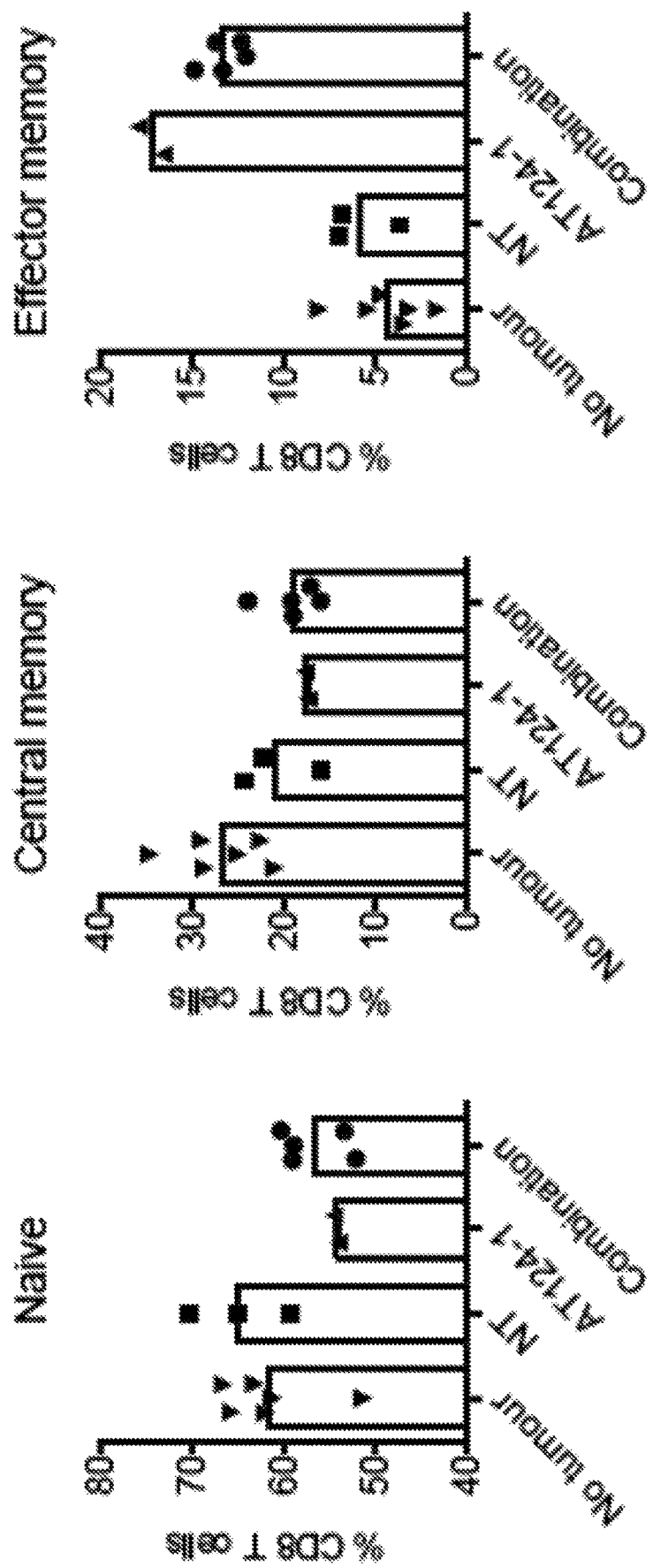

We went on to investigate whether anti-CD27 therapy altered the activation of the CD8 T cells on D6, 9 and 13. On D6, minimal changes were seen in the expression of activation markers, CD44 and CD62L (FIGS. 3a and b). However, by Day 13 (D13), there was 5-fold more activated CD8 T cells (CD44hi CD62L-) in mice that received anti-CD27 compared to anti-CD20 treated mice (FIG. 3b). Furthermore, in surviving mice that received anti-CD27 mAb, there were 2-3 fold more effector memory CD8 T cells (CD44hi CD62L-) at approximately Day 70 post tumour inoculation, compared to naïve and untreated tumour-bearing mice (FIG. 4a). Collectively, these data suggest that anti-CD27 mAb therapy enhances CD8 T cell activation and promotes expansion and persistence of effector memory CD8 T cells.

Figure 4B:
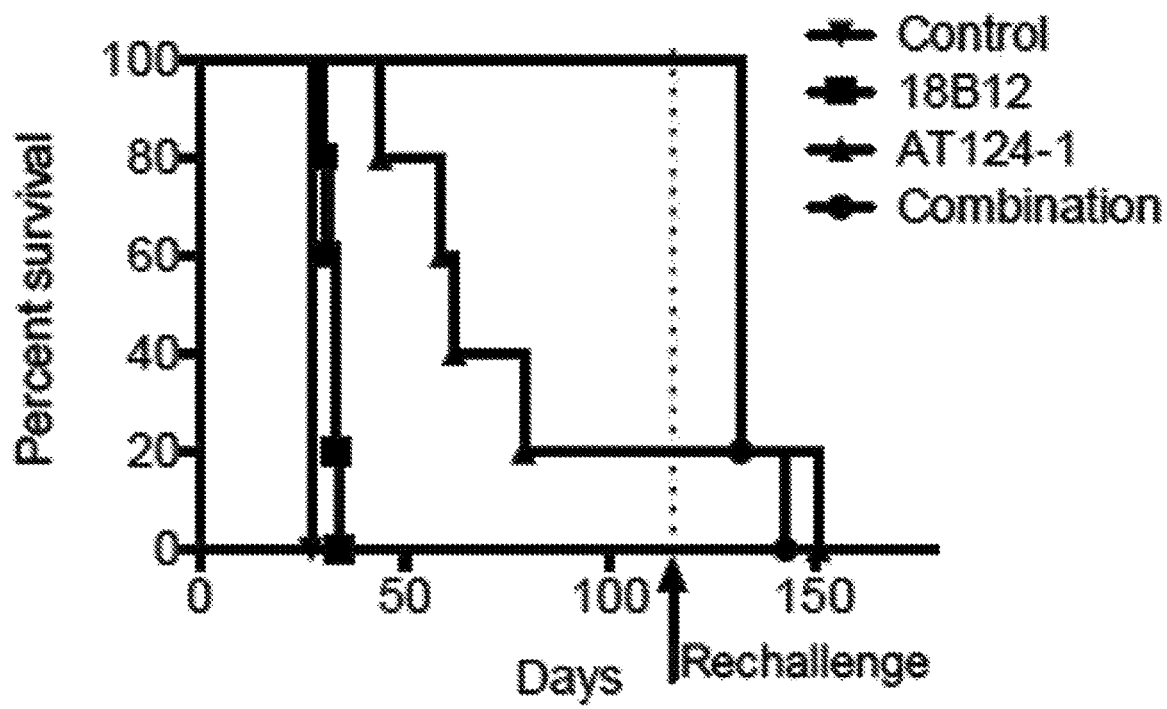
Figure 4C:
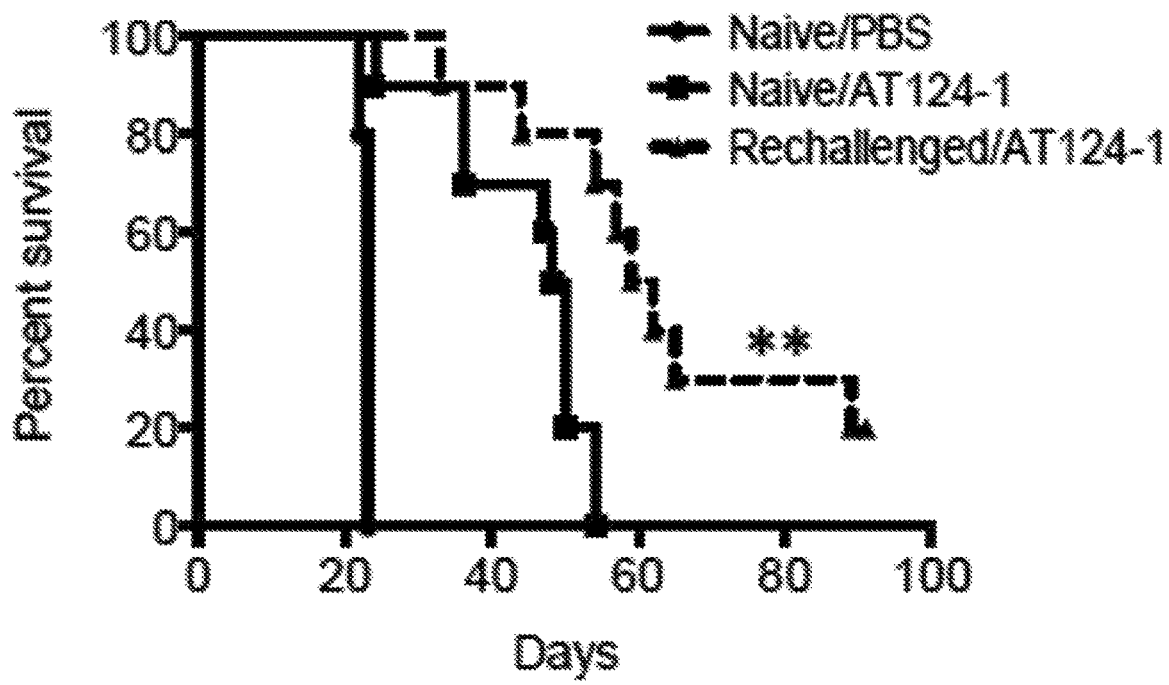

When the surviving mice were rechallenged with $BCL_1$ tumour at day 100, all the mice died at the same rate as the naïve control mice (FIG. 4b). However, when the tumour rechallenge was accompanied with anti-CD27 mAb administration, the rechallenged mice had improved survival compared to naïve, tumour bearing, anti-CD27 treated mice (FIG. 4c). This suggests that CD8 memory T cell response elicited by initial therapy was alone inadequate to overcome tumour rechallenge, but re-treatment with anti-CD27 might lead to a more rapid anti-tumour CTL response.

Anti-CD27 Enhances Recruitment of Myeloid Effector Cells

Figure 5A:
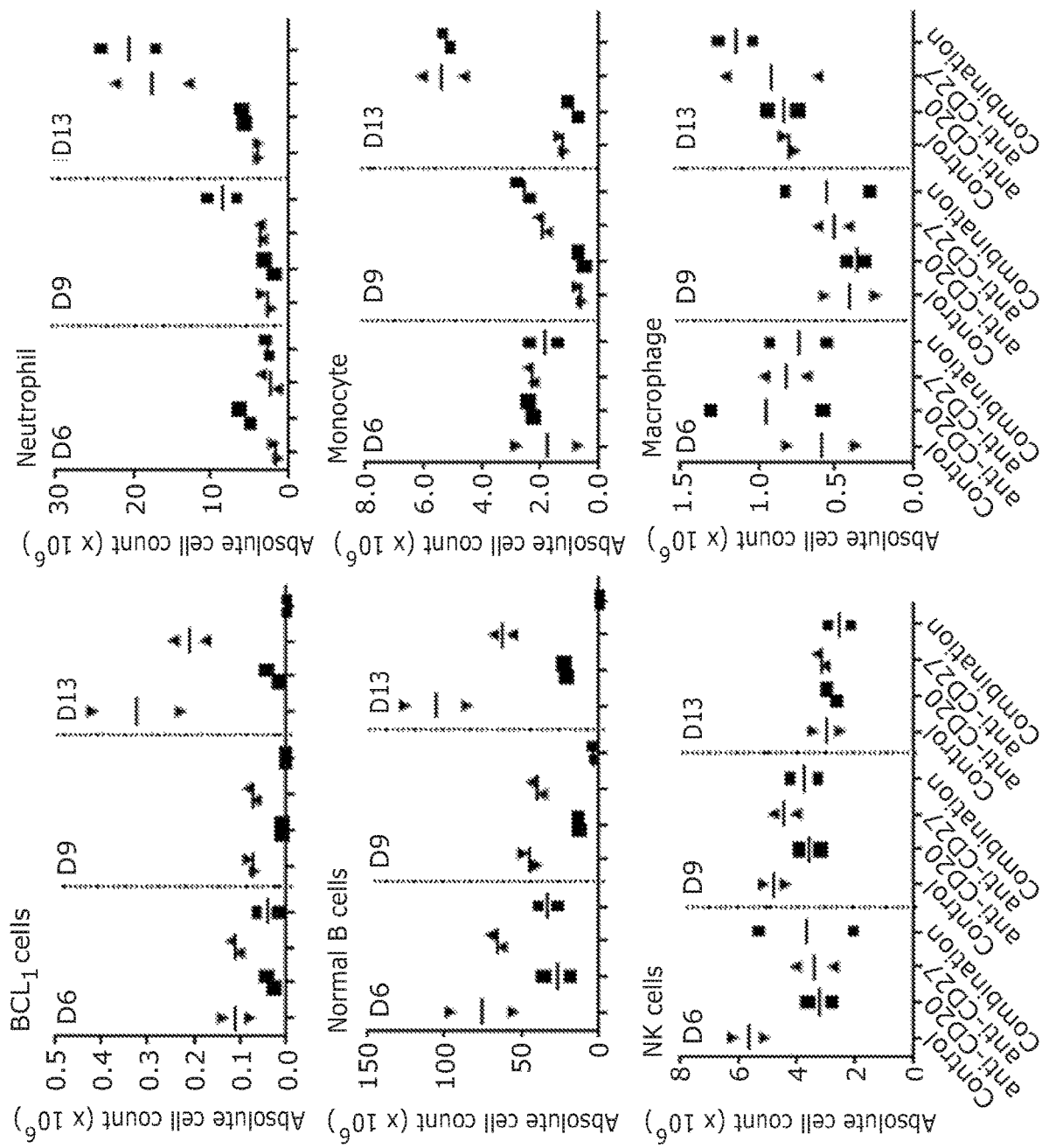
Figure 5B:
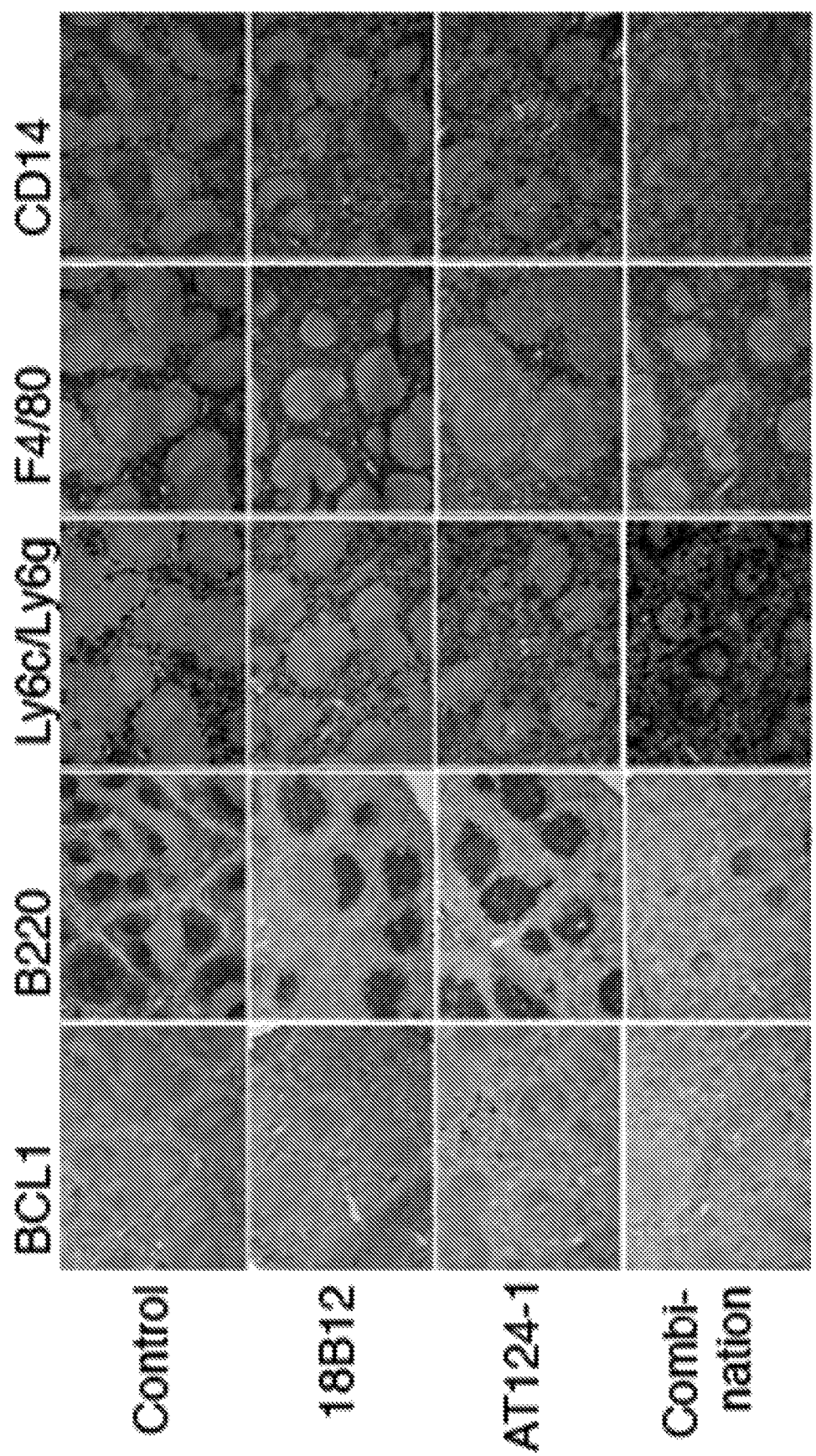

As NK cells also express CD27 constitutively, we examined effects of treatment on the innate immune effector cells in $BCL_1$ bearing mice (FIG. 5a). Apart from D6, where there were more NK cells in the control mice, no obvious changes were observed between treatment arms at each time point. In contrast, anti-CD27 treated mice had a >10 fold increase in neutrophils (CD11b+Ly6g+Ly6c-), 3-fold more monocytes (CD11b+Ly6g-Ly6chi) and a trend towards increased macrophages (F4/80hi CD11bint) on D13. These changes were also confirmed by immunohistochemistry (FIG. 5b). On D9, there were more also neutrophils (Ly6c/Ly6g+), macrophages (F4/80+) and monocytes (CD14+). In the combination treated arm, these myeloid cells were seen to infiltrate the centre of the splenic follicle. Combination treatment with anti-CD20 and anti-CD27 also demonstrated better B-cell depletion than mice treated with anti-CD20 alone, as evidenced by the reduction of normal B cells (B220+) in the combination arm on D9. Together, these data suggest that through a yet unidentified mechanism, anti-CD27 mAb therapy enhances the recruitment of myeloid cells, which then allows improved anti-CD20 mAb mediated deletion of the target B cells, presumably through augmented antibody direct cellular cytotoxicity/phagocytosis (ADCC/ADCP).

Anti-CD20 and Anti-CD27 Therapy is Dependent on NK Cells

Figure 6B:
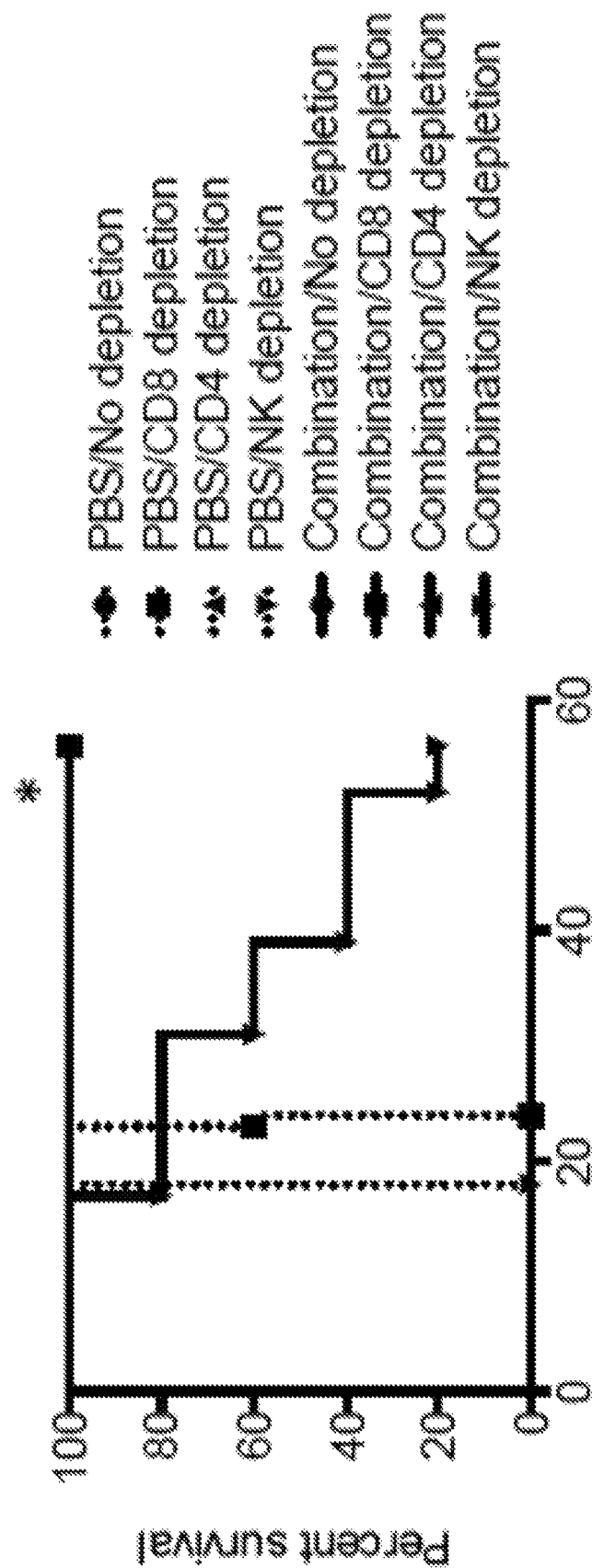
Figure 7A:
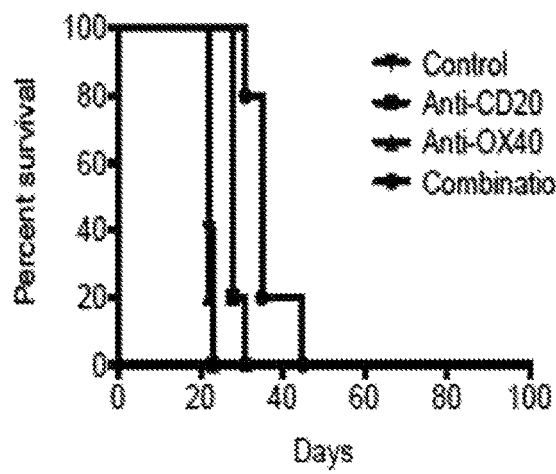
Figure 7B:
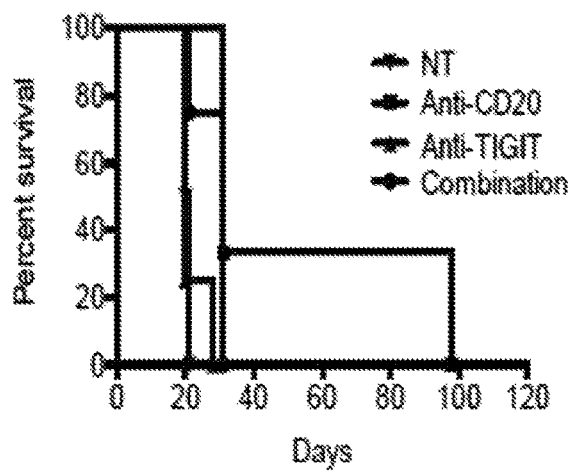
Figure 7C:
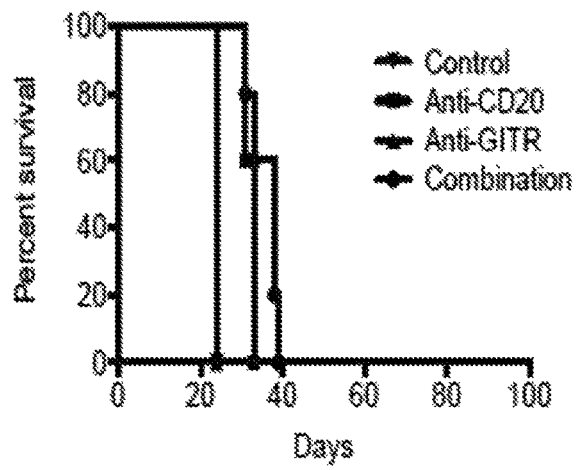
Figure 7D:
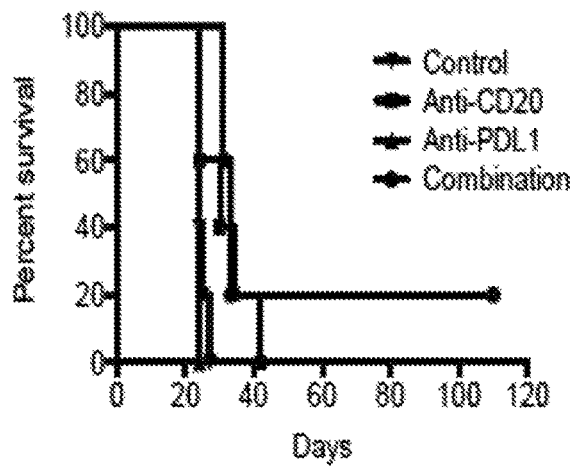
Figure 7E:
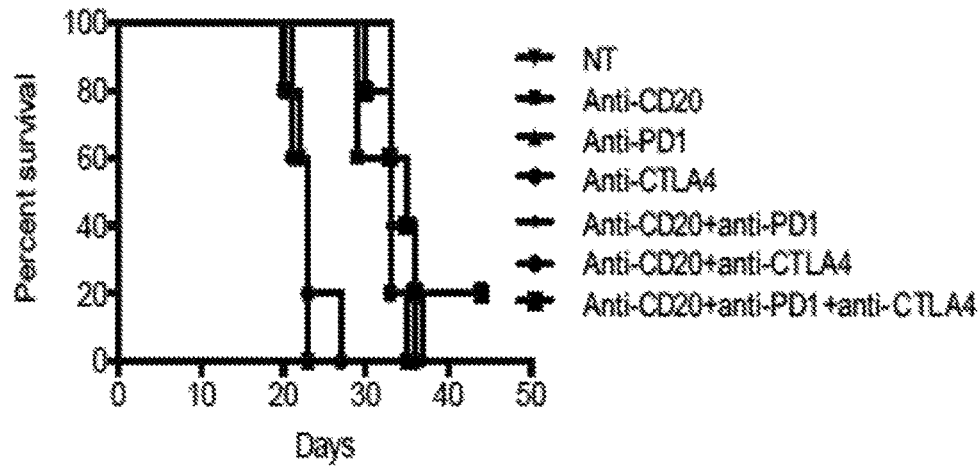

To ascertain which CD27-expressing immune effect or cell is central to the therapeutic efficacy of the anti-CD20 and anti-CD27 combination, NK, CD4+T and CD8+ T cell depletion was performed in the $BCL_1$ model (FIG. 6). We observed that depletion of NK cells from mice inoculated with tumour reduced the survival time by approximately 5 days compared to mice that had not received any depleting mAbs, but this difference was not statistically significant (FIG. 6b). Depletion of NK cells (but not CD4 or CD8 T cells) also markedly reduced the survival of the tumour bearing mice treated with the combination. This suggests that the previously observed CD8 T cell expansion induced by anti-CD27 mAb therapy (FIG. 2) was not required for tumour control, but that NK cells are essential to the antiCD20 anti-CD27 combination, in an as yet unidentified mechanism. Although these findings might seem at odds with the earlier data presented in FIGS. 2-4 relating to the expansion of CD8 T cells; it may be that in the combination therapy CD8 T cells are less important and also that the T cells may play a more prominent role in the later stages of tumour control.

Summary of Results

Our data demonstrates that anti-CD20 and anti-CD27 mAb combination therapy is synergistic in two different immunocompetent, syngeneic mouse models. Mechanistic investigations suggest that the improved efficacy occurs through two independent mechanisms. First, anti-CD27 therapy itself enhances CD8 T cell activation and promotes expansion of effector memory CD8 T cells which might be important in long-term disease control. In human patients, we hypothesise that if rituximab does induce a T cell memory response, then combined anti-CD27 therapy might enhance this response. Second, in a novel mechanism, we propose that antiCD27 therapy might activate NK cells, which then recruit myeloid cells, which mediate ADCC/ADCP, leading to enhanced B-cell depletion by anti-CD20. We have not ruled out a direct killing role for the anti-CD27-activated NK cells, however, given our experience with anti-CD20 therapy, we anticipate that the recruited myeloid cells are likely to be the important effectors.

Materials and Methods

Animals and Cells

Mice were supplied by Charles River Laboratories and maintained in local facilities. $BCL_1$ (1) and A31(2) B-cell lymphoma lines were maintained by passage in BALB/c mice and CBA/H mice, respectively. Animal experiments were conducted according to the UK Home Office license guidelines and approved by the University of Southampton Ethical Committee.

Human CD27 transgenic (huCD27 Tg) mice(3) on BALB/c background were maintained in Celldex animal facilities and used according to the Institutional Animal Care and Use Committees guidelines.

Bone Marrow Isolation and Reconstitution of Mice

Eight- to ten-week old female human CD27 transgenic (huCD27 Tg) mice on BALB/c background were sacrificed and hind femora and tibiae were isolated and muscle and soft tissue removed. Isolated bones were trimmed at both ends and bone marrow flushed with in complete RPMI until bones were white. The collected cells were passed through a 70 um sieve and centrifuged at 1500 rpm. Cells were resuspended in 10% v/v DMSO in foetal calf serum (FCS) and frozen in −80° C. overnight before being transferred to liquid nitrogen storage until use.

Six-week old female BALB/c recipient mice were irradiated in split doses of 5 and 4 Gy, a day apart, in a x. $2-3\times10^6$/recipient bone marrow cells were thawed, washed and injected in PBS via tail veins. Recipients were housed in pathogen-free facilities and fed acid water. Eight to 10-weeks after bone marrow transplantation, animals were bled and huCD27 expression inspected by flow cytometry.

Antibodies and Reagents

18B12 (anti-CD20)(4) was produced in-house from published patented sequences as previously described. AT124-1 (anti-CD27)(5), Mc39-16 (anti-A31 idiotype)(6), Mc10-6A5 (anti-$BCL_1$ idiotype)(7), OX86 (anti-CD134)(8), LOB12.3 (anti-CD137) (9), anti-TIGIT, YTS169 (anti-CD8), GK1.5 (anti-CD4) were typically produced from the culture supernatant of hybridoma cells or stably transfected Chinese hamster ovary cells.

10F.9G2 (anti-PD-L1), RMP1-14 (anti-PD-1), 9D9 (anti-CTLA4), DTA-1 (anti-GITR) mAbs were purchased from BioXcell. NK depleting antibody, anti-asialoGM1 was purchased from Wako Chemicals.

Anti-human CD27 mAb, varlilumab(3), was gifted by Celldex and produced as previously described.

In Vivo Immunotherapy Experiments

Groups of 8- to 12-week old female BALB/c mice (n=5-6) received $10^4$ $BCL_1$ or A31 cells intravenously on day 0 followed by anti-CD20 (200 ug) on day 4 and anti-CD27 (100 ug/injection) from day 5-8 by intraperitoneal injection. Alternatively, $BCL_1$-inoculated mice received an alternative immune modulatory mAb from day 5 onwards as specified in the figure.

For depletion experiments, mice were treated with YTS169 (CD8 depletion), GK1.5 (CD4 depletion) and asialo-GM1 (NK depletion) at doses of 500 ug, 1 mg and 50 ul per injection, every 5 days, from D-1 to D-16 i.p.

Flow Cytometry

Flow cytometry was performed as previously described (6) using FACSCalibur or FACSCanto (all from BD Biosciences, Oxford, Oxfordshire, UK) with data analysed using Cytobank (Cytobank, Inc, Mountain View, Calififornia, USA).

Peripheral blood and/or spleen suspensions were analysed for CD8+T subsets (anti-CD3, anti-CD8, anti-CD44, anti-CD62L), Tregs (anti-CD3 PerCP eFluor 710, anti-CD4 FITC, anti-CD25 APC, anti-FOXP3 PE), $BCL_1$ tumour (anti-CD19 APC, anti-$BCL_1$ idiotype FITC), NK cells (anti-CD3 FITC, anti-NKp46 PE, anti-CD49b PerCP eFluor 710) and myeloid cells (anti-CD11b e450, anti-F4/80 Alexa Fluor 647, anti-Ly6g APC e780, anti-Lytic PE Cy7) and CD27 expression (anti-human CD27 PE, anti-mouse CD27 PE), in the presence of the FcgR blocking mAb, 2.4G2. All conjugated antibodies were purchased from BD Biosciences, Oxford, UK and EBioscience, High Wycombe, UK except for 2.4G2 (in-house), anti-$BCL_1$ idiotype FITC (in-house) and anti-F4/80 Alexa Fluor 647 (Bio-Rad Laboratories, Hemel Hempstead, UK).

To enumerate myeloid cells in the spleen, tissue digestion was performed using Liberase (Sigma Aldrich, Gillingham, UK) after tissue harvest as per manufacturer's protocol. Briefly, harvested tissue was cut into small pieces and treated in Liberase TL for 15 min before mashing into a single cell suspension.

Immunohistochemistry

Spleens were harvested on Day 9 and embedded in OCT (CellPath, Newtown, Powys, U.K.) and frozen in isopentane. Eight micrometre slices were air-dried overnight, fixed in 100% acetone and blocked with 2.5% normal goat serum and stained for BCL1 cells (anti-BCL idiotype), normal B cells (anti-B220), neutrophils (anti-Ly6c/Ly6g), macrophage (anti-F4/80) and monocyte (anti-CD14). Sections were treated with a peroxidase inhibitor (Pierce, Thermo Fisher Scientific) for 10 min before incubation with an HRP-conjugated anti-rat IgG polymer for 30 min, followed by 3,3'-diaminobenzidine for 5 min, and counterstained with haematoxylin (all from Vector Laboratories, Peterborough, Cambridgeshire, UK).

Images were recorded using a CXK41 inverted microscope equipped with a CC12 colour camera, Plan Achromat 4×0.25 objective lens and Cell B software (all from Oympus, Southend-on-Sea, Essex, UK).

Statistics

Statistical analysis was performed using the two-tailed Student t text in Graphpad Prism version x software. To assess survival differences in immunotherapy experiments, Kaplan-Meier curves were produced and analysed by log-rank testing.

REFERENCES

1. Slavin, S., and S. Strober. 1978. Spontaneous murine B-cell leukaemia. *Nature* 272: 624-626.
2. Cobb, L. M., M. J. Glennie, H. M. McBride, G. Breckon, and T. C. Richardson. 1986. Characterisation of a new murine B cell lymphoma. *British journal of cancer* 54: 807-818.
3. He, L. Z., N. Prostak, L. J. Thomas, L. Vitale, J. Weidlick, A. Crocker, C. D. Pilsmaker, S. M. Round, A. Tutt, M. J. Glennie, H. Marsh, and T. Keler. 2013. Agonist anti-human CD27 monoclonal antibody induces T cell activation and tumor immunity in human CD27-transgenic mice. *Journal of immunology* 191: 4174-4183.
4. Brezinsky, S. C., G. G. Chiang, A. Szilvasi, S. Mohan, R. I. Shapiro, A. MacLean, W. Sisk, and G. Thill. 2003. A simple method for enriching populations of transfected CHO cells for cells of higher specific productivity. *Journal of immunological methods* 277: 141-155.
5. French, R. R., V. Y. Taraban, G. R. Crowther, T. F. Rowley, J. C. Gray, P. W. Johnson, A. L. Tutt, A. Al-Shamkhani, and M. J. Glennie. 2007. Eradication of lymphoma by CD8 T cells following anti-CD40 monoclonal antibody therapy is critically dependent on CD27 costimulation. *Blood* 109: 4810-4815.
6. Tutt, A. L., R. R. French, T. M. Illidge, J. Honeychurch, H. M. McBride, C. A. Penfold, D. T. Fearon, R. M. Parkhouse, G. G. Klaus, and M. J. Glennie. 1998. Monoclonal antibody therapy of B cell lymphoma: signaling activity on tumor cells appears more important than recruitment of effectors. *Journal of immunology* 161: 3176-3185.
7. George, A. J., H. M. McBride, M. J. Glennie, L. J. Smith, and F. K. Stevenson. 1991. Monoclonal antibodies raised against the idiotype of the murine B cell lymphoma, BCL1 act primarily with heavy chain determinants. *Hybridoma* 10: 219-227.

8. al-Shamkhani, A., M. L. Birkeland, M. Puklavec, M. H. Brown, W. James, and A. N. Barclay. 1996. OX40 is differentially expressed on activated rat and mouse T cells and is the sole receptor for the OX40 ligand. *European journal of immunology* 26: 1695-1699.

9. Taraban, V. Y., T. F. Rowley, L. O'Brien, H. T. Chan, L. E. Haswell, M. H. Green, A. L. Tutt, M. J. Glennie, and A. Al-Shamkhani. 2002. Expression and costimulatory effects of the TNF receptor superfamily members CD134 (OX40) and CD137 (4-1BB), and their role in the generation of anti-tumor immune responses. *European journal of immunology* 32: 3617-3627.

All references discussed herein are incorporated by reference.

EXAMPLE 2—ANTIBODY TUMOR TARGETING IS ENHANCED BY CD27 AGONISTS THROUGH MYELOID RECRUITMENT

Summary

Anti-cancer monoclonal antibodies (mAbs) destroy cancer directly by recruiting effectors such as myeloid cells, or by targeting immunomodulatory receptors to promote cytotoxic T cells. Here, we examined the potential of combining an archetypal direct tumor targeting mAb, anti-CD20 with a panel of immunomodulatory mAbs. Only agonistic anti-CD27 provided cures in combination with anti-CD20. This was apparent in multiple lymphoma models, including human CD27 transgenic mice using anti-human CD27, varlilumab. Detailed analysis using single cell RNA sequencing demonstrated that anti-CD27 stimulated CD8$^+$ T and NK cells to release myeloid chemo-attractants and IFNγ, subsequent myeloid infiltration, and macrophage activation. This study demonstrates the therapeutic advantage of using an immunomodulatory mAb to modulate myeloid cells, which then enhances killing by direct tumor targeting mAbs.

Significance

Direct tumor targeting mAbs kill tumor primarily through macrophage-mediated phagocytosis, and have demonstrated unequivocal anti-tumor activity in a number of different cancers. However, these responses are often partial and transient. The anti-tumor activity of these mAbs can be enhanced by increasing the activity and number of macrophages available to phagocytose opsonized tumor cells. This can be achieved indirectly through stimulation of CD27, a costimulatory receptor expressed constitutively on T and NK cells. Activation of these cells triggers the release of chemokines and cytokines that activates and attracts macrophages. Here we described the off-target effects of an immunomodulatory mAb and how it can be harnessed to improve the anti-tumor efficacy of direct tumor targeting antibodies, and in multiple tumor types.

Introduction

Monoclonal antibodies (mAbs) have proven to be potent tools in cancer treatment. They can be divided into two groups based on their effector functions: Direct tumor targeting mAbs, such as anti-CD20, anti-Her2 and anti-EGFR target the tumor directly through innate effectors, whereas immunomodulatory mAbs (e.g. anti-PD-1, anti-PD-L1, anti-CTLA-4 and anti-CD40) activate the adaptive immune system. It is generally agreed that direct targeting mAbs exert their anti-tumor activity by recruiting FcγR-expressing cellular effectors or by blocking oncogenic signaling, whereas, immunomodulators either reduce the threshold for immune stimulation (checkpoint blockers) or directly stimulate immune effector cells (immunostimulatory mAbs). It has previously been shown that when combined, certain immunomodulatory mAbs (i.e. 4-1BB) can improve the anti-tumor efficacy of direct tumor targeting mAbs (CD20) through enhancement of NK cell-mediated antibody-dependent cellular cytotoxicity (ADCC) (Gill et al., 2012; Kohrt et al., 2011), although this remains to be validated in the clinic. Apart from these data, there are few other studies examining the combination of direct tumor targeting and immunomodulatory mAbs. To this end, we examined whether the anti-tumor efficacy of the archetypal direct targeting mAb, anti-CD20, could be enhanced by different immunomodulatory mAb.

From a wide range of targets examined, including PD-1, PD-L1, TIGIT, CTLA-4, GITR, 4-1BB and OX40, agonistic mAb to CD27 was found to be uniquely potent in promoting the activity of the direct tumor targeting mAb, anti-CD20. CD27 is a member of the tumor necrosis factor receptor (TNFR) superfamily and exists as a type 1 transmembrane, disulphide-linked homodimer. Unlike other TNFR members, which are only expressed following activation, CD27 is constitutively present on all subsets of T cells, a subset of NK cells, and memory B cells. Upon T cell activation, CD27 expression is further transiently upregulated. Physiologically, CD27 activation is regulated by restricted expression of its ligand, CD70 and on T cells only takes place when the T cell receptor (TCR) is simultaneously engaged. CD70-CD27 interaction leads to recruitment of TNFR-associated factor (TRAFs) proteins to the CD27 cytoplasmic tail. Subsequent activation of canonical and non-canonical nuclear factor-kB and c-Jun-N-terminal kinase (JNK)-signaling pathways follows to elicit cellular responses involving CD8$^+$ T-cell priming, proliferation, survival and cytotoxicity. On other cell types, CD70/CD27 interaction supports B-cell expansion in the germinal center. A subset of NK cells also express CD27, and here engagement of CD27 has been shown to increase IFNγ secretion albeit without a concomitant enhancement of NK cytotoxicity. The anti-tumor effect of CD27 ligation has been demonstrated in murine B-cell lymphoma and melanoma models, and preliminary results of the phase I studies of the anti-human CD27 mAb, varlilumab demonstrate that it is well-tolerated and has anti-tumor efficacy.

We show here that stimulation through CD27, unlike other immunomodulatory targets, greatly enhances anti-CD20 therapy in various pre-clinical models; translating to experimental cures. These studies reveal a novel mechanism through which agonistic CD27 mAb directly activate T and NK cells, leading to chemokine and cytokine release which drives the recruitment and activation of macrophages which upregulate activatory FcγRIV enabling more effective anti-CD20-mediated ADCP.

Results

Figure 11A:
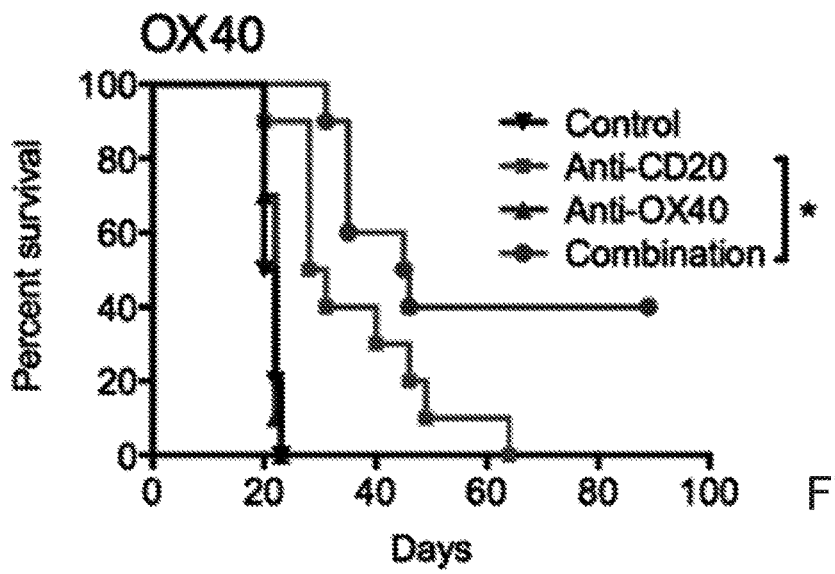
Figure 11B:
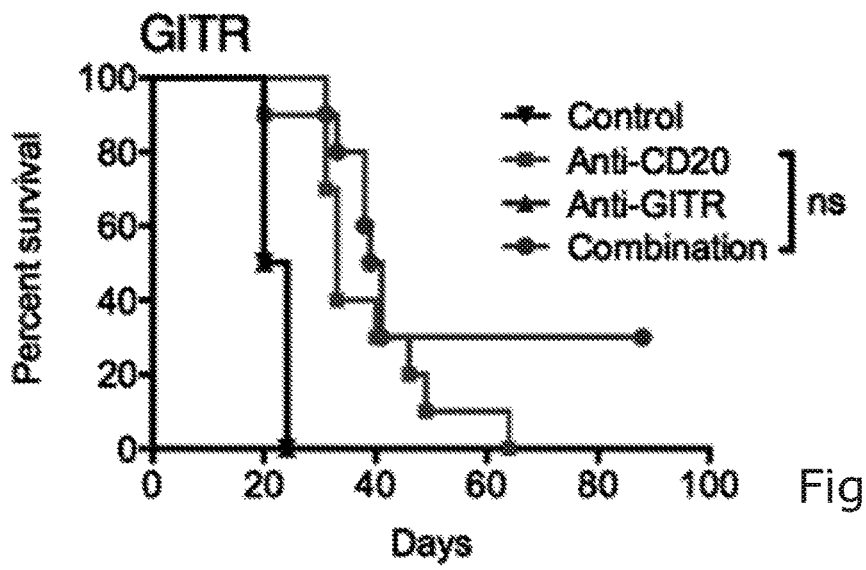
Figure 11C:
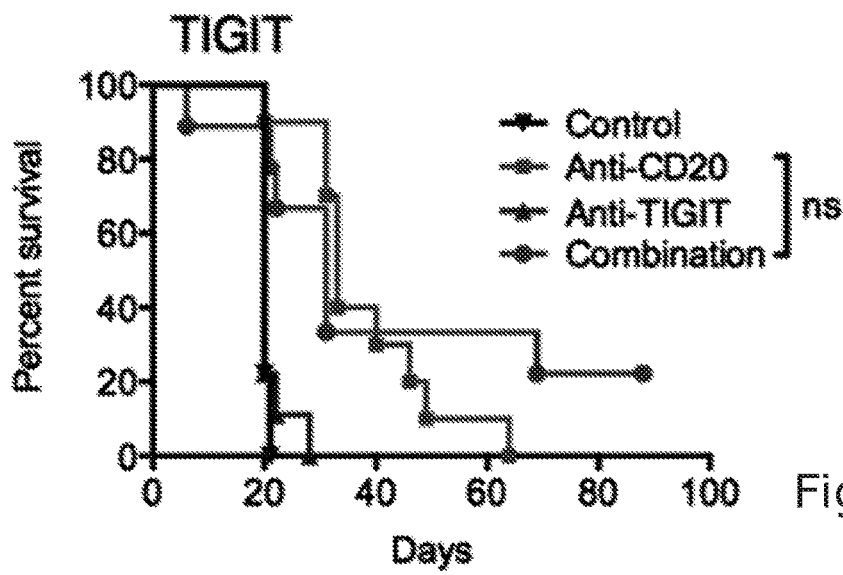
Figure 11D:
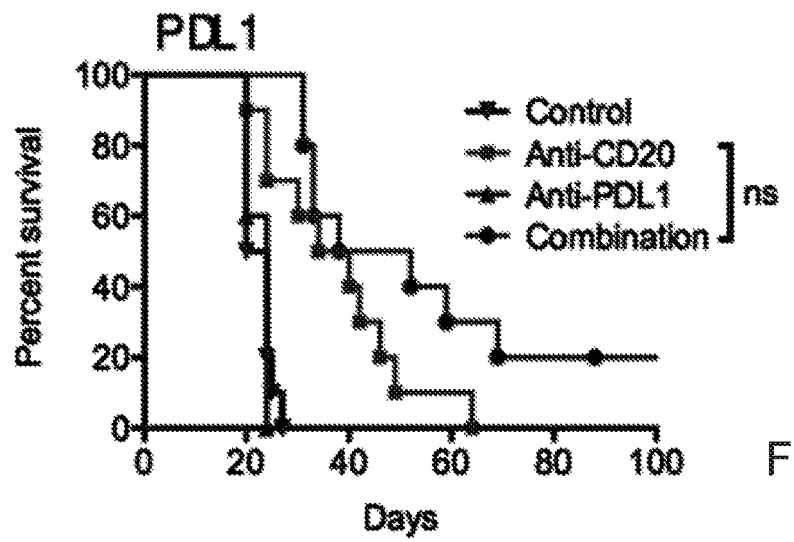
Figure 11E:
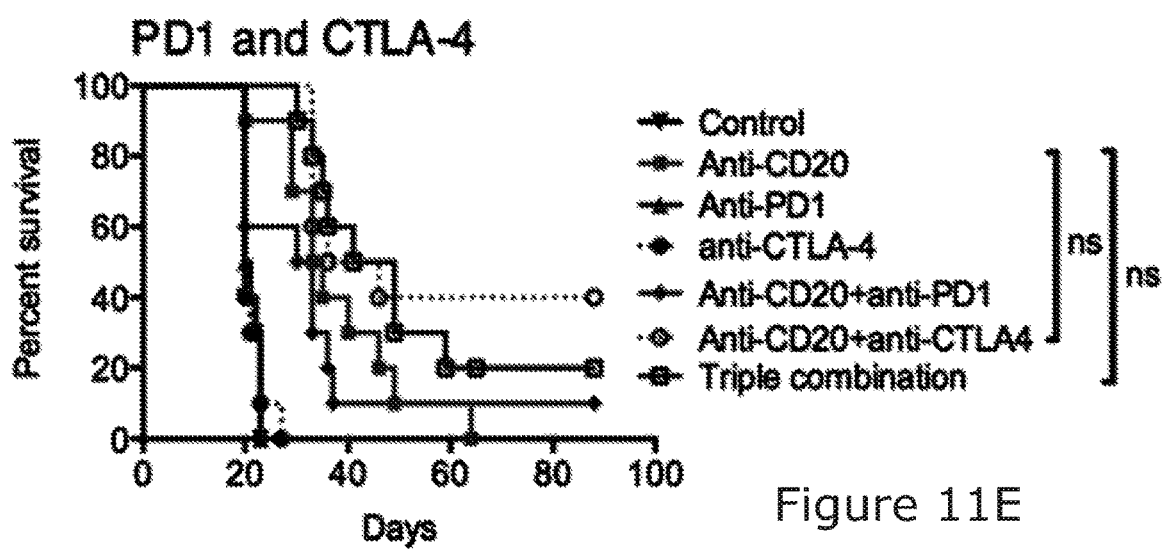
Figure 11F:
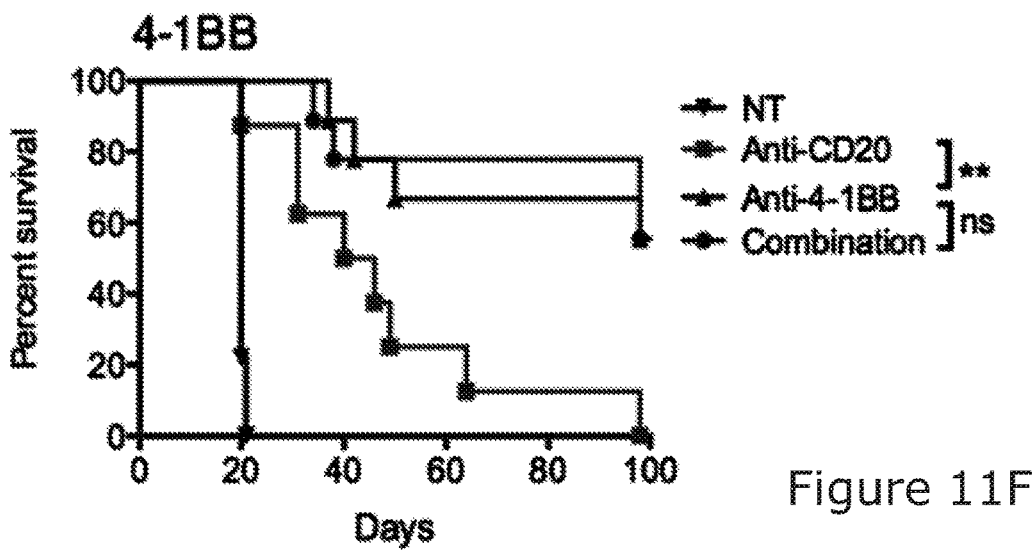

Combining Therapeutic CD20 mAb with Most Immunomodulatory mAb does not Result in Robust Improvements in Therapeutic Efficacy As an initial screening tool to investigate whether the therapeutic efficacy of anti-CD20 could be enhanced by combination with immunomodulatory mAbs we used the syngeneic, immunocompetent murine B-cell lymphoma model, BCL$_1$ (Slavin and Strober, 1978). Anti-CD20 was tested in combination with mAbs to costimulatory receptors, OX40, 4-1BB, GITR, and checkpoint blockers TIGIT, PD-L1, PD-1 or CTLA-4 (FIG. 11). Anti-CD20 mAb alone provided a modest survival benefit with a median survival of 29.5 days compared to 21 days with control mice (p<0.0001). When anti-CD20 was combined with the chosen immunomodulatory reagents, only anti-OX40 provided a modest benefit with a median survival of 45.5 days (FIG. 11A), with the other reagents providing small, non-statistical significant, improvements in tumor control. The 4-1BB mAb was highly effective as a single agent in this model with 56% of mice surviving beyond 100 days, but addition of anti-CD20 did not improve its therapeutic efficacy (FIG. 11F).

Anti-CD27 Enhances Direct Tumor Targeting mAb Therapy

Figure 12A:
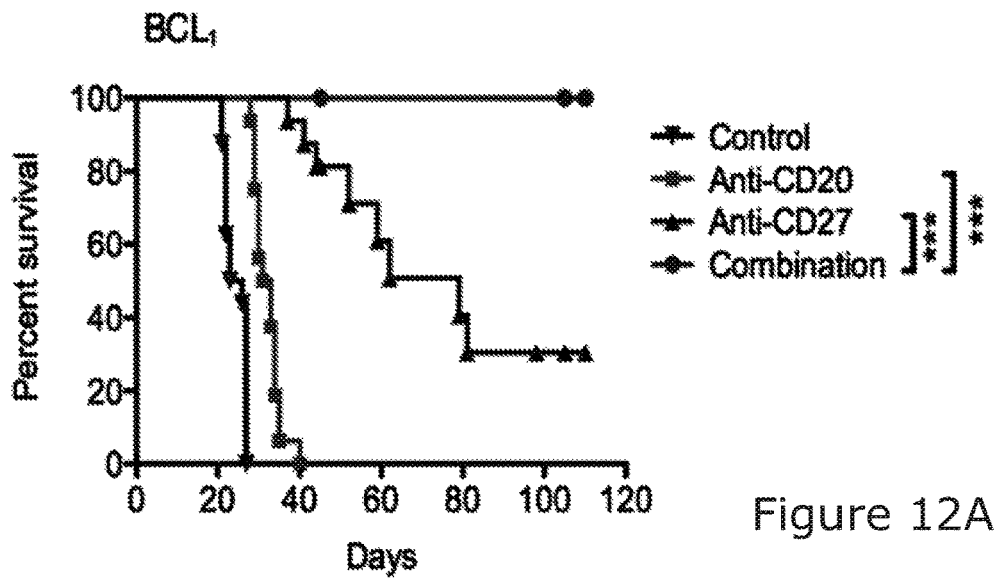
Figure 12B:
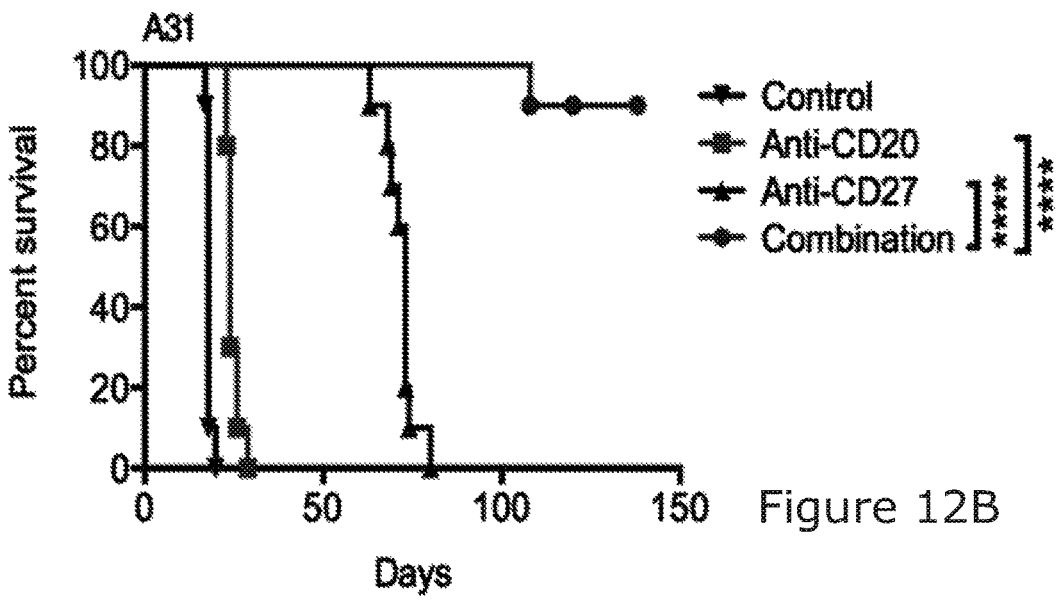

An agonistic mAb against CD27 was also tested with anti-CD20 in the same model (FIG. 12A). Anti-CD27-treated mice had improved survival compared to control or anti-CD20-treated mice (median survivals 24.5, 32 and 79 days in control, anti-CD20 and anti-CD27 groups, respectively). Most significantly, when given in combination with anti-CD20, 100% of the mice were cured beyond 100 days.

Figure 12C:
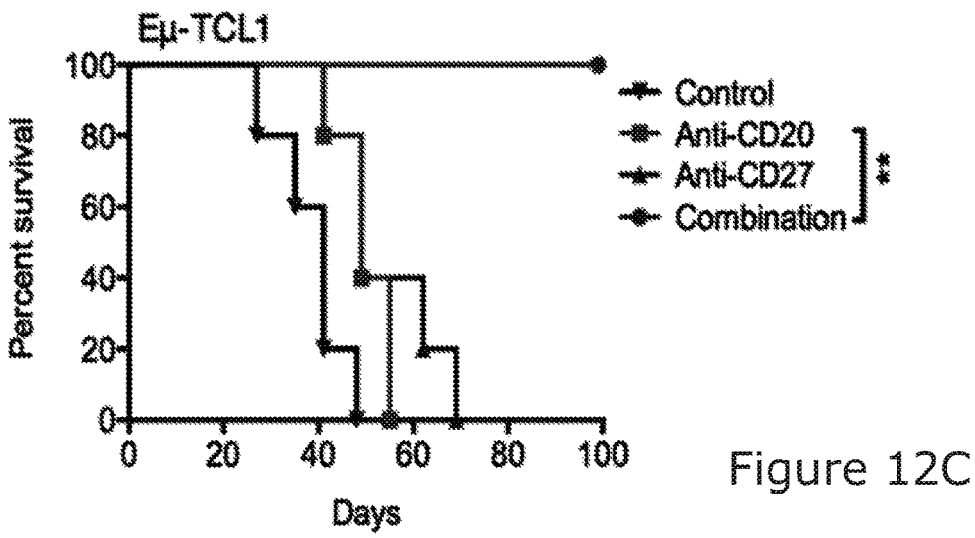
Figure 12D:
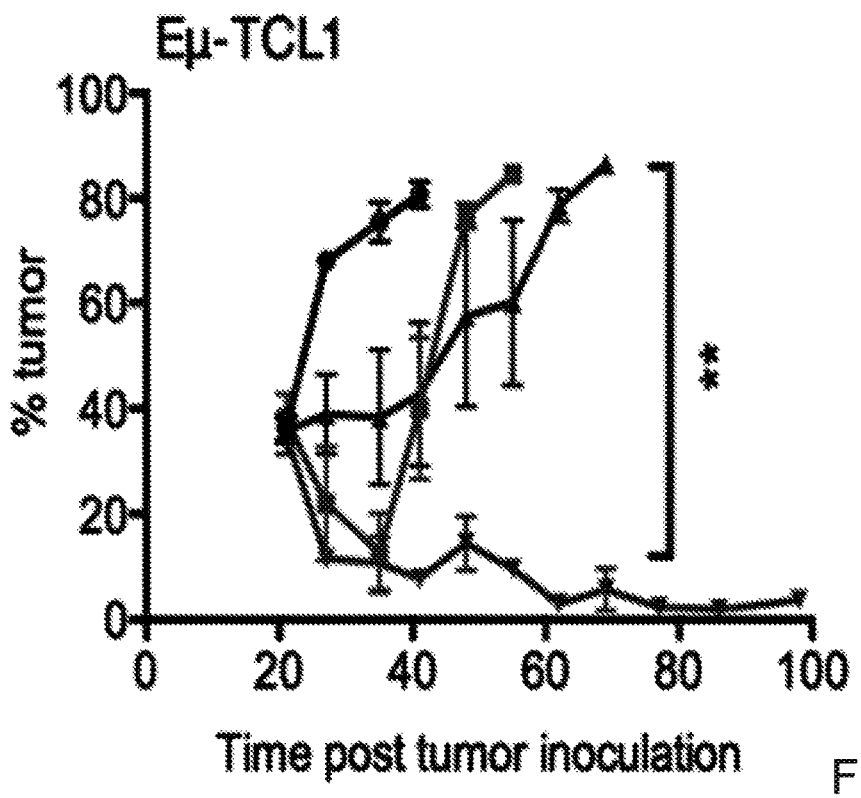
Figure 12E:
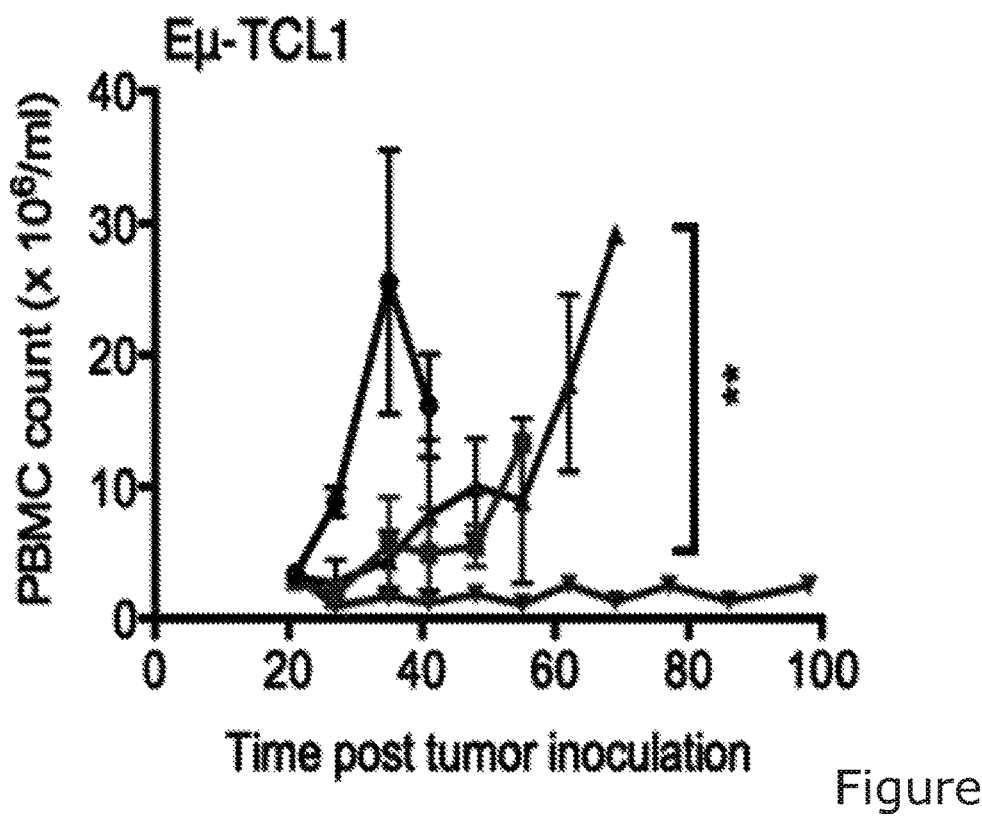

To ensure that the therapeutic benefit of anti-CD20/-CD27 therapy was not confined to the $BCL_1$ model, the combination was also tested in the A31 B-cell lymphoma (Cobb et al., 1986) (FIG. 12B), and Eμ-TCL1, B-chronic lymphocytic leukemia (B-CLL) (Bichi et al., 2002) models (FIG. 12C-E). In both models, anti-CD20 alone provided a modest therapeutic benefit (median survival 24 days in A31, and 49 days in Eμ-TCL1). Similarly, anti-CD27 alone also improved survival of tumor-bearing mice, particularly in the A31 model (median survival 73 days in A31, and 49 days in Eμ-TCL1). However, in combination, a significant improvement was observed, with almost all mice surviving beyond 100 days. In the Eμ-TCL1 model, we observed that protection provided by either anti-CD20 or anti-CD27 alone was minimal (FIG. 12D), yet the combination delivered efficient tumor and B-cell depletion.

These investigations demonstrate that agonistic anti-CD27 can improve the anti-tumor efficacy of a direct tumor targeting mAb to B-cell lymphoma in a way not seen with other immunomodulatory mAb.

Combination Therapy is not Entirely Dependent on T Cells

Our subsequent investigations aimed to dissect the mechanism by which anti-CD27 enhances anti-CD20 therapy. First, we examined the expression of CD27 on the B-cell tumors examined, alongside potential immune effectors (FIG. 18). Anti-CD27 did not bind to $BCL_1$, A31, or Eμ-TCL1, and so is not acting as a direct tumor targeting mAb, but consistent with previous reports, CD27 was expressed constitutively on NK cells and all subsets of T cells.

Figure 13A:
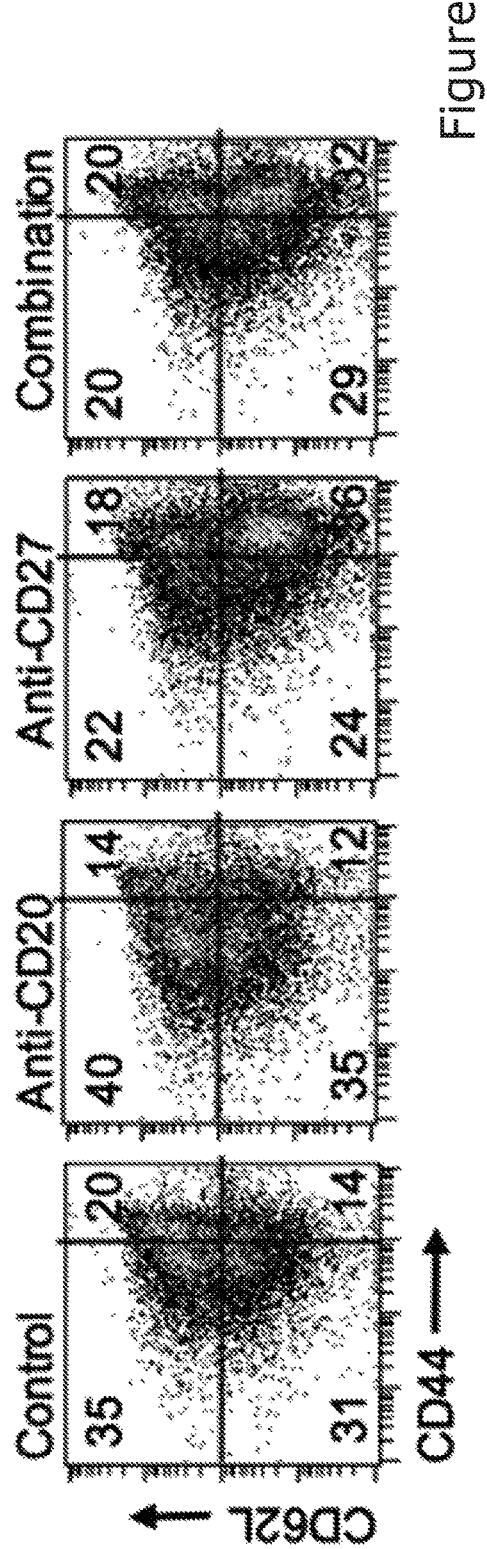
Figure 13B:
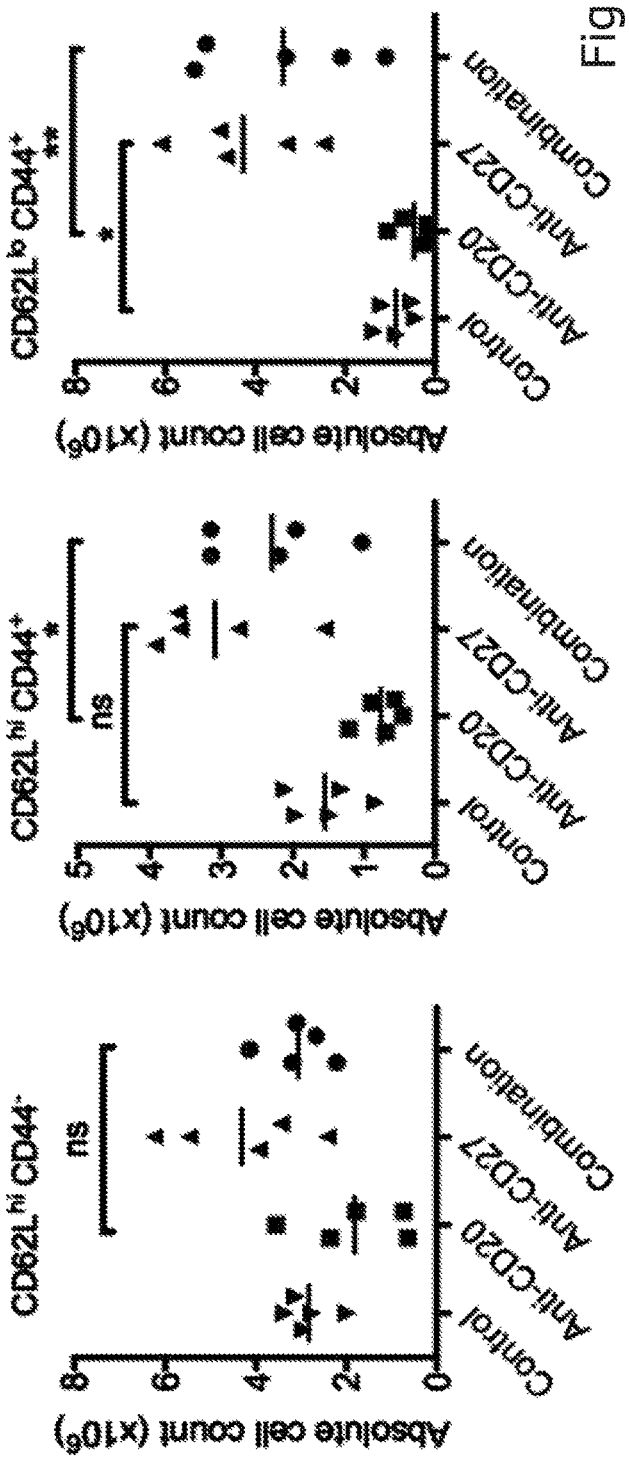
Figure 13C:
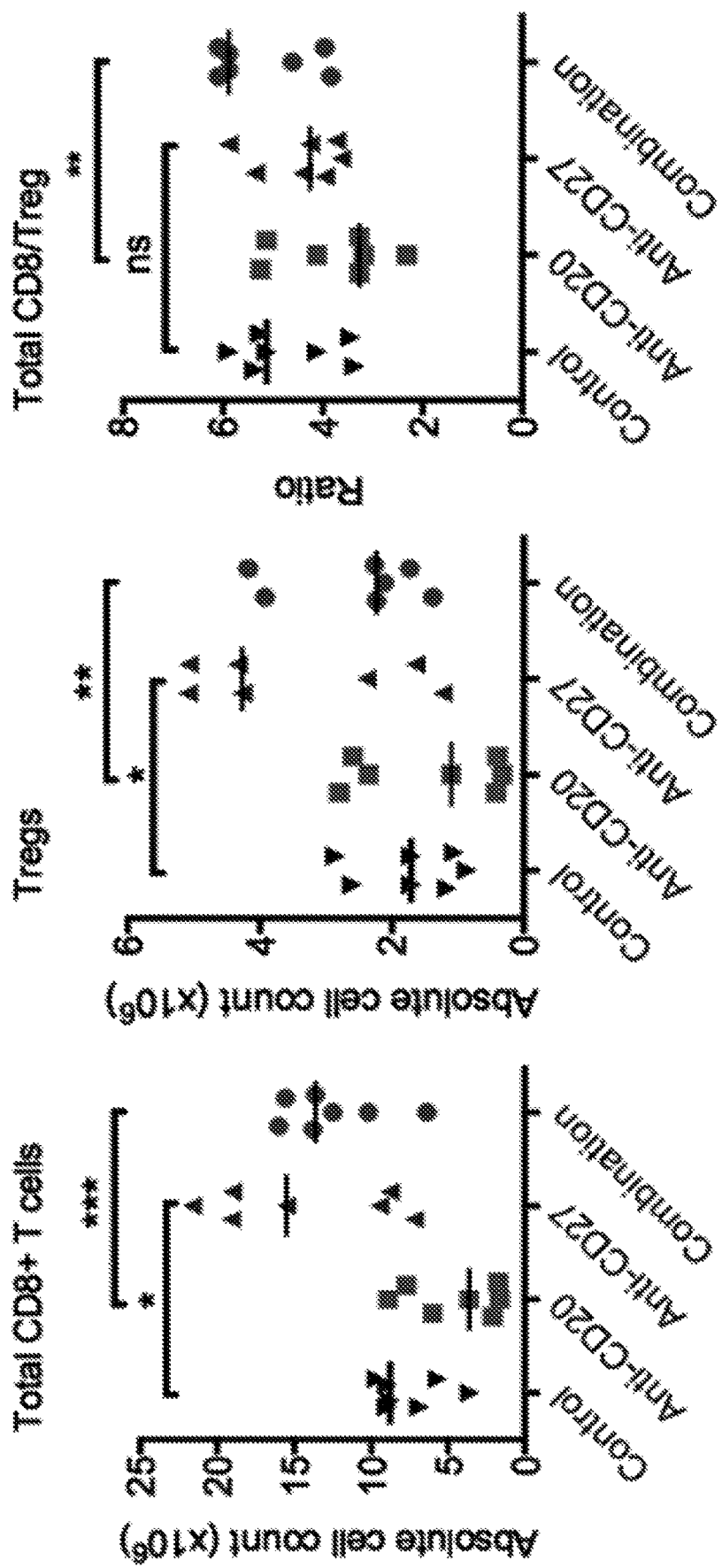

Given that CD27 is a well-described co-stimulatory receptor on T cells, we examined the effect of T cells in the $BCL_1$ model. $BCL_1$-bearing BALB/c mice treated with anti-CD27 and anti-CD20/-CD27 have nearly 3-fold more activated CD8$^+$ T cells (as defined by CD62L$^{hi}$ CD44$^+$ and CD62L$^{lo}$ CD44$^+$) in the spleen than control and anti-CD20-treated mice on day 13 (FIGS. 13A and 13B). Further, on day 13, there was a significant increase in the number of CD8$^+$ T cells in the anti-CD20/-CD27 group compared to anti-CD20 alone (median 13.6×10$^6$ vs 3.6×10$^6$, respectively) (FIG. 13C). A marked increase in CD8$^+$ T cell count was also observed with anti-CD27 alone (median 15.6×10$^6$), and this was significantly different compared to the control group (median 8.8×10$^6$). Increased numbers of regulatory T cells (Tregs) were also observed with anti-CD27- and combination-treated groups, but the total CD8$^+$/Treg ratio between combination and control-treated groups and their respective controls were not different (medians 5.9 and 5.1, respectively).

Figure 13D:
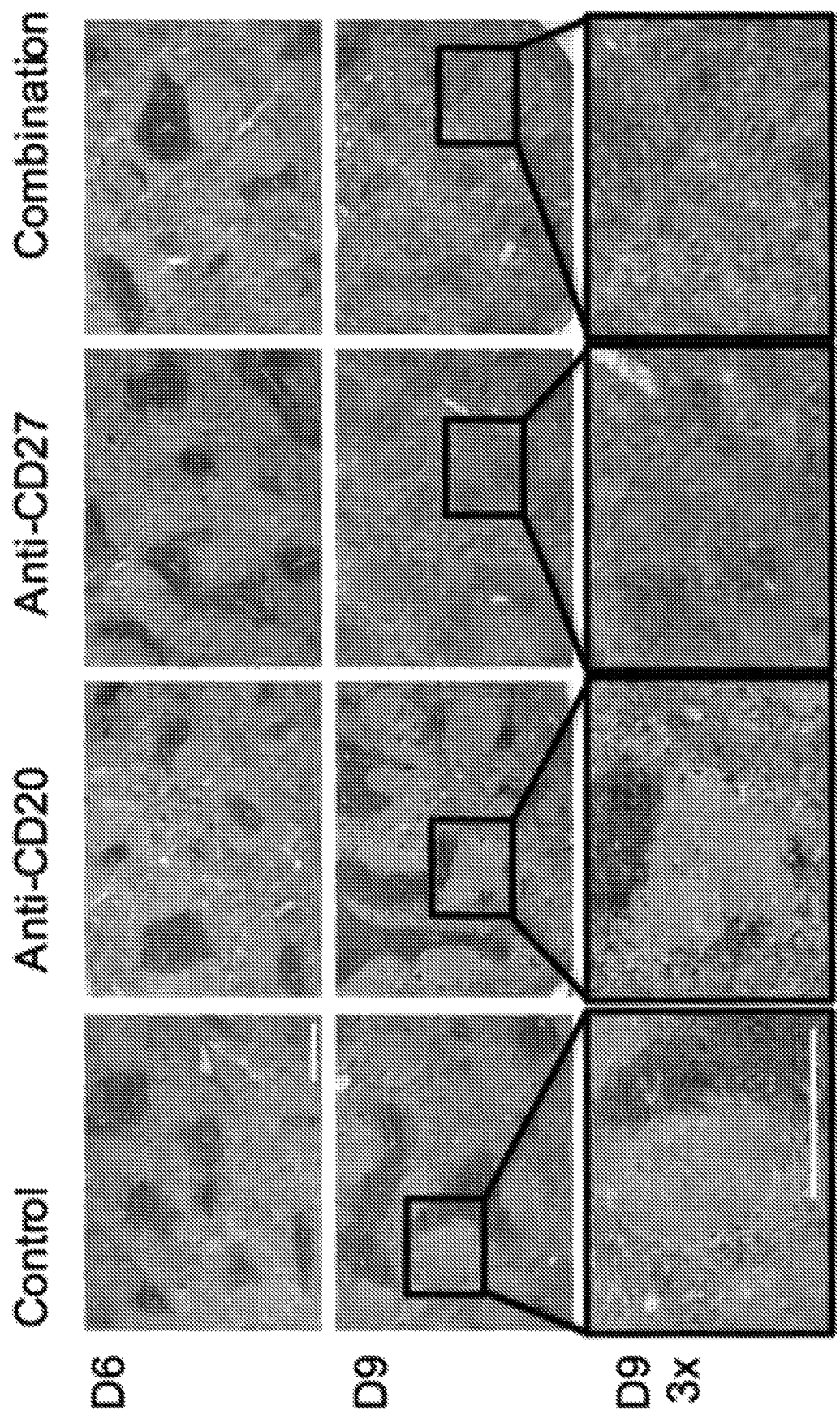

When the spleens of control and treated $BCL_1$-bearing animals were examined on days 6 and 9 for CD8$^+$ cells by immunohistochemistry, a change was observed in the pattern of CD8 staining (FIG. 13D). In control and anti-CD20 treated mice, CD8$^+$ staining was confined to the interfollicular regions. In contrast, in anti-CD27 and combination treated mice, staining was observed in both the interfollicular and follicular regions on day 6, and throughout the whole spleen on day 9. This demonstrates that anti-CD27 given alone, or in combination with anti-CD20, alters CD8$^+$ T cell distribution.

Figure 13E:
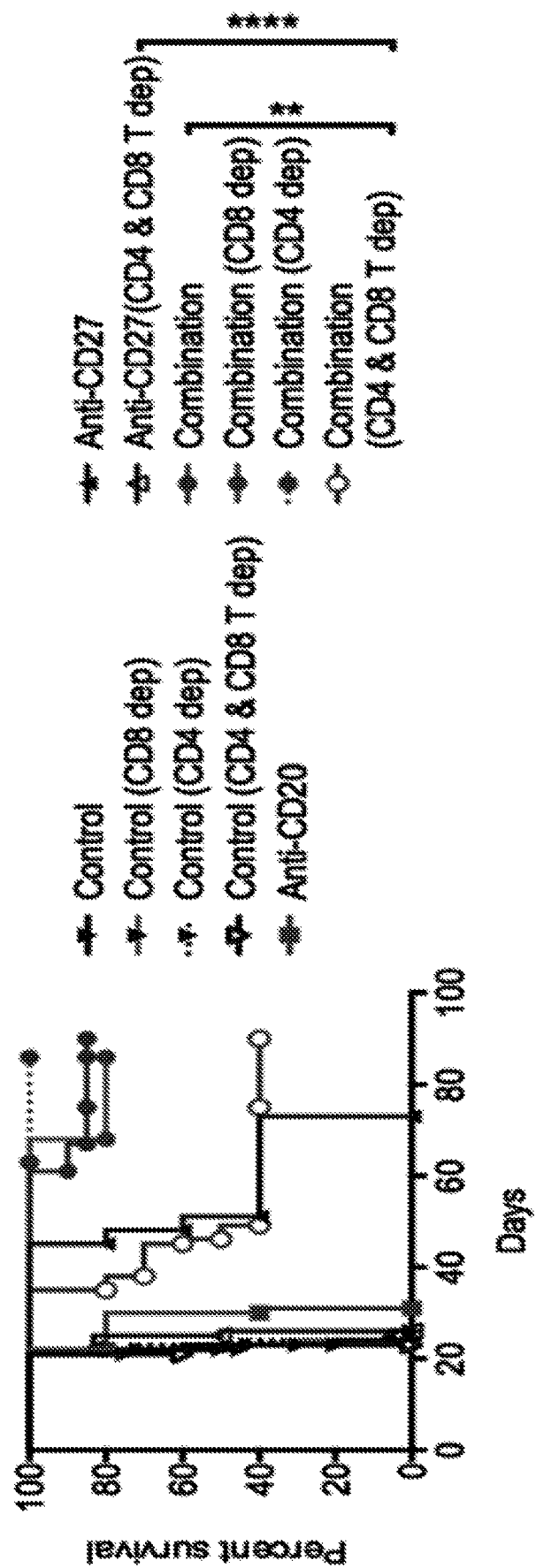
Figure 13F:
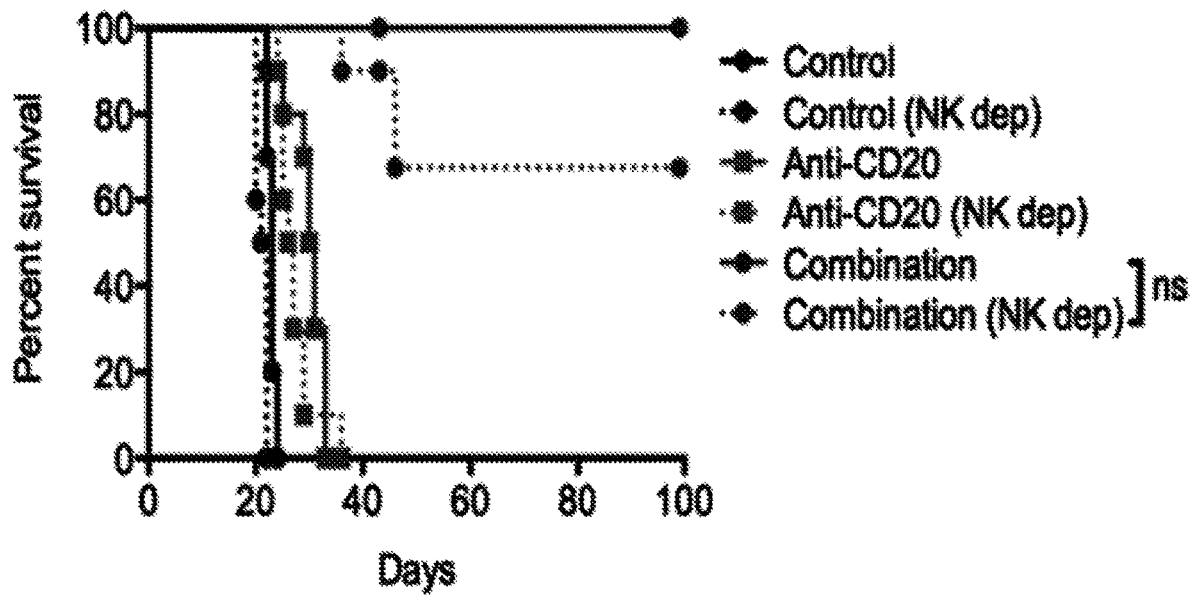

Altogether, this suggests that anti-CD27's anti-tumor effect is in part mediated by CD8$^+$ T cells. To assess their contribution to the immunotherapy in the $BCL_1$ model we depleted CD4$^+$, CD8$^+$ or both CD4$^+$ and CD8$^+$ T cells (FIG. 13E). As expected, deletion of both CD4$^+$ and CD8$^+$ T cells completely abrogated anti-CD27 monotherapy. Deletion of either CD4$^+$ or CD8$^+$ alone had minimal impact, but deletion of both CD4$^+$ and CD8$^+$ T cells together reduced therapeutic efficacy of combination therapy, albeit not entirely. This suggests that whilst T cells are important, additional mechanisms of tumor killing compensate for the loss of T-cell cytotoxicity.

Anti-CD20/-CD27 Combination Therapy Requires NK Cells

The other main population of immune effector cells that express CD27 are NK cells, so we explored the ability of anti-CD27 to activate these cells in vivo. Naïve wild type (WT), FcγRIII−/− or SCID mice were treated with a single dose of anti-CD27 and the expression of the activation marker, KLRG1, was monitored on peripheral blood NK cells (FIG. 19). Treatment with anti-CD27 or anti-CD20/-CD27 resulted in a ~20% increase in KLRG1$^+$ NK cells compared to controls in WT mice. A similar level of increase was also observed in FcγRIII−/− mice indicating that NK activation occurred directly via CD27 and not via Fc-FcγR binding (through FcγRIII). Equally, the increase of KLRG1$^+$ NK cells in SCID mice also indicates that NK activation does not occur indirectly via CD27-mediated T-cell activation as T cells are absent in these mice.

To directly investigate the contribution of NK cells to therapy, they were depleted in the $BCL_1$ model (FIG. 13F) using appropriate doses and formulations of anti-asialo GM1(Turaj et al., 2017). NK depletion alone did not significantly alter the survival of control or anti-CD20 treated mice. However, there was a modest impairment of survival in the combination-treated mice after NK depletion compared to non-depleted mice (p>0.05). Thus, akin to T cells, anti-CD27 directly activates NK cells but anti-CD20/-CD27 therapy is not entirely dependent on either cell-type alone.

Figure 13G:
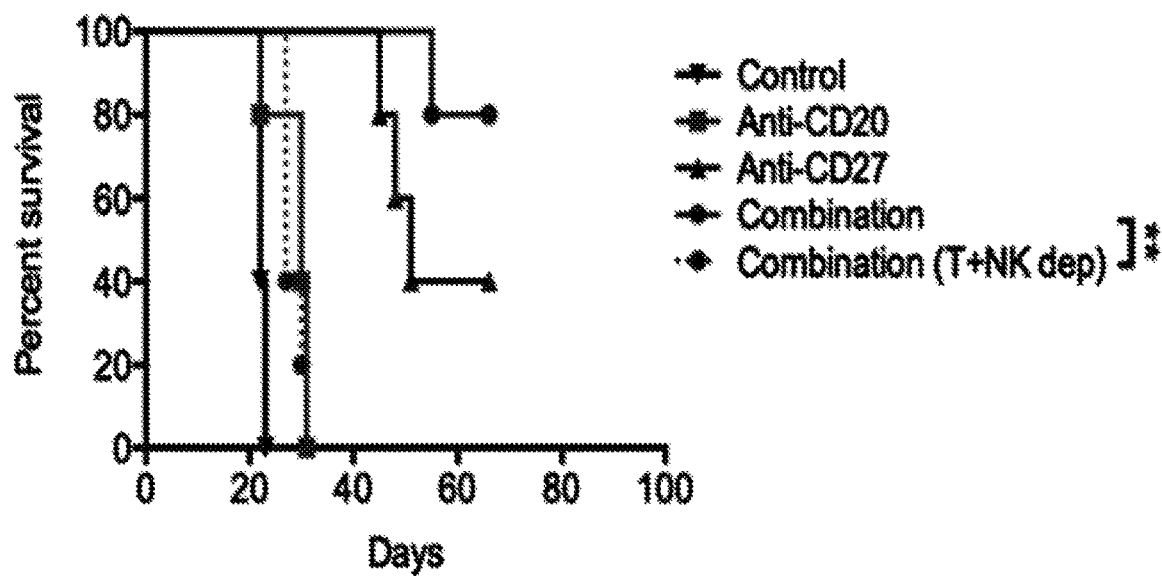

However, when NK and T cells were simultaneously depleted, the therapeutic benefit of adding anti-CD27 to anti-CD20 was abrogated, such that the mice had the same median survival as anti-CD20 mice alone (control 22 days, anti-CD20 30 days, combination with T and NK depletion, 27 days) (FIG. 13G). Thus, the therapeutic efficacy of anti-CD20/-CD27 therapy requires either T or NK cells to help mediate tumor control by anti-CD20 by a hitherto unknown mechanism.

Anti-CD27 Promotes Intratumoral Myeloid Cell Infiltration

Figure 14A:
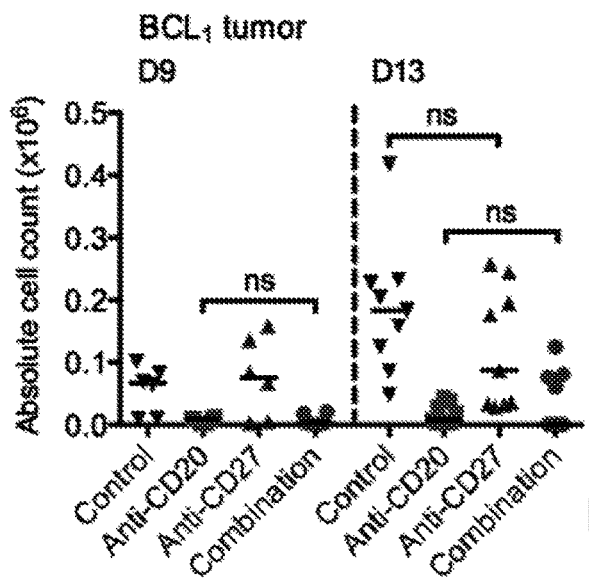
Figure 14B:
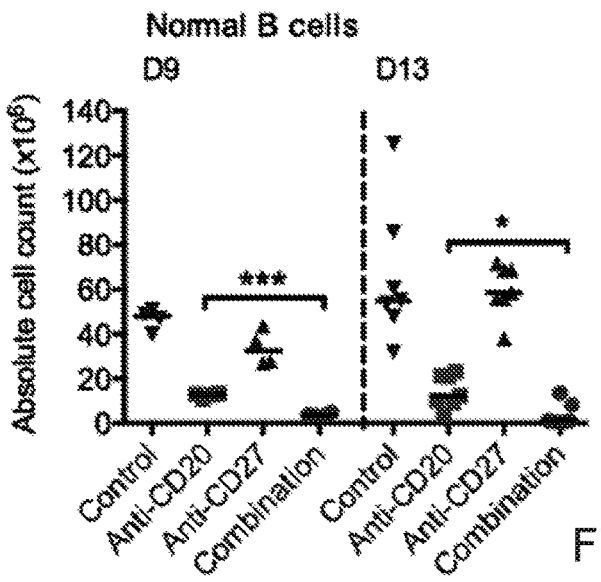
Figure 14C:
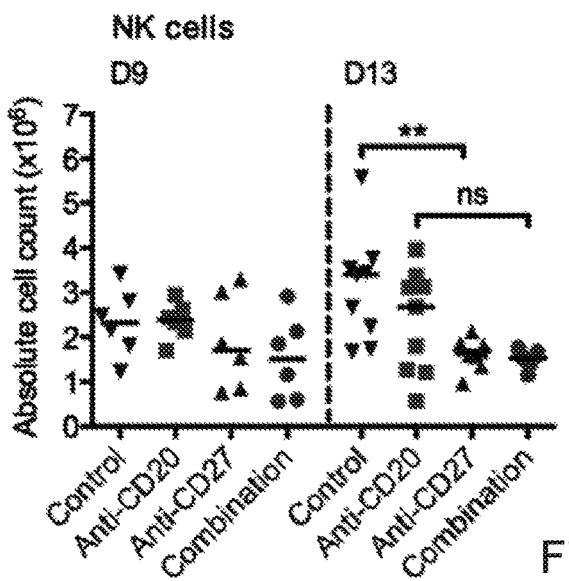

It is recognized that anti-CD20 mediated ADCP is carried out by myeloid cells. FIGS. 12D and E shows that there is a greater level of B-cell depletion when anti-CD27 is combined with anti-CD20 in the Eμ-TCL1 model. We sought to validate these findings in the $BCL_1$ model, and to examine whether anti-CD27 altered the myeloid compartment. Spleens of $BCL_1$-bearing mice were harvested on days 9 or 13 after tumor inoculation, and tumor cells, normal B cells, NK cells, macrophages, monocytes and neutrophils enumerated by flow cytometry (FIGS. 14A-F). Consistent with the observations in the Eμ-TCL1 model, anti-CD20 rapidly depleted malignant and normal B cells whilst minimal difference was seen in the tumor load between control and anti-CD27-treated mice at these time-points (FIGS. 14A and 4B). Combined anti-CD20/-CD27 therapy was more effective than anti-CD20 alone in depleting B cells, most evidently with normal B cells at day 9 ($13.0 \times 10^6$ vs $3.6 \times 10^6$ normal B cells, anti-CD20 vs combination) (FIG. 14B). We observed a trend towards reduction in splenic NK cells with anti-CD27 and combined anti-CD20/-CD27 treatment compared to controls, most noticeably on day 13 (medians $3.8 \times 10^6$, $2.7 \times 10^6$, $1.7 \times 10^6$, $1.5 \times 10^6$ cells in control, anti-CD20, anti-CD27 and combination groups, respectively) (FIG. 14C), which is recognized following NK activation.

Figure 14D:
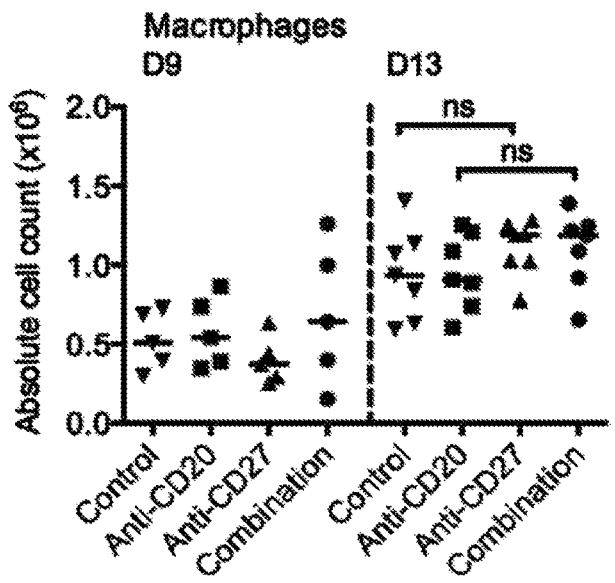
Figure 14E:
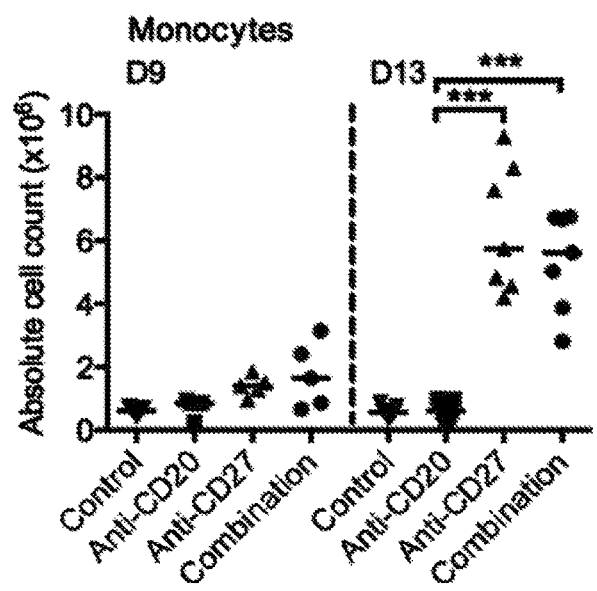
Figure 14F:
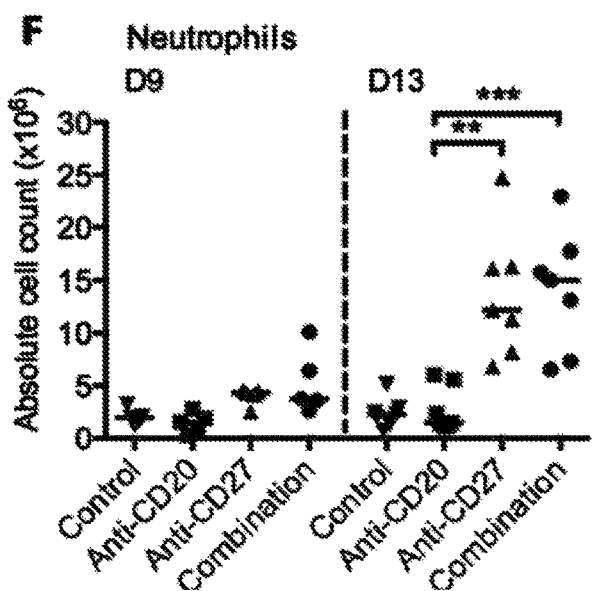
Figure 14G:
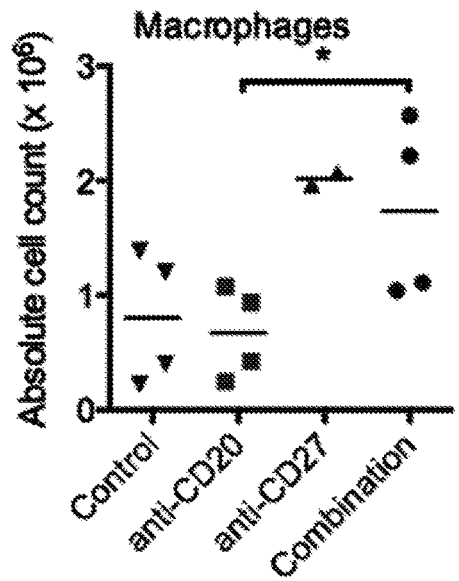
Figure 14H:
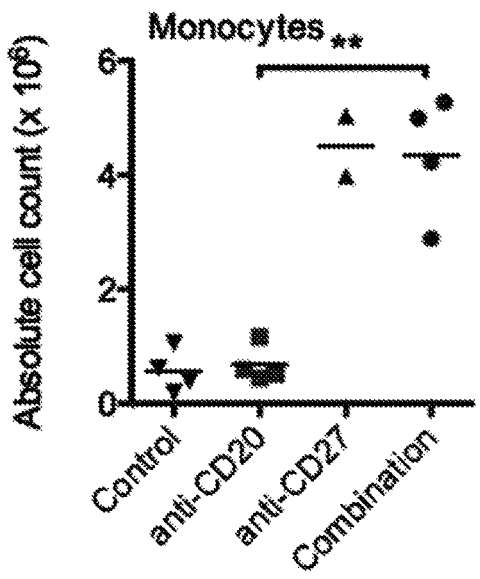
Figure 14I:
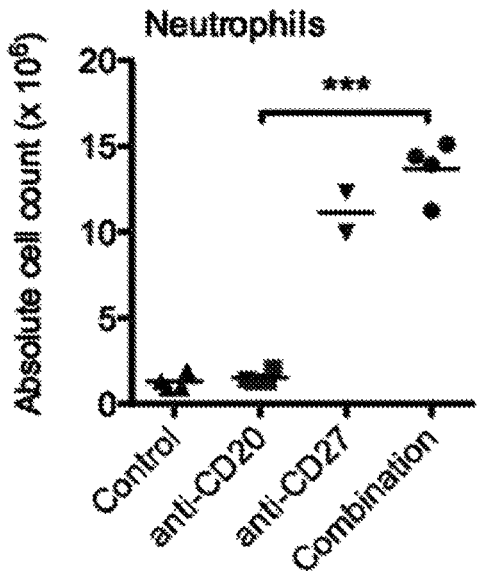

Examination of the myeloid compartment in the spleen at the same time points demonstrated increased numbers of macrophages on day 13 compared to day 9 across all treatment groups (FIG. 14D). On day 13, there were non-significant trends towards higher numbers of macrophages in the groups receiving anti-CD27 or in combination (medians $1.8 \times 10^6$, $1.2 \times 10^6$, $0.9 \times 10^6$, $0.9 \times 10^6$, respectively) but marked increases in monocytes and neutrophils (FIGS. 14E and 15F).

A similar trend of increased myeloid cell infiltration was also observed in the spleen when the experiment was repeated in naïve non-tumor bearing mice (FIG. 14G-I), indicating that these changes are CD27-related and not tumor-driven. In this case, macrophage numbers were also significantly elevated in the combination compared to anti-CD20 alone.

Figure 14J:
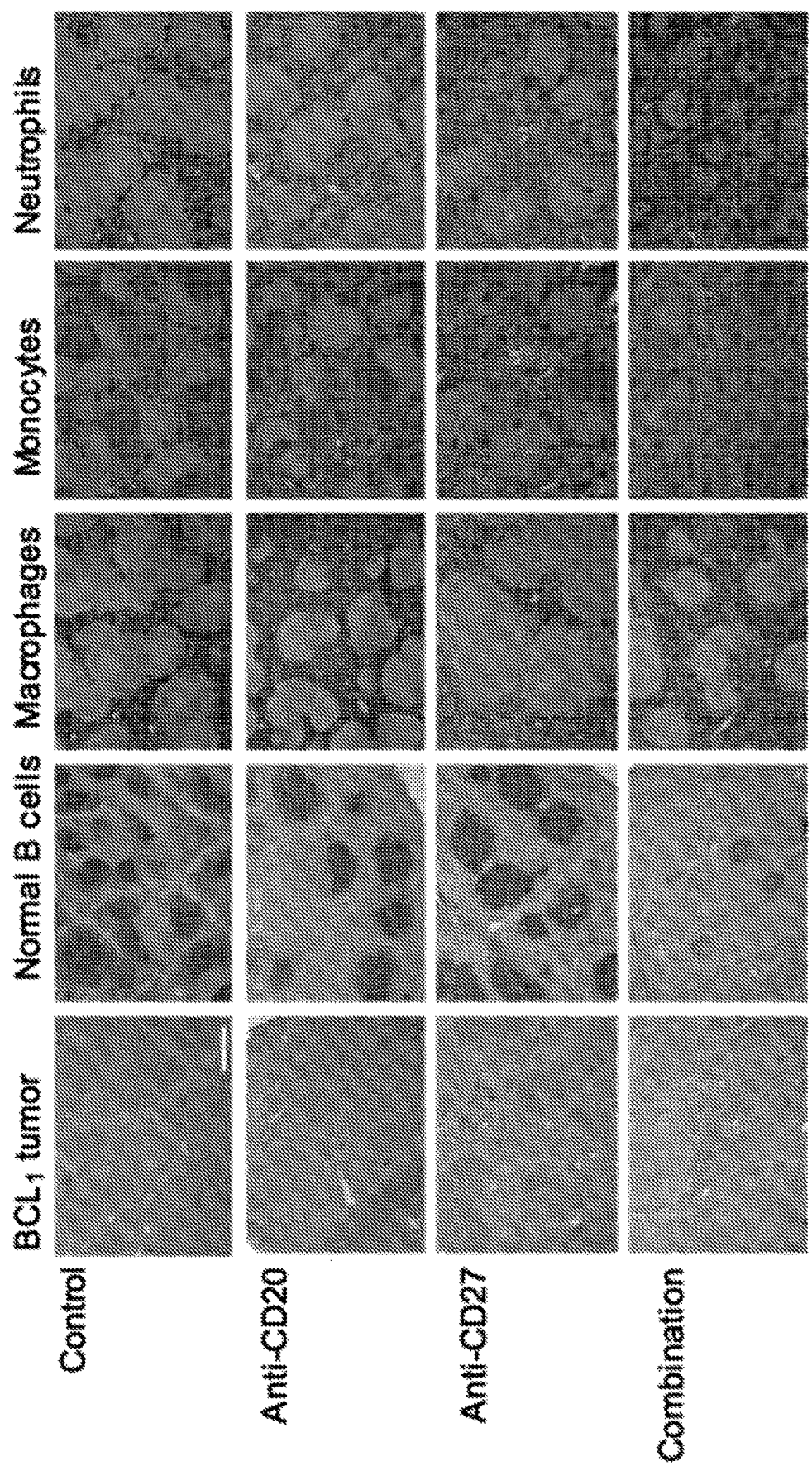

The spleens of $BCL_1$-bearing mice were also examined by immunohistochemistry on day 9 (FIG. 14J). At this time point, the tumor burden is still low (FIG. 14A) and the splenic architecture preserved, allowing changes to other cell populations to be appreciated. FIG. 14J shows clear evidence of depletion of B cells by anti-CD20, and that this is enhanced by the addition of anti-CD27. Consistent with the flow cytometry data (FIGS. 14E and 14F), there was clearly increased monocyte and neutrophil staining in anti-CD27 and anti-CD20/-CD27 groups, but no obvious increase in macrophages at this early time-point.

To determine if neutrophils were the cellular effectors of anti-CD20 mediated B cell deletion, we depleted these cells in naïve mice, and examined the ability of anti-CD20+/−anti-CD27 to deplete B cells from the spleen (FIGS. 20A and 3B). Neutrophil depletion alone had minimal effect on B-cell depletion in both treatment groups. Macrophage depletion was also performed using liposomal-encapsulated clodronate but depletion of macrophages itself slows $BCL_1$ tumor growth, thus preventing us from assessing the contribution of macrophages in anti-CD20/-CD27 therapy (FIG. 20C). However, we and others have previously shown that macrophages are the main effectors of anti-CD20 mediated B-cell depletion.

Anti-CD27 Indirectly Promotes Infiltration and Activation of Myeloid Cells

Figure 15A:
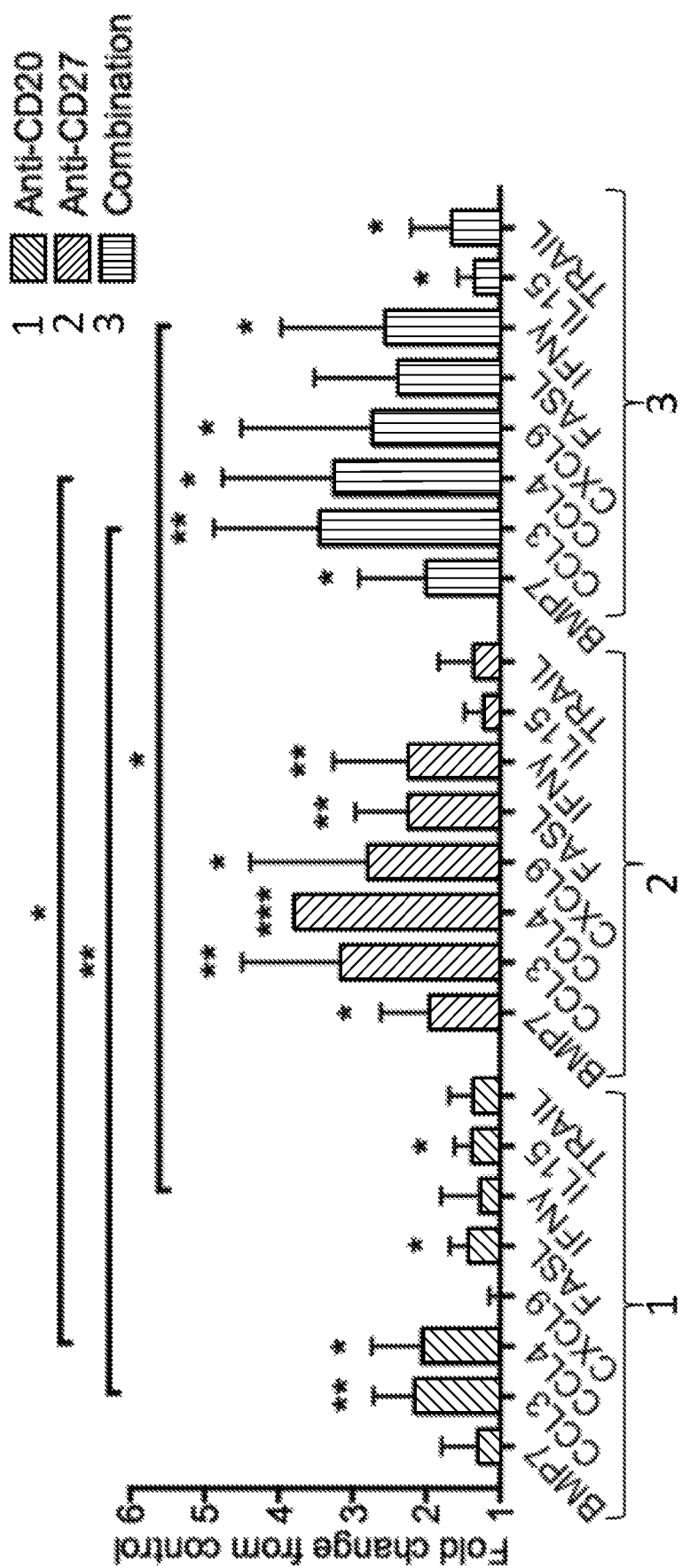

CD27 is not expressed on macrophages, monocytes or neutrophils (FIG. 20D), ruling out direct activation of these cells by anti-CD27. We therefore hypothesized that upon activation by anti-CD27, T and NK cells release chemokines and cytokines that attract and activate macrophages. To investigate this, naïve mice were treated with anti-CD20, anti-CD27 or the combination, mRNA isolated from the spleens, and analyzed with a chemokine and cytokine gene expression array. A heatmap was constructed demonstrating the experimental conditions and the normalized Ct values for each gene (FIG. 21). Genes that were significantly upregulated (p>0.05) in anti-CD27 and/or combination arms in comparison to the control group are shown in FIG. 15A. We observed increased expression of FAS ligand, TRAIL and IFNγ in mice treated with anti-CD27+/−anti-CD20, supportive of increased T and/or NK cytotoxicity. CXCL9 which is associated with a $T_H1$ response, and T-cell trafficking was also increased, in line with the changes observed in FIG. 13D. Conversely, no significant change was observed cytokines associated with $T_H2$ responses, such as IL4, IL5 and IL13 (FIG. 21).

Figure 15B:
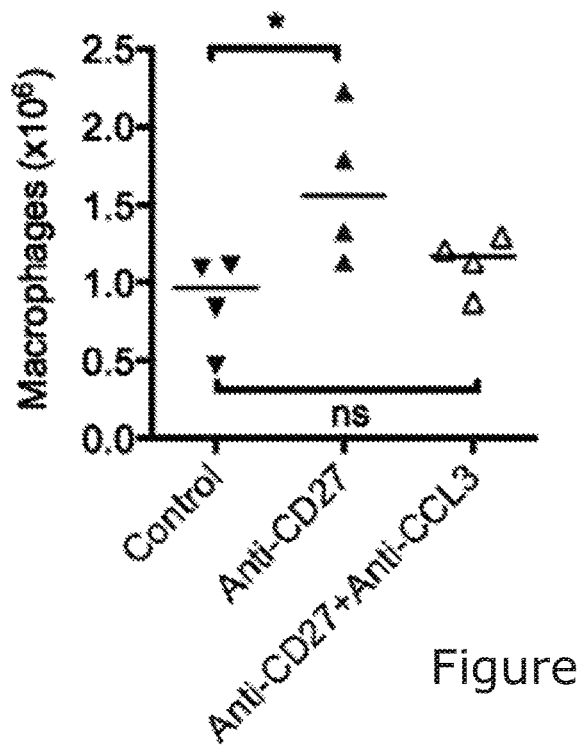

Furthermore, chemokines associated with myeloid cell trafficking such as CCL3 and CCL4 were raised in mice treated with anti-CD20, anti-CD27 and the combination. We validated the importance of CCL3 by neutralizing this chemokine in mice treated with anti-CD27 (FIG. 15B). Increased macrophage infiltration was observed in naïve mice with anti-CD27 administration, but macrophage infiltration reduced upon CCL3 neutralization thereby indicating that CCL3 is in part responsible for attracting macrophages.

Figure 15C:
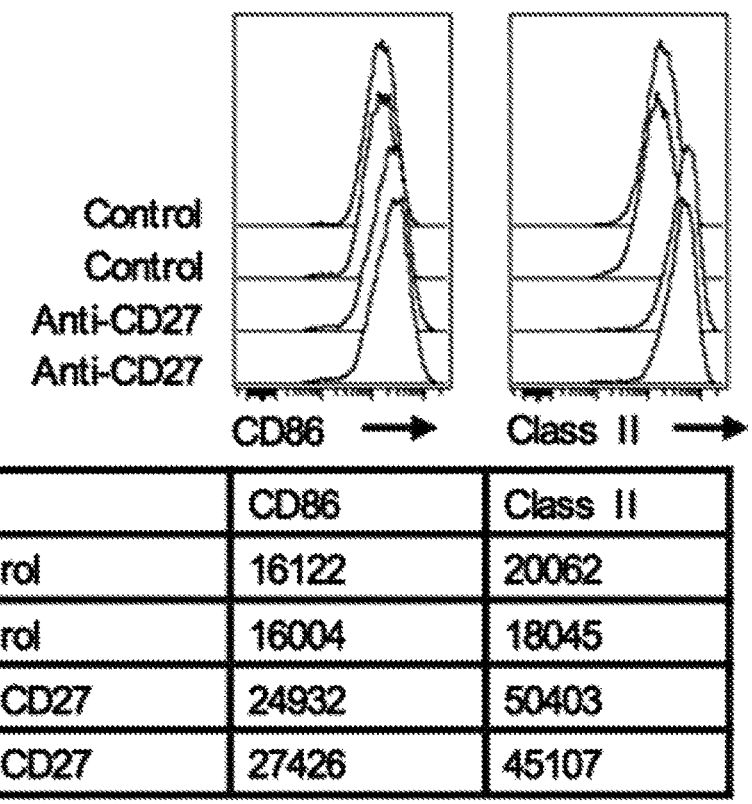
Figure 15D:
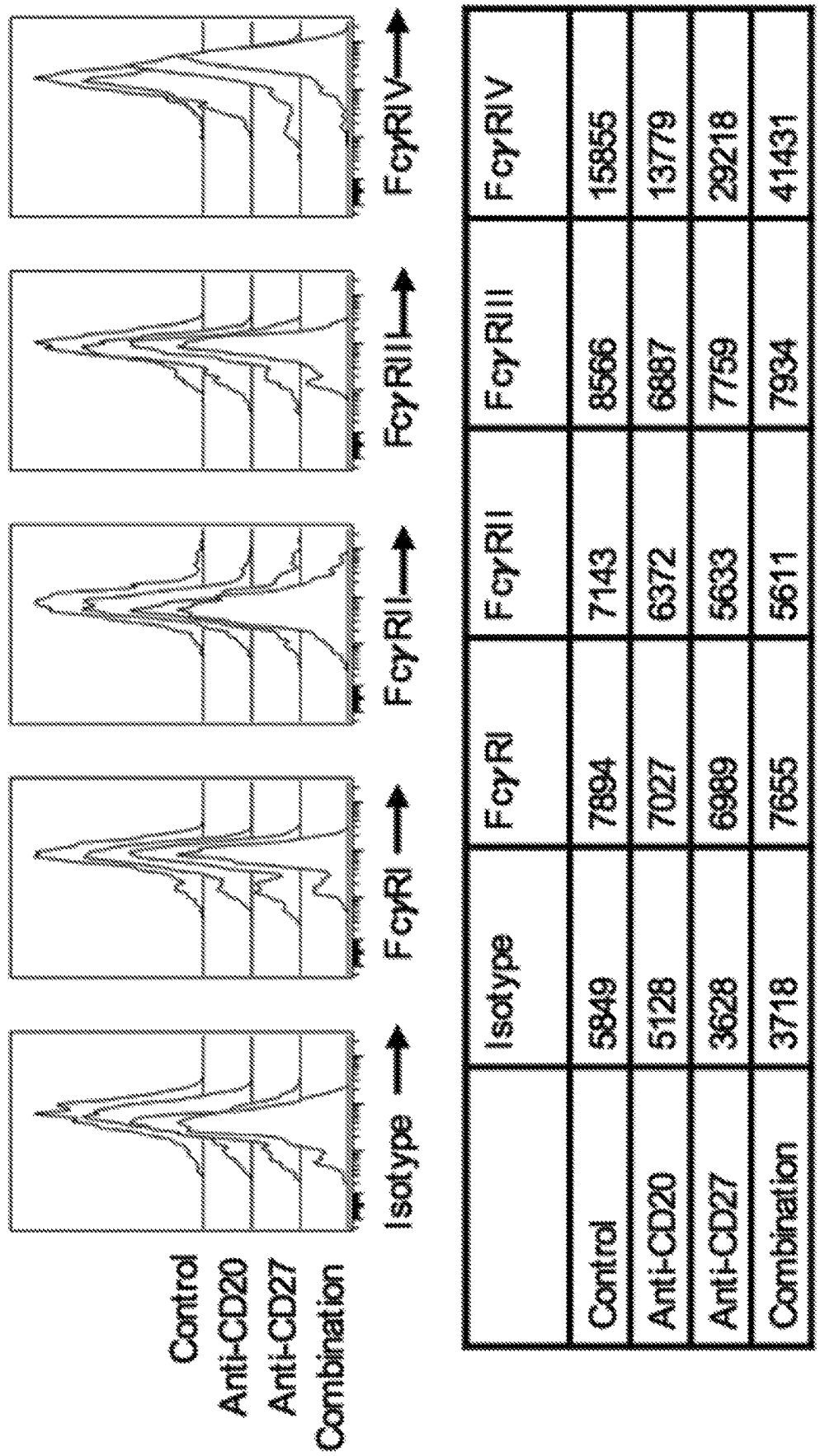

It is recognized that macrophages are phenotypically and functionally plastic, and have the capacity to both kill tumor and promote its development. Simplistically and at the extreme ends of a spectrum, macrophages can be divided into 'M1-anti-tumor' or 'M2-immunosuppressive' phenotypes, with M1 more effective at ADCP. The upregulation of IFNγ and CXCL9 by anti-CD27, and combination therapy (FIG. 15A) indicate that these treatments polarize the macrophages towards an M1 phenotype. Consistent with this data, mice treated with anti-CD27 also upregulate CD86 (1.6-fold) and Class II (2.5-fold) on macrophages (FIG. 15C). Furthermore, in the $BCL_1$ tumor microenvironment, anti-CD27 and anti-CD20/-CD27 also increased the expression of the activating Fc receptor, FcγRIV (FIG. 15D), a key FcγR involved in mediating ADCP on murine macrophages, by 1.8-fold compared to control mice (FIG. 15D). In combination treatment, FcγRIV increased by 3-fold compared to anti-CD20-treated mice. No obvious changes were observed in the expression of FcγRI, FcγRII or FcγRIII. Thus, anti-CD27 and combination therapy has a two-fold effect on macrophages. First in polarizing them towards an M1 anti-tumor phenotype, and secondly, in increasing ADCP capacity by increasing FcγRIV expression.

To identify further cell-type specific changes elicited by anti-CD27 treatment, single cell RNA sequencing was performed on cells isolated from spleens of $BCL_1$-bearing mice (day 13), treated as previously described (FIGS. 16 and 22). We observed a number of changes consistent with the flow cytometry and PCR array data. First, there was a striking absence of B cells with the combination arm, when compared to anti-CD20 alone (FIG. 16B), indicative of enhanced B cell depletion with combination therapy. Second, granulocytes, macrophages and effector $CD8^+$ T cells were markedly increased in anti-CD27 and combination arms, as shown by the higher cell counts (FIG. 16B) and expression of the proliferation marker, Ki67 (FIG. 22A) in these populations. Chemokines associated with myeloid cell infiltration, specifically CCL3 (FIG. 16C), CCL4 (FIG. 22B) and CCL5 (FIG. 22C) were upregulated on anti-CD27 and combination treatment. All three chemokines were primarily expressed in effector $CD8^+$ T cells, with lower levels of expression on NK cells. CXCL9 was also upregulated in macrophages with anti-CD27 and combination therapy (FIG. 22D). The upregulation of IFNγ (FIG. 22E) observed in the PCR array, was also observed here with anti-CD27 and combination therapy, and seen in effector CD8+ T cells, with some expression in NK cells. Strong Fcgr4 expression (the gene encoding FcγRIV) was observed in the granulocyte and macrophage populations (FIG. 22F), which also displayed upregulation of interferon response genes, Ifitm3 and Isg15 (FIGS. 16D and 16E).

Altogether, these data show that anti-CD27 activates CD8+ T cells, and to a lesser extent NK cells, to release CCL3, CCL4 and CCL5 to increase myeloid cell infiltration. The infiltrating myeloid cells are activated, potentially by IFNγ secreted by CD8+ T and NK cells and possess increased ADCP capacity, as shown by increased FcγRIV expression.

Anti-huCD27 mAb Displays Similar Activity

To confirm that these findings have relevance to human CD27 and could be translated to patients $BCL_1$ cells were inoculated into mice reconstituted with human CD27 transgenic (huCD27 tg) bone marrow (FIG. 17A). In this model, the clinical candidate anti-huCD27 mAb, varlilumab (Vitale et al., 2012) was employed. As before, we observed a modest improvement in survival with anti-CD20 alone (median survival 44 days). The therapeutic effect of anti-huCD27 monotherapy was again modest, but when given in combination with anti-CD20, significantly enhanced survival benefit was seen with >70% mice treated with the combination surviving >100 days compared to 0% with either monotherapy.

Figure 17B:
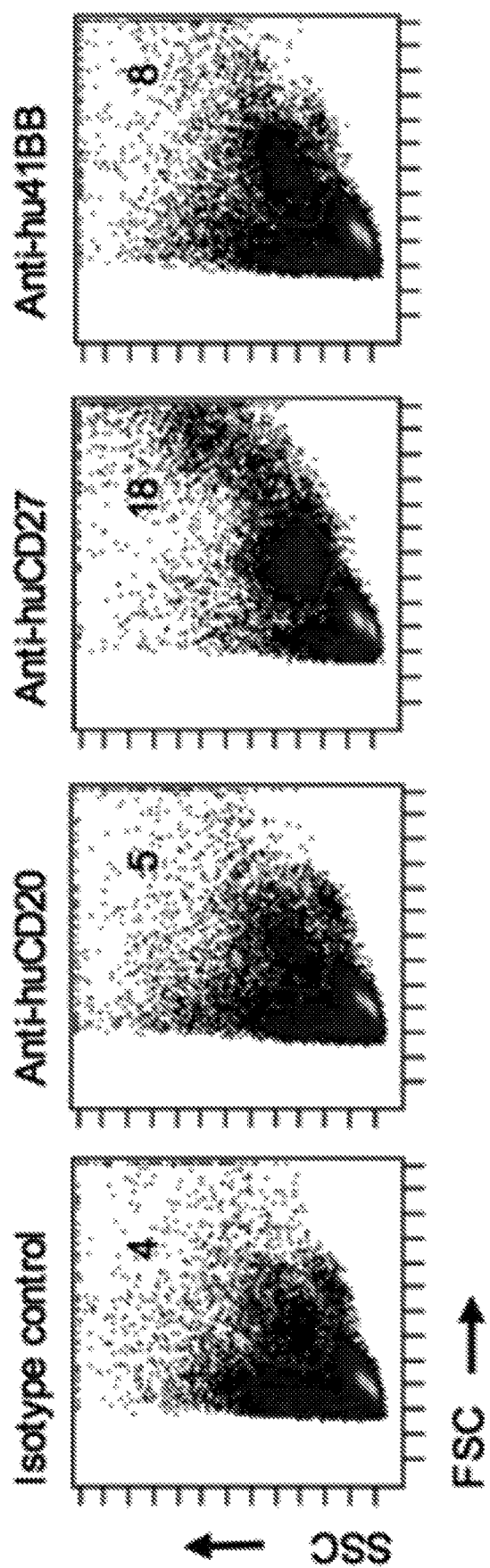
Figure 17C:
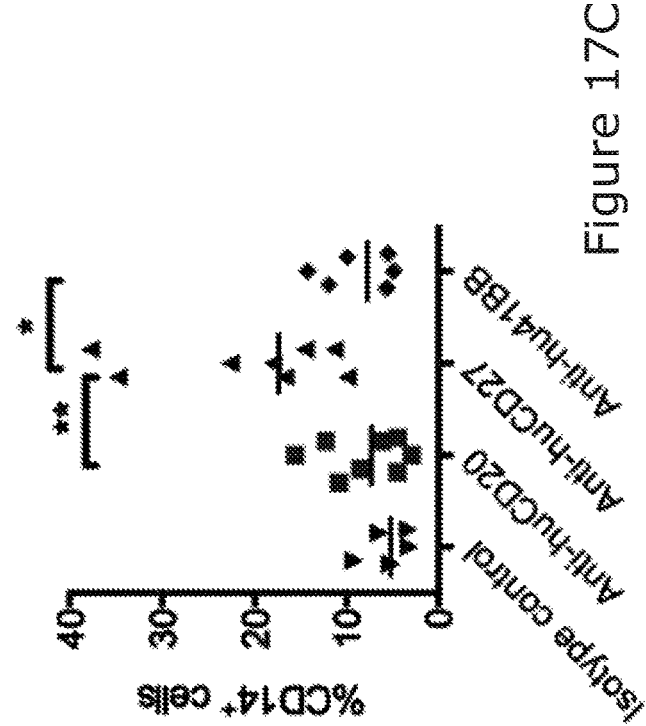
Figure 17D:
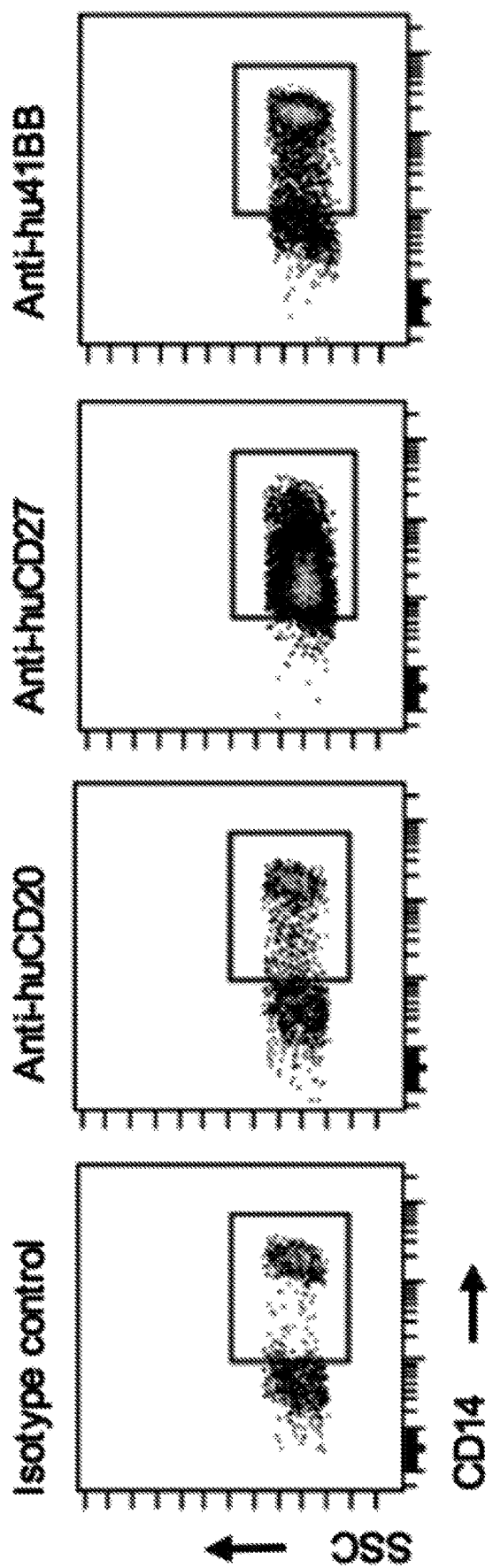
Figure 17E:
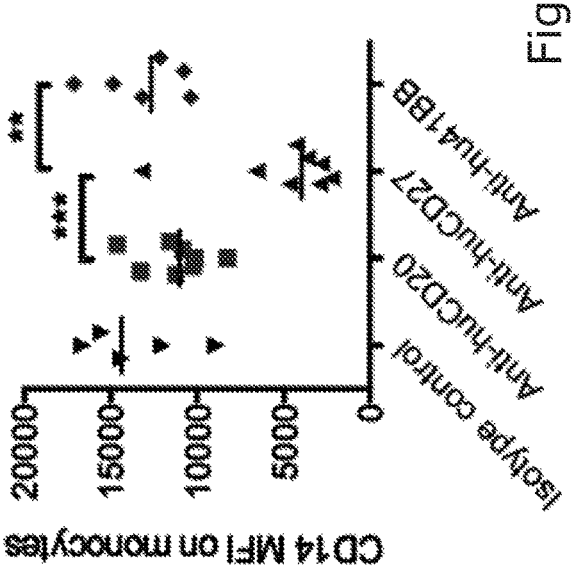
Figure 17F:
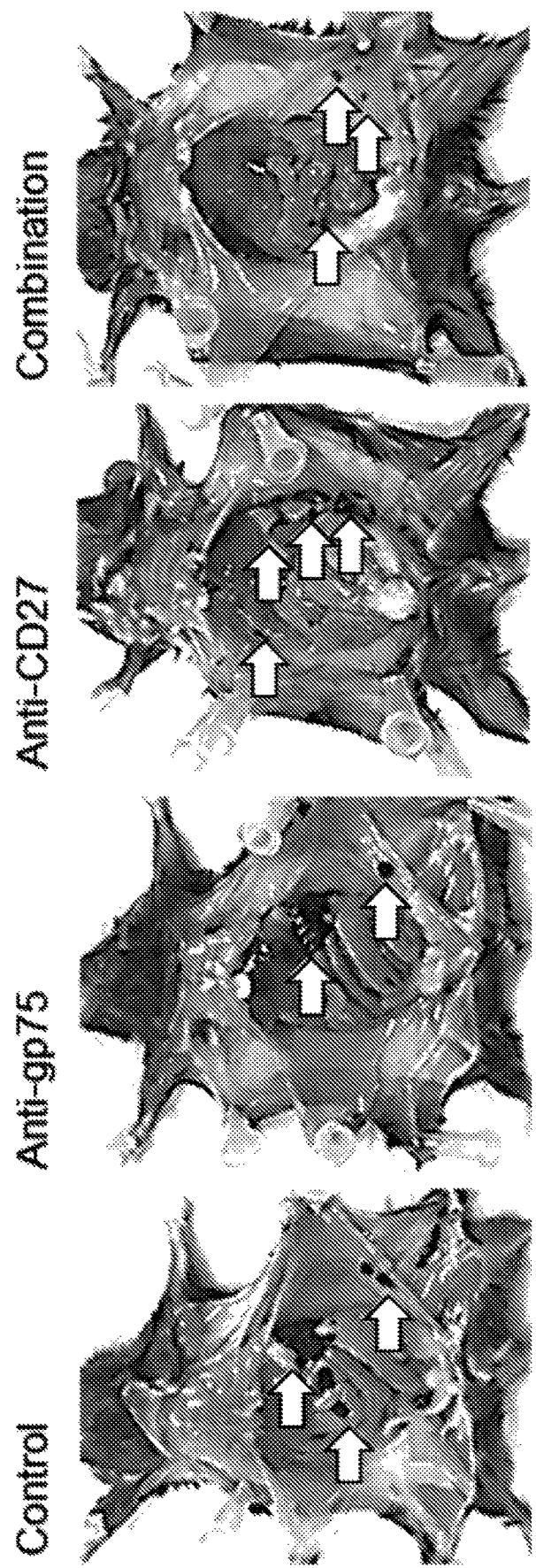
Figure 17G:
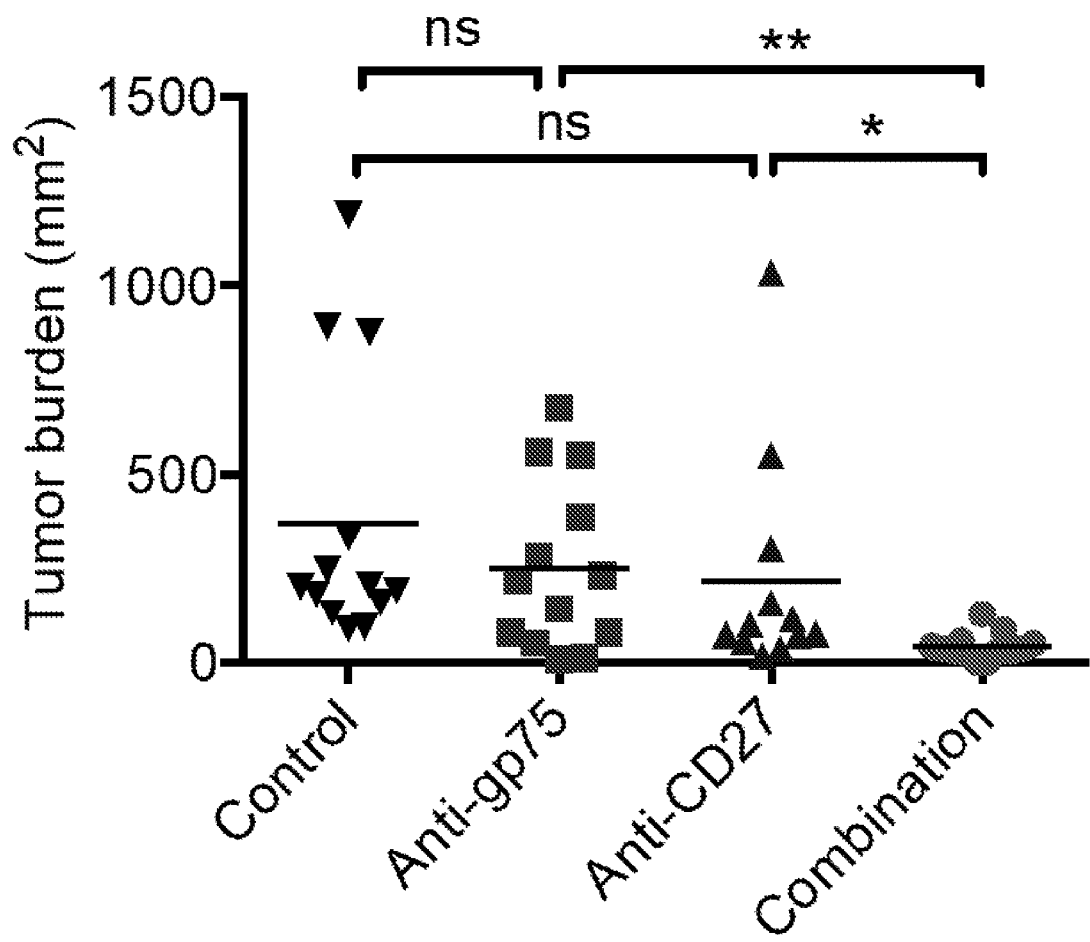

Next, we studied the in vitro effects of anti-huCD27 on peripheral blood mononuclear cells (PBMC) derived from healthy human donors (FIGS. 17B-E). PBMCs were incubated with anti-huCD20, anti-huCD27 or another T-cell stimulating mAb, anti-hu4-1BB for 48 hours before analysis by flow cytometry. Cultures treated with anti-huCD27 contained 3-fold more monocytes than cultures treated with the other mAbs, suggesting that anti-huCD27 improved monocyte viability (FIGS. 17B and 17C). On further examination, the level of CD14 on monocytes was seen to be downregulated 2-fold after anti-huCD27 treatment (FIGS. 17D and 17E), which is recognized to be associated with differentiation into macrophages. In human PBMCs, CD27 is expressed on T cells, a small subset of B cells but not myeloid cells. Thus, analogous to our murine observations, our data indicate that anti-huCD27 directly stimulates CD27+ T cells to release cytokines that promote monocyte viability and potentially, differentiation into macrophages.

Discussion

It is not yet understood how we should best combine individual mAbs in cancer therapy and which combinations will be effective. Our data demonstrates a previously unheralded way in which an immunostimulatory mAb, (anti-CD27) can be used to enhance the ADCP mediated by a direct, tumor-targeting mAb (anti-CD20) to elicit experimental cures; highlighted schematically in the graphical abstract. Anti-CD20 binds to B cells and mediates macrophage phagocytosis of the mAb-opsonized cells. Addition of anti-CD27 direct stimulates CD8+ T cells and to a lesser extent, NK cells, inducing the release of CCL3, CCL4 and CCL5 which attract myeloid cells. Stimulation of CD8+ T cells (and potentially NK cells) by anti-CD27 also induces release of IFNγ which activates macrophages to express more FcγRIV and interferon responsive genes, thus increasing the number of macrophages to perform ADCP, and also enhancing their phagocytic ability.

In contrast, apart from anti-OX40, none of the other immunomodulatory mAbs tested enhanced the anti-tumor activity of anti-CD20 in the $BCL_1$ model (FIG. 11). The superior therapy observed with the combination could simply be a summation of effects as anti-CD27 on its own significantly prolongs the survival of mice (FIG. 12A). Two lines of evidence indicate that this is not the case: First, the depletion of CD4+ and CD8+ T cells entirely abrogates anti-CD27 activity, but not combination therapy, signifying that in combination, synergistic mechanisms of anti-tumor activity come into play. Second, the 4-1BB mAb was also highly effective as monotherapy but did not result in a robust combination effect with anti-CD20 in our model systems. This might seem contradictory with previously published data which indicated that anti-4-1BB enhanced anti-CD20 therapy (Kohrt et al., 2011), but xenografts were employed previously, in contrast to the syngeneic models here.

There is ample evidence to support the role of CD27 as a co-stimulatory receptor on T cells. Humans deficient in CD27 or CD70 are at risk of EBV-associated lymphoproliferative disorders as a result of reduced proliferation of EBV-specific T cells, which depend on stimulation by EBV-infected, CD70-expressing B cells. Our data demonstrates that anti-CD27 monotherapy is entirely dependent on T cells in the $BCL_1$ lymphoma model (FIG. 13E). Consistent with these findings, others have also demonstrated that anti-CD27 mAb slowed tumor development in the B16cOVA model, and that therapy was entirely abrogated upon CD8+ T cell depletion (Roberts et al., 2010). In this setting, CD4+ T cell depletion did not compromise therapy. Similarly, the anti-huCD27 mAb, varlilumab, is dependent on T cells for therapeutic effects in EG7 lymphoma and CT26 colon carcinoma models. Here, depletion of either CD4+ or CD8+ T cells abrogated varlilumab therapy.

Our data also demonstrated that anti-CD27 and combination therapy increased the total number of tumor-infiltrating Tregs (FIG. 13C), although the ratio of CD8+/Treg was still significantly higher in the combination group compared to anti-CD20 only. Detailed studies have shown that the CD27/CD70 pathway is essential for Treg development in the thymus by rescuing these cells from apoptosis through inhibition of the mitochondrial apoptosis pathway. Further, in CD27−/− mice, tumor development in several transplantable and carcinogen-induced models was reduced compared to WT mice, although inhibition of CD70 post-tumor inoculation had a small impact on tumor progression. These studies also illustrated that whilst the CD27/CD70 pathway increases Treg survival/proliferation, there was no evidence that it enhances Tregs' suppressive function.

Existing literature describing the effects of CD27 stimulation on NK cells are limited (Kelly et al., 2002; Takeda et al., 2000). In vitro assays demonstrate that engagement of CD27 by an agonistic mAb induces proliferation and IFNγ secretion in NK cells, but without any evidence of direct cytotoxicity (Takeda et al., 2000). In vivo, transfection of murine lymphoma cell lines, RMA and EG7 with CD70, the ligand for CD27, resulted in NK-dependent tumor rejection via perforin and IFNγ. CD27 stimulation of NK cells in these circumstances also resulted in development of a secondary T-cell memory response (Kelly et al., 2002). In a B16cOVA model of anti-CD27 therapy closer to ours, NK cells were shown to be essential in early tumor control, but dispensable when tumor engraftment was established. Further, in both humans and mice, CD27 can be used to subdivide NK cells into different developmental and functional subsets. $CD27^{hi}$ expressing NK cells are enriched in lymphoid organs and are less prominent in the peripheral blood, and CD27 is lost on maturation in both species. Functionally, murine $CD27^{hi}$ expressing NK cells exhibit greater effector function in terms of in vitro cytotoxicity and IFNγ release, whereas the functional ability of human CD27+ NK cells is less established. Human CD27$^+$ NK cells contain less perforin, granzyme B and exhibited reduced direct cytotoxicity compared to CD27$^-$ NK cells but showed greater IL-12/IL-15/IL-18-dependent IFNγ release. Our chemokine and cytokine profiling data show that CD27 stimulation is associated with TRAIL and FASL upregulation, indicative of increased cellular cytotoxicity but this could be from either T or NK cells, or both (FIG. 15A). IFNγ upregulation was observed on both T and NK cells with CD27 stimulation by single cell RNA sequencing (FIG. 22E), albeit the number of NK cells collected were small, thus reducing our ability to detect changes in NK cells. At the protein level, evidence of direct NK activation by anti-CD27 is supported by the upregulation of KLRG1, which is expressed on terminally differentiated NK cells. In a pulmonary metastatic colorectal model, KLRG1$^+$ NK cells were shown to be crucial in protecting against tumor development in a perforin-dependent manner. Altogether, these data suggest that anti-CD27 is able to directly stimulate NK cells to enhance cytokine effector function and possibly also direct cytotoxicity. Indeed, when administered in combination, depletion of both T and NK cells is required to abrogate therapy (FIG. 13G), indicating that loss of either population can in part, be compensated by anti-CD27 mediated activation of the other.

Figure 16A:
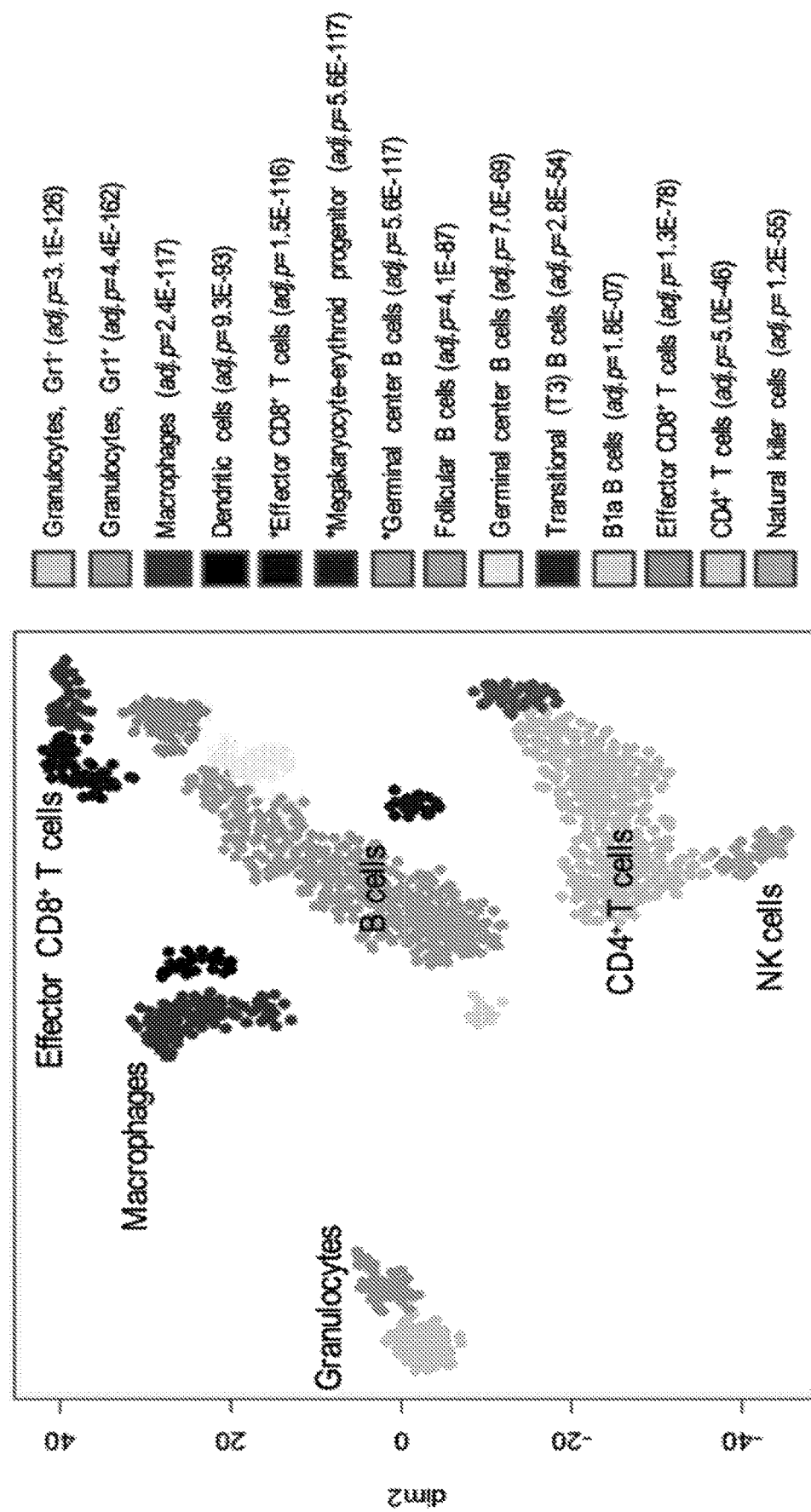
Figure 16B:
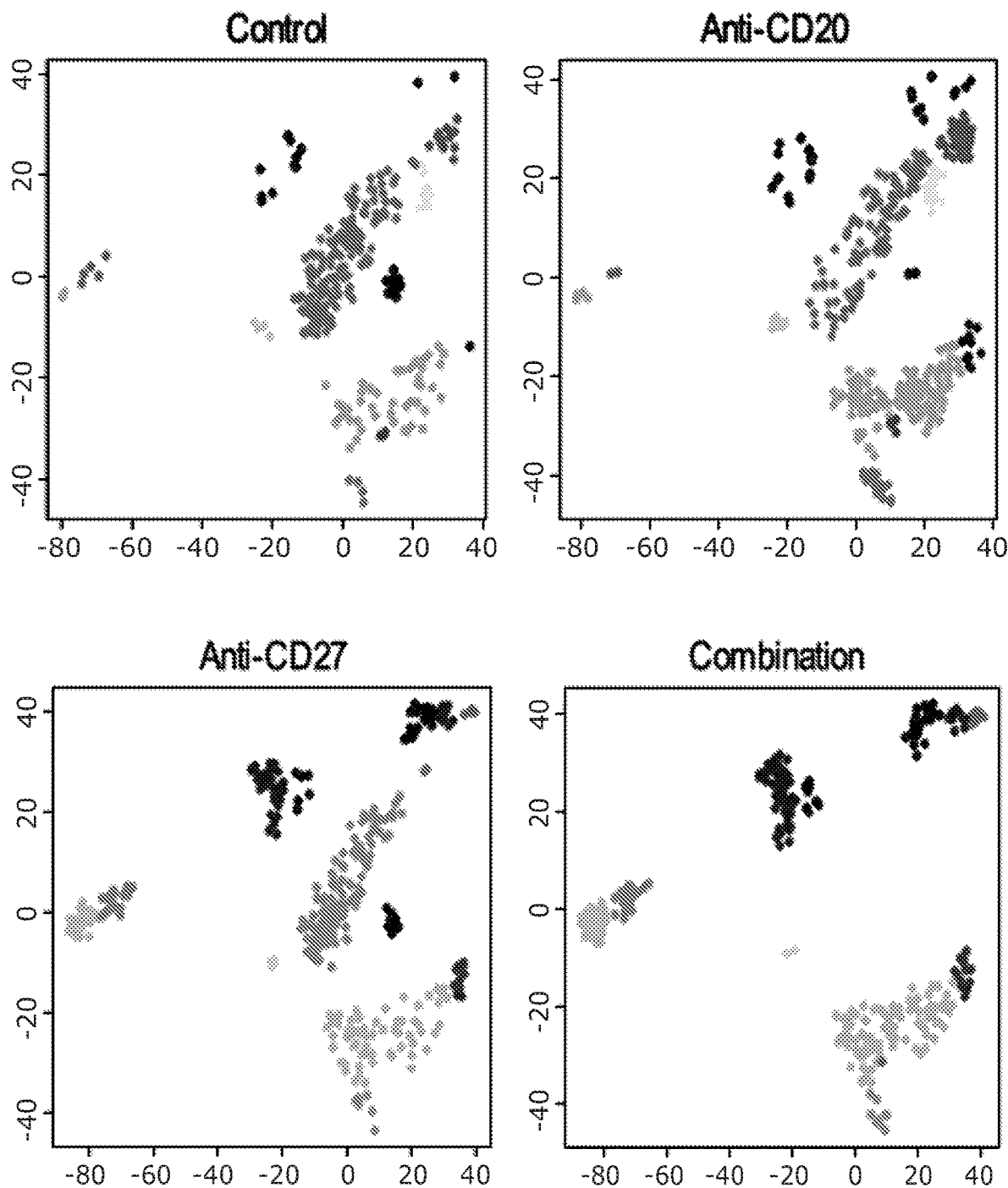
Figure 16C:
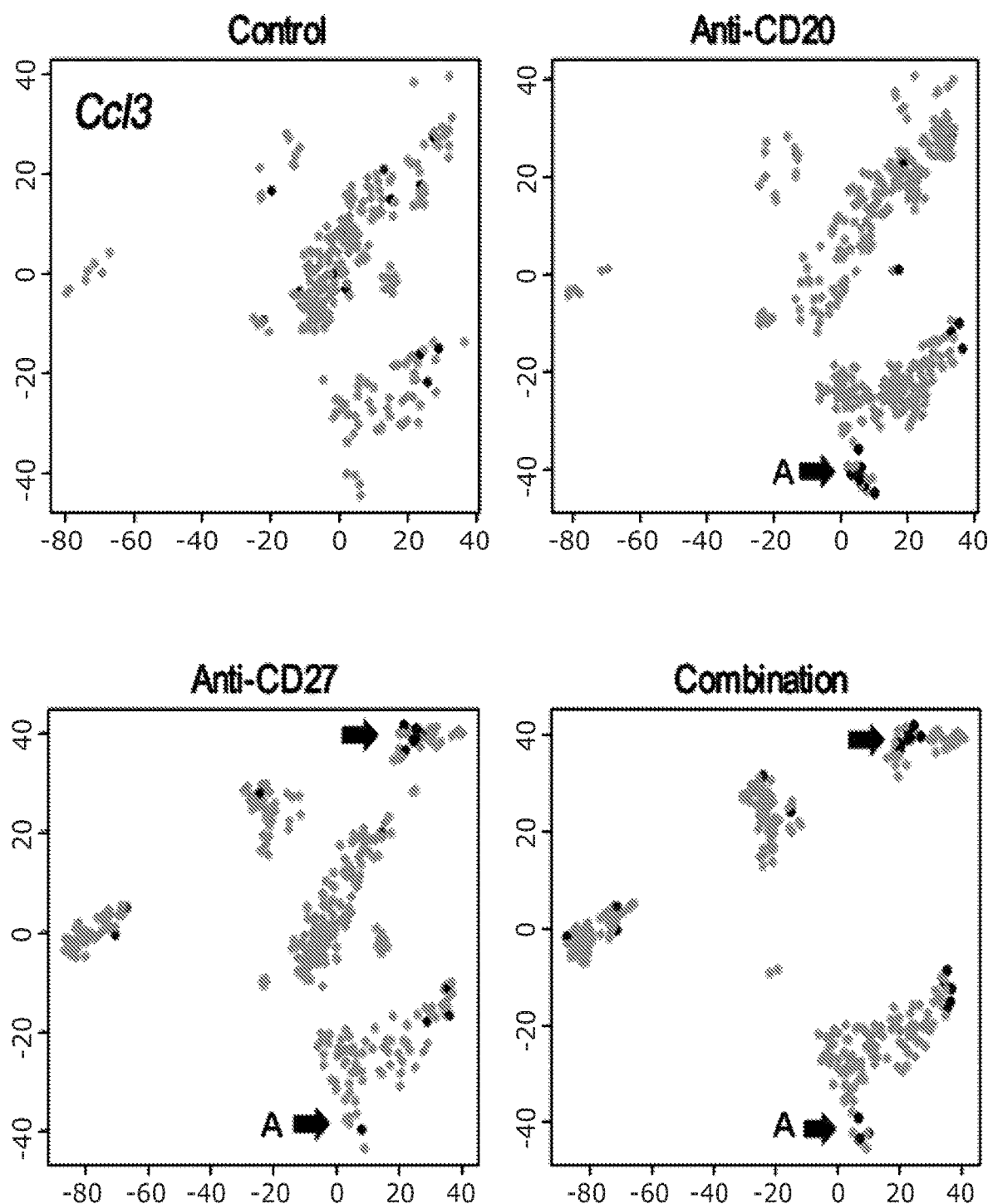
Figure 16D:
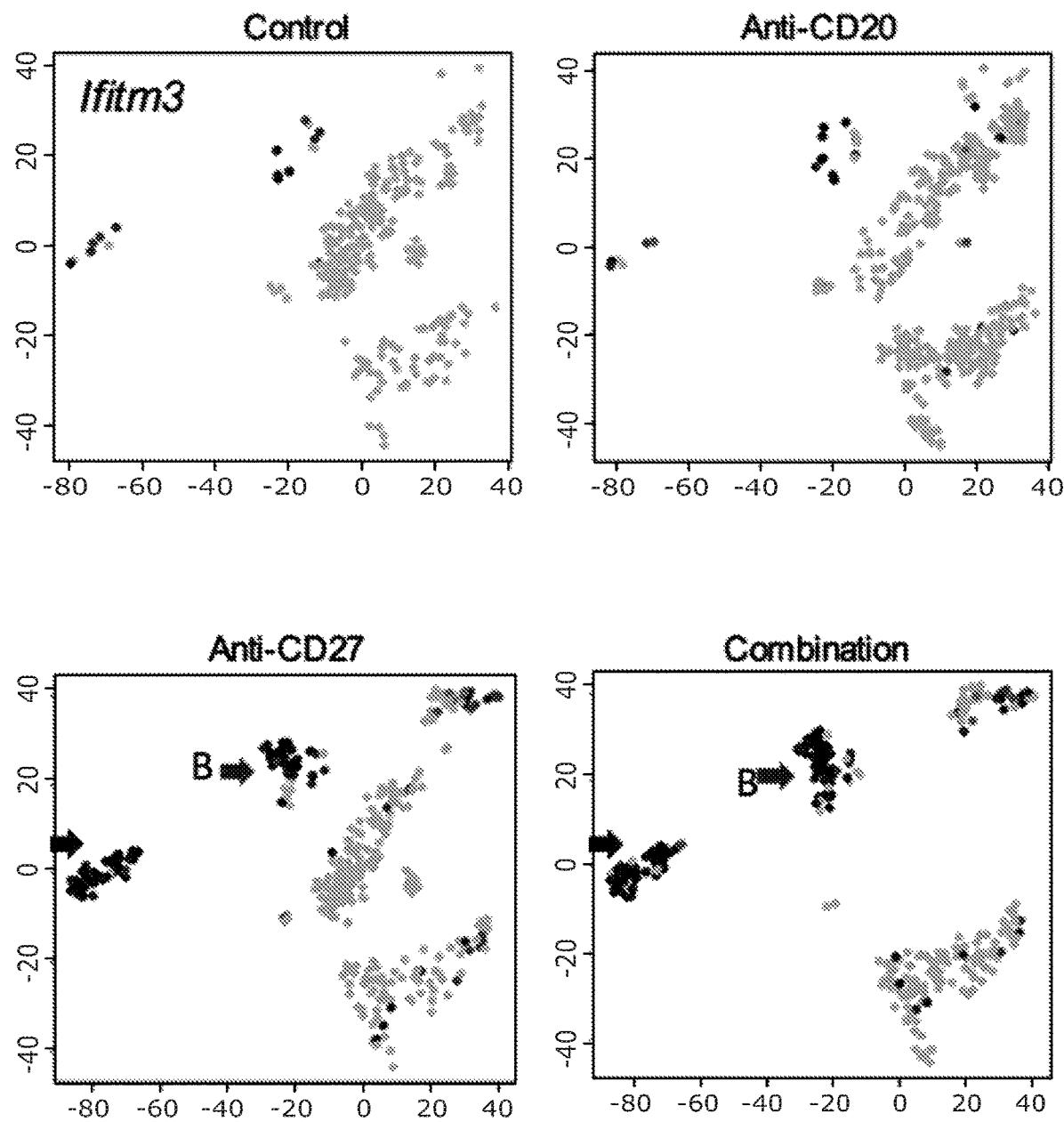
Figure 16E:
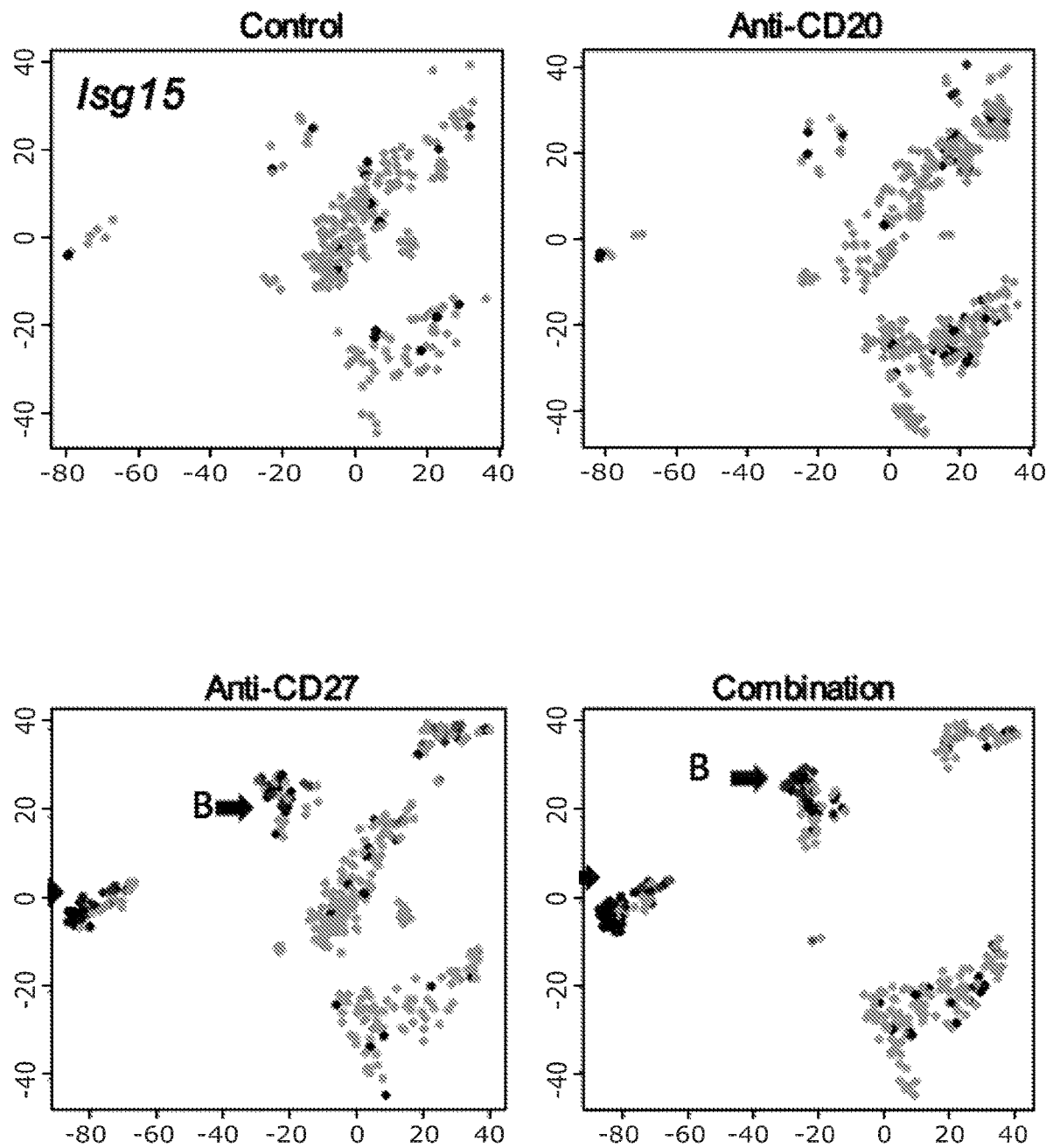

Our data demonstrates that administration of anti-CD27 is associated with a large inflammatory infiltrate of monocytes, neutrophils (FIGS. 15E and 15F) and macrophages (FIGS. 15G and 16B). The infiltration of these myeloid cells indicates that anti-CD27 therapy is capable of triggering an inflammatory environment by promoting the release of CCL3, CCL4 and CCL5 from effector CD8$^+$ T cells (FIGS. 16C, 22B and 22C). Expression of IFNγ and the chemokines were also detected on NK cells at lower levels, which supports CD8$^+$ T cells as the main cellular effectors of CD27 stimulation. The infiltrating macrophages showed increased expression of class II, CD86 and FcγRIV (FIGS. 15C and 15D) and strongly expressed interferon response genes (FIGS. 16D and 16E). The upregulation of FcγRIV on macrophages strongly support the hypothesis that these cells have an enhanced ability to mediate ADCP. Contradictory to these findings are others' observations that tumor-associated macrophages are conventionally associated with a poor prognosis across a number of different cancers as it has the capacity to support tumor growth through secretion of immunosuppressive cytokines amongst other factors (reviewed in (Weiskopf and Weissman, 2015)). Indeed, we observed that depletion of macrophages slowed the growth of BCL$_1$ (FIG. 20C). However, macrophages are also the key effectors of ADCP and in follicular lymphoma where rituximab is employed, increased tumor-associated macrophages predicted a favorable outcome (Taskinen et al., 2007). Most significantly, our human in vitro data (FIG. 17) corroborate our murine findings by demonstrating that the anti-huCD27 mAb, varlilumab promotes monocyte viability and potentially differentiation into macrophages. We hypothesize that these effects occur via direct CD8$^+$ T cell differentiation, and are in the process of studying this further. It is of particular interest that the agonistic mAb to 4-1BB did not produce the same effects, despite being another co-stimulator receptor on T cells. We suspect these differences are due to the fact that CD27 is constitutively expressed whereas 4-1BB expression requires prior activation.

Finally, our data indicates that anti-CD27 is also effective in enhancing direct tumor targeting mAbs beyond anti-CD20. Anti-CD27 can be used to enhance the effects of other direct targeting mAbs such as anti-CD38 in myeloma and anti-EGFR in solid tumors.

Experimental Procedures

Mice

Mice were supplied by Charles River Laboratories and maintained in local facilities. BCL$_1$ (Slavin and Strober, 1978) and A31 (Cobb et al., 1986) B-cell lymphoma lines were maintained by passage in BALB/c mice and CBA/H mice, respectively. Animal experiments were conducted according to the UK Home Office license guidelines and approved by the University of Southampton Ethical Committee. HuCD27 tg mice (He et al., 2013) on BALB/c background were maintained in Celldex animal facilities and used according to the Institutional Animal Care and Use Committees guidelines.

Lymphocyte Isolation and Flow Cytometry

Flow cytometry was performed as previously described (Tutt et al., 1998) using FACSCalibur or FACSCanto (all from BD Biosciences) with data analyzed using Cytobank (Cytobank).

Peripheral blood and/or spleen suspensions were analyzed for CD8$^+$ T subsets (anti-CD3, anti-CD8, anti-CD44, anti-CD62L), Tregs (anti-CD3 PerCP eFluor 710, anti-CD4 FITC, anti-CD25 APC, anti-FOXP3 PE), BCL$_1$ tumour (anti-CD19 APC, anti-BCL$_1$ idiotype FITC), NK cells (anti-CD3 FITC, anti-NKp46 PE, anti-CD49b PerCP eFluor 710) and myeloid cells (anti-CD11b e450, anti-F4/80 Alexa Fluor 647, anti-Ly6g APC e780, anti-Lytic PE Cy7) and CD27 expression (anti-human CD27 PE, anti-mouse CD27 PE), in the presence of the FcγR blocking mAb, 2.4G2. All conjugated antibodies were purchased from BD Biosciences and EBioscience except for 2.4G2 (in-house), anti-BCL$_1$ idiotype FITC (in-house) and anti-F4/80 Alexa Fluor 647 (Bio-Rad Laboratories).

To enumerate myeloid cells in the spleen, tissue digestion was performed using Liberase (Sigma Aldrich) after tissue harvest as per manufacturer's protocol. Briefly, harvested tissue was cut into small pieces and treated in Liberase TL for 15 min before mashing into a single cell suspension.

Tumor Models

Groups of 8- to 12-week old female BALB/c mice (n=5-6) received 10$^4$ BCL$_1$ or A31 cells intravenously on day 0 followed by anti-CD20 (200 µs) on day 4 and anti-CD27 (100 µg/injection) from day 5-8 by intraperitoneal injection. Alternatively, BCL$_1$-inoculated mice received an alternative immunomodulatory mAb from day 5 onwards as specified in the legends. For the A31 model, mAb therapy was repeated again at the same dose and sequence from day 15-18. 1×10$^7$ Eµ-TCL1 cells were intraperitoneally injected into groups of 6- to 8-week old female C57BL/6 mice and leukemic burden monitored by tail bleeds and CD5/B220 expression through flow cytometry as before (Carter et al., 2016). Animals were treated with anti-CD20 (250 µs) and anti-CD27 (100 µs) 1 day later when more than 10% B220$^+$CD5$^{int}$ lymphocytes were present in the blood. Animals were euthanized when humane end points were reached or >80% of lymphocytes were tumor cells and WBC counts >5×10$^7$/ml.

For the study of varlilumab, six-week old female BALB/c recipient mice were irradiated and reconstituted with huCD27 tg bone marrow cells. Eight to 10-weeks after bone marrow transplantation, animals were bled and huCD27 expression inspected by flow cytometry, before implantation with BCL$_1$.

For depletion experiments, mice were treated with YTS169 (CD8 depletion, in house), GK1.5 (CD4 depletion, in house) and asialo-GM1 (NK depletion, BioLegend) at doses of 0.5-1 mg, 1 mg and 10-20 µl per injection, every 5 days, from day −1 to day −16 i.p.

Antibodies

18B12 (anti-CD20) (Brezinsky et al., 2003) was produced in-house from published patented sequences as previously described (Williams et al., 2012). AT124-1 (anti-CD27) (French et al., 2007), Mc39-16 (anti-A31 idiotype) (Tutt et al., 1998), Mc10-6A5 (anti-BCL$_1$ idiotype) (George et al., 1991), OX86 (anti-OX40) (al-Shamkhani et al., 1996), SAP45-9 (anti-TIGIT), LOB12.3 (anti-4-1BB), YTS169 (anti-CD8), GK1.5 (anti-CD4) were produced from the culture supernatant of hybridoma cells or stably transfected Chinese hamster ovary cells. 10F.9G2 (anti-PD-L1), RMP1-14 (anti-PD-1), 9D9 (anti-CTLA4), DTA-1 (anti-GITR) mAbs were purchased from BioXcell. The NK depleting antibody, anti-asialoGM1 was purchased from Biolegend. Anti-human CD27 mAb, varlilumab (He et al., 2013), was gifted by Celldex and produced as previously described.

Cytokine and Chemokine Profiling

The spleens of treated mice were harvested on day 6, snap frozen and RNA purified. RNA was converted to cDNA using the RT$^2$ first strand kit (Qiagen) and qPCR performed using RT$^2$ SYBR Green qPCR mastermix (Qiagen) and RT$^2$ profiler PCR array for mouse cytokines and chemokines (Qiagen) as per manufacturer's protocol. Data analysis was performed using the $\Delta\Delta C_T$ method and SABiosciences PCR Array Data Analysis Web portal.

Single Cell RNA Sequencing

The spleens of treated mice were harvested on day 13 and digested with Liberase (Sigma). Briefly, single cells and barcoded mRNA-binding micro-particles were suspended in droplets containing cell lysis buffer. The droplets were then broken using a custom-built microfluidic platform. Subsequent cDNA synthesis allows the incorporation of the barcode to every transcript from a single cell. Fragment cDNA was then amplified (Nextera XT, Illumina) and sequenced on an Illumina NextSeq-500. Raw sequencing reads were converted to a sorted unmapped BAM file and filtered, aligned and differential gene expression analyzed using the Seurat R package (Rahul Satija (NA). Seurat: R toolkit for single cell genomics. R package version 1.4.0.) ($p<1\times10^{-3}$ was considered significant). Data has been deposited in NCBI Geo (accession number GSE97037).

Immunohistochemistry

Spleens were harvested on day 9 and embedded in OCT (CellPath) and frozen in isopentane. Eight µm slices were air-dried overnight, fixed in 100% acetone and blocked with 2.5% normal goat serum and stained for BCL1 cells (anti-BCL idiotype), normal B cells (anti-B220), neutrophils (anti-Ly6c/Ly6g), macrophage (anti-F4/80) and monocyte (anti-CD14). Sections were treated with a peroxidase inhibitor (Pierce) for 10 min before incubation with an HRP-conjugated anti-rat IgG polymer for 30 min, followed by 3,3'-diaminobenzidine for 5 min, and counterstained with haematoxylin (all from Vector Laboratories). Images were recorded using a CXK41 inverted microscope equipped with a CC12 color camera, Plan Achromat 4×0.25 objective lens and Cell B software (all from Oympus).

In Vitro Human PBMC Based Assays

PBMCs were obtained from healthy volunteers through Southampton National Blood Service, and density gradient centrifugation (Lymphoprep, Axis-Shield) performed within 4 hours. Use of human samples was approved by the local ethical committee, in accordance with the Declaration of Helsinki.

PBMCs were cultured using serum-free media (CTL-Test Medium, CTL) supplemented with glutamine (2 mM), pyruvate (1 mM), penicillin, and streptomycin (100 IU/mL) at 37° C. in 5% $CO_2$. Cells were cultured in a 24-well plate at $1\times10^7$ cells/ml ($1.5\times10^7$ cells/well) and stimulated with cetuximab and rituximab (both from Southampton General Hospital oncology pharmacy), anti-4-1BB (clone 3/28, in house) or varlilumab (Celldex Therapeutics) at 5 µg/mL for 48 hours. Post culture, PBMCs were labelled with anti-CD14-Pacific Blue (BioLegend) and analyzed on a FACSCanto flow cytometer (BD Biosciences).

Statistics

Statistical analysis was performed using a two-tailed Students t test (paired/unpaired as specified individually) in Graphpad Prism version 6 software. To assess survival differences in immunotherapy experiments, Kaplan-Meier curves were produced and analyzed by log-rank testing. p values<0.05 were regarded as statistically significant.

REFERENCES al-Shamkhani, A., Birkeland, M. L., Puklavec, M., Brown, M. H., James, W., and Barclay, A. N. (1996). OX40 is differentially expressed on activated rat and mouse T cells and is the sole receptor for the OX40 ligand. Eur. J. Immunol. 26, 1695-1699.

Bichi, R., Shinton, S. A., Martin, E. S., Koval, A., Calin, G. A., Cesari, R., Russo, G., Hardy, R. R., and Croce, C. M. (2002). Human chronic lymphocytic leukemia modeled in mouse by targeted TCL1 expression. Proc. Natl. Acad. Sci. USA 99, 6955-6960.

Brezinsky, S. C., Chiang, G. G., Szilvasi, A., Mohan, S., Shapiro, R. I., MacLean, A., Sisk, W., and Thill, G. (2003). A simple method for enriching populations of transfected CHO cells for cells of higher specific productivity. J. Immunol. Methods 277, 141-155.

Carter, M. J., Cox, K. L., Blakemore, S. J., Turaj, A. H., Oldham, R. J., Dahal, L. N., Tannheimer, S., Forconi, F., Packham, G., and Cragg, M. S. (2016). PI3Kdelta inhibition elicits anti-leukemic effects through Bim-dependent apoptosis. Leukemia (In Press) doi: 10.1038/leu.2016.333.

Cobb, L. M., Glennie, M. J., McBride, H. M., Breckon, G., and Richardson, T. C. (1986). Characterisation of a new murine B cell lymphoma. Br. J. Cancer 54, 807-818.

French, R. R., Taraban, V. Y., Crowther, G. R., Rowley, T. F., Gray, J. C., Johnson, P. W., Tutt, A. L., Al-Shamkhani, A., and Glennie, M. J. (2007). Eradication of lymphoma by CD8 T cells following anti-CD40 monoclonal antibody therapy is critically dependent on CD27 costimulation. Blood 109, 4810-4815.

George, A. J., McBride, H. M., Glennie, M. J., Smith, L. J., and Stevenson, F. K. (1991). Monoclonal antibodies raised against the idiotype of the murine B cell lymphoma, BCL1 act primarily with heavy chain determinants. Hybridoma 10, 219-227.

Gill, S., Vasey, A. E., De Souza, A., Baker, J., Smith, A. T., Kohrt, H. E., Florek, M., Gibbs, K. D., Jr., Tate, K., Ritchie, D. S., and Negrin, R. S. (2012). Rapid development of exhaustion and down-regulation of eomesodermin limit the antitumor activity of adoptively transferred murine natural killer cells. Blood 119, 5758-5768.

He, L. Z., Prostak, N., Thomas, L. J., Vitale, L., Weidlick, J., Crocker, A., Pilsmaker, C. D., Round, S. M., Tutt, A., Glennie, M. J., et al. (2013). Agonist anti-human CD27 monoclonal antibody induces T cell activation and tumor immunity in human CD27-transgenic mice. J. Immunol. 191, 4174-4183.

Kelly, J. M., Darcy, P. K., Markby, J. L., Godfrey, D. I., Takeda, K., Yagita, H., and Smyth, M. J. (2002). Induction of tumor-specific T cell memory by NK cell-mediated tumor rejection. Nat. Immunol. 3, 83-90.

Kohrt, H. E., Houot, R., Goldstein, M. J., Weiskopf, K., Alizadeh, A. A., Brody, J., Muller, A., Pachynski, R., Czerwinski, D., Coutre, S., et al. (2011). CD137 stimulation enhances the antilymphoma activity of anti-CD20 antibodies. Blood 117, 2423-2432.

Roberts, D. J., Franklin, N. A., Kingeter, L. M., Yagita, H., Tutt, A. L., Glennie, M. J., and Bullock, T. N. (2010). Control of established melanoma by CD27 stimulation is associated with enhanced effector function and persistence, and reduced PD-1 expression of tumor infiltrating CD8(+) T cells. J. Immunother. 33, 769-779.

Takeda, K., Oshima, H., Hayakawa, Y., Akiba, H., Atsuta, M., Kobata, T., Kobayashi, K., Ito, M., Yagita, H., and Okumura, K. (2000). CD27-mediated activation of murine NK cells. J. Immunol. 164, 1741-1745.

Taskinen, M., Karjalainen-Lindsberg, M. L., Nyman, H., Eerola, L. M., and Leppa, S. (2007). A high tumor-associated macrophage content predicts favorable outcome in follicular lymphoma patients treated with rituximab and cyclophosphamide-doxorubicin-vincristine-prednisone. Clin. Cancer Res. 13, 5784-5789.

Turaj, A. H., Dahal, L. N., Beers, S. A., Cragg, M. S., and Lim, S. H. (2017). TLR-3/9 agonists synergize with anti-ErbB2 mAb-Letter. Cancer Res. In press.

Tutt, A. L., French, R. R., Illidge, T. M., Honeychurch, J., McBride, H. M., Penfold, C. A., Fearon, D. T., Parkhouse, R. M., Klaus, G. G., and Glennie, M. J. (1998). Monoclonal antibody therapy of B cell lymphoma: signaling activity on tumor cells appears more important than recruitment of effectors. J. Immunol. 161, 3176-3185.

Weiskopf, K., and Weissman, I. L. (2015). Macrophages are critical effectors of antibody therapies for cancer. mAbs 7, 303-310.

Williams, E. L., Tutt, A. L., French, R. R., Chan, H. T., Lau, B., Penfold, C. A., Mockridge, C. I., Roghanian, A., Cox, K. L., Verbeek, J. S., et al. (2012). Development and characterisation of monoclonal antibodies specific for the murine inhibitory FcgammaRIIB (CD32B). Eur. J Immunol. 42, 2109-2120.

The invention claimed is:

1. A method of treating a B-cell lymphoma or a B-chronic lymphocytic leukemia in a subject comprising:
   administering a therapeutically effective amount of an anti-CD20 antibody or an anti-CD20 binding fragment thereof; and
   administering a therapeutically effective amount of an agonistic anti-CD27 antibody or an anti-CD27 binding fragment thereof,
   wherein, after administration of the anti-CD20 antibody or an anti-CD20 binding fragment thereof and of the agonistic anti-CD27 antibody or an anti-CD27 binding fragment thereof to a mouse in a BCL1 lymphoma mouse model, the probability that the mouse derives a greater survival benefit is greater than the probability that the mouse derives a greater survival benefit after administration of the anti-CD20 antibody or an anti-CD20 binding fragment as a monotherapy or the agonistic anti-CD27 antibody or an anti-CD27 binding fragment thereof as a monotherapy.

2. The method according to claim 1, wherein the anti-CD20 antibody or an anti-CD20 binding fragment thereof comprises rituximab or an anti-CD20 binding fragment thereof, obinutuzumab or an anti-CD20 binding fragment thereof, ocrelizumab or an anti-CD20 binding fragment thereof, ofatumumab or an anti-CD20 binding fragment thereof, veltuzumab or an anti-CD20 binding fragment thereof, TRU-015 or an anti-CD20 binding fragment thereof, EMAB-6 or an anti-CD20 binding fragment thereof, or RhuMAb v114 or an anti-CD20 binding fragment thereof.

3. The method according to claim 2, wherein the anti-CD20 antibody or an anti-CD20 binding fragment thereof comprises rituximab or an anti-CD20 binding fragment thereof.

4. The method according to claim 3, wherein the agonistic anti-CD27 antibody or an anti-CD27 binding fragment thereof comprises varlilumab or an anti-CD27 binding fragment thereof.

5. The method according to claim 4, wherein the rituximab or an anti-CD20 binding fragment thereof comprises:
   rituximab;
   at least one variable domain of rituximab; or
   at least one complementarity determining region of rituximab, wherein the at least one complementarity determining region has the amino acid sequence SYNMH (SEQ ID NO: 1), AIYPGNGDTSYNQKFKG (SEQ ID NO: 2), STYYGGDWYFNV (SEQ ID NO: 3), RASSSVSYIH (SEQ ID NO: 4), ATSNLAS (SEQ ID NO: 5); and QQWTSNPPT (SEQ ID NO: 6).

6. The method according to claim 4, wherein the varlilumab or an anti-CD27 binding fragment thereof comprises:

varlilumab;

at least one variable domain of varlilumab; or at least one complementarity determining region of varlilumab, wherein the at least one complementarity determining region has the amino acid sequence GFTFSSYD (SEQ ID NO: 13); IWYDGSNK (SEQ ID NO: 14); ARGSGNWGFFDY (SEQ ID NO: 15); QGISRW (SEQ ID NO: 16); AAS; and QQYNTYPRT (SEQ ID NO: 17).

7. The method according to claim 4, wherein the rituximab or an anti-CD20 binding fragment thereof comprises an anti-CD20 binding fragment of rituximab that competes for binding with rituximab.

8. The method according to claim 6, wherein the varlilumab or an anti-CD27 binding fragment thereof comprises varlilumab.

9. The method according to claim 4, wherein the varlilumab or an anti-CD27 binding fragment thereof comprises an anti-CD27 binding fragment that competes for binding with varlilumab.

10. The method according to claim 4, wherein when, upon administration, the varlilumab or an anti-CD27 binding fragment thereof stimulates an effector lymphocyte.

11. The method according to claim 10, wherein the effector lymphocyte comprises a natural killer cell or a T-cell.

12. The method according to claim 4, wherein the subject is a human.

13. The method according to claim 4, wherein the subject is a mouse reconstituted with human CD27 transgenic bone marrow.

14. The method according to claim 4, wherein the administration of the rituximab or an anti-CD20 binding fragment thereof and the administration of the varlilumab or an anti-CD27 binding fragment thereof is sequential.

15. The method according to claim 13, wherein the rituximab or an anti-CD20 binding fragment thereof is administered within 1 to 4 days of the varlilumab or the anti-CD27 binding fragment thereof.

16. The method according to claim 4, wherein the administration of the rituximab or an anti-CD20 binding fragment thereof and the administration of varlilumab or an anti-CD27 binding fragment is concurrent.

* * * * *

SEQUENCE LISTING

```
<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: CDR

<400> SEQUENCE: 1

Ser Tyr Asn Met His
1               5

<210> SEQ ID NO 2
<211> LENGTH: 17
<212> TYPE: PRT
<213> ORGANISM: Artificial Sequence
<220> FEATURE:
<223> OTHER INFORMATION: CDR

<400> SEQUENCE: 2

Ala Ile Tyr Pro Gly Asn Gly Asp Thr Ser Tyr Asn Gln Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: CDR

<400> SEQUENCE: 3

Ser Thr Tyr Tyr Gly Gly Asp Trp Tyr Phe Asn Val
1               5                   10

<210> SEQ ID NO 4
<211> LENGTH: 10
<212> TYPE: PRT
<213> ORGANISM: Artificial Sequence
<220> FEATURE:
```

<223> OTHER INFORMATION: CDR

<400> SEQUENCE: 4

Arg Ala Ser Ser Ser Val Ser Tyr Ile His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR

<400> SEQUENCE: 5

Ala Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR

<400> SEQUENCE: 6

Gln Gln Trp Thr Ser Asn Pro Pro Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Antibody chain

<400> SEQUENCE: 7

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: Antibody chain

<400> SEQUENCE: 8

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 9
<211> LENGTH: 451
<212> TYPE: PRT
<213> ORGANISM: Artificial Sequence
<220> FEATURE:
<223> OTHER INFORMATION: Antibody chain

<400> SEQUENCE: 9

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

```
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 10
<211> LENGTH: 213
<212> TYPE: PRT
<213> ORGANISM: Artificial Sequence
<220> FEATURE:
<223> OTHER INFORMATION: Antibody chain

<400> SEQUENCE: 10

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
            195                 200                 205
Asn Arg Gly Glu Cys
            210

<210> SEQ ID NO 11
<211> LENGTH: 119
<212> TYPE: PRT
<213> ORGANISM: Artificial Sequence
<220> FEATURE:
<223> OTHER INFORMATION: Antibody chain

<400> SEQUENCE: 11

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Asp Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Ser Gly Asn Trp Gly Phe Phe Asp Tyr Trp Gly Gln Gly
            100                 105                 110
Thr Leu Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Antibody chain

<400> SEQUENCE: 12

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Arg Trp
            20                  25                  30
Leu Ala Trp Tyr Gln Gln Lys Pro Glu Lys Ala Pro Lys Ser Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Thr Tyr Pro Arg
                85                  90                  95
Thr Phe Gly Gln Gly Thr Lys Val Glu Ile Lys
            100                 105

<210> SEQ ID NO 13
<211> LENGTH: 8
<212> TYPE: PRT
```

-continued

```
<213> ORGANISM: Artificial Sequence
<220> FEATURE:
<223> OTHER INFORMATION: CDR

<400> SEQUENCE: 13

Gly Phe Thr Phe Ser Ser Tyr Asp
1               5

<210> SEQ ID NO 14
<211> LENGTH: 8
<212> TYPE: PRT
<213> ORGANISM: Artificial Sequence
<220> FEATURE:
<223> OTHER INFORMATION: CDR

<400> SEQUENCE: 14

Ile Trp Tyr Asp Gly Ser Asn Lys
1               5

<210> SEQ ID NO 15
<211> LENGTH: 12
<212> TYPE: PRT
<213> ORGANISM: Artificial Sequence
<220> FEATURE:
<223> OTHER INFORMATION: CDR

<400> SEQUENCE: 15

Ala Arg Gly Ser Gly Asn Trp Gly Phe Phe Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: CDR

<400> SEQUENCE: 16

Gln Gly Ile Ser Arg Trp
1               5

<210> SEQ ID NO 17
<211> LENGTH: 9
<212> TYPE: PRT
<213> ORGANISM: Artificial Sequence
<220> FEATURE:
<223> OTHER INFORMATION: CDR

<400> SEQUENCE: 17

Gln Gln Tyr Asn Thr Tyr Pro Arg Thr
1               5

<210> SEQ ID NO 18
<211> LENGTH: 121
<212> TYPE: PRT
<213> ORGANISM: Artificial Sequence
<220> FEATURE:
<223> OTHER INFORMATION: Antibody chain

<400> SEQUENCE: 18

Glu Val Gln Leu Gln Gln Ser Gly Ala Glu Leu Val Arg Pro Gly Ala
1               5                   10                  15

Leu Val Lys Leu Ser Cys Lys Thr Ser Gly Phe Asn Ile Lys Asp Tyr
                20                  25                  30

Phe Leu His Trp Val Arg Gln Arg Pro Asp Gln Gly Leu Glu Trp Ile
            35                  40                  45
```

```
Gly Trp Ile Asn Pro Asp Asn Gly Asn Thr Val Tyr Asp Pro Lys Phe
        50                  55                  60

Gln Gly Thr Ala Ser Leu Thr Ala Asp Thr Ser Asn Thr Val Tyr
65                  70                  75                  80

Leu Gln Leu Ser Gly Leu Thr Ser Glu Asp Thr Ala Val Tyr Phe Cys
                85                  90                  95

Thr Arg Arg Asp Tyr Thr Tyr Glu Lys Ala Ala Leu Asp Tyr Trp Gly
                100                 105                 110

Gln Gly Thr Thr Val Thr Val Ser Thr
            115                 120

<210> SEQ ID NO 19
<211> LENGTH: 107
<212> TYPE: PRT
<213> ORGANISM: Artificial Sequence
<220> FEATURE:
<223> OTHER INFORMATION: Antibody chain

<400> SEQUENCE: 19

Ile Gln Met Ser Gln Ser Pro Ala Ser Leu Ser Ala Ser Val Gly Glu
1               5                   10                  15

Thr Val Thr Ile Thr Cys Arg Ala Ser Gly Asn Ile Tyr Asn Tyr Leu
                20                  25                  30

Ala Trp Tyr Gln Gln Lys Gln Gly Lys Ser Pro His Leu Leu Val Tyr
            35                  40                  45

Asp Ala Lys Thr Leu Ala Asp Gly Val Pro Ser Arg Phe Ser Gly Ser
        50                  55                  60

Gly Ser Gly Thr Gln Tyr Ser Leu Lys Ile Ser Ser Leu Gln Thr Glu
65                  70                  75                  80

Asp Ser Gly Asn Tyr Tyr Cys Gln His Phe Trp Ser Leu Pro Phe Thr
                85                  90                  95

Phe Gly Ser Gly Thr Lys Leu Glu Ile Lys Arg
                100                 105
```